(12) United States Patent
Yamada et al.

(10) Patent No.: US 10,476,009 B2
(45) Date of Patent: Nov. 12, 2019

(54) ORGANIC COMPOUND, LIGHT-EMITTING ELEMENT, DISPLAY MODULE, LIGHTING MODULE, LIGHT-EMITTING DEVICE, DISPLAY DEVICE, ELECTRONIC DEVICE, AND LIGHTING DEVICE

(71) Applicant: Semiconductor Energy Laboratory Co., Ltd., Kanagawa-ken (JP)

(72) Inventors: Yui Yamada, Kanagawa (JP); Hideko Inoue, Kanagawa (JP); Tsunenori Suzuki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 89 days.

(21) Appl. No.: 15/043,792

(22) Filed: Feb. 15, 2016

(65) Prior Publication Data

US 2016/0240794 A1 Aug. 18, 2016

(30) Foreign Application Priority Data

Feb. 18, 2015 (JP) ................. 2015-029560

(51) Int. Cl.
*H01L 51/00* (2006.01)
*C07D 401/14* (2006.01)
*H01L 51/50* (2006.01)

(52) U.S. Cl.
CPC ........ *H01L 51/0072* (2013.01); *C07D 401/14* (2013.01); *H01L 51/0058* (2013.01); *H01L 51/0067* (2013.01); *H01L 51/5072* (2013.01); *H01L 51/5092* (2013.01)

(58) Field of Classification Search
CPC ............. H01L 51/0072; H01L 51/0067; H01L 51/0058; H01L 51/5092; H01L 51/5072; C07D 401/14
See application file for complete search history.

(56) References Cited

U.S. PATENT DOCUMENTS

| | | | |
|---|---|---|---|
| 7,649,077 B2 | 1/2010 | Craig et al. | |
| 8,012,602 B2 | 9/2011 | Schäfer et al. | |
| 9,087,964 B2 | 7/2015 | Hatano et al. | |
| 9,147,849 B2 | 9/2015 | Nam et al. | |
| 9,209,355 B2 | 12/2015 | Senda et al. | |
| 9,231,042 B2 | 1/2016 | Nishido et al. | |
| 2010/0240892 A1 | 9/2010 | Schäfer et al. | |
| 2014/0054561 A1* | 2/2014 | Nam .................. | H01L 51/0072 257/40 |
| 2014/0103385 A1 | 4/2014 | Hatano et al. | |
| 2014/0175469 A1 | 6/2014 | Dozen et al. | |
| 2014/0231770 A1 | 8/2014 | Inoue et al. | |
| 2015/0041792 A1 | 2/2015 | Suzuki et al. | |
| 2016/0181550 A1 | 6/2016 | Yamada et al. | |
| 2016/0248024 A1 | 8/2016 | Shin et al. | |

FOREIGN PATENT DOCUMENTS

| | | |
|---|---|---|
| CN | 104004025 A | 8/2014 |
| CN | 105612238 A | 5/2016 |
| JP | 2003-045662 A | 2/2003 |
| JP | 2009-184987 | 8/2009 |
| JP | 2009-246097 A | 10/2009 |
| JP | 2014-185146 A | 10/2014 |
| KR | 2012-0117693 A | 10/2012 |
| KR | 2013-0135008 A | 12/2013 |
| KR | 2014-0104916 A | 8/2014 |
| KR | 2015-0042387 A | 4/2015 |
| KR | 2015-0122343 A | 11/2015 |
| WO | WO 2013/180376 A1 | 12/2013 |
| WO | WO 2015/053572 A1 | 4/2015 |

OTHER PUBLICATIONS

English language translation of KR 10-2015-0122343, pp. 1-6, Aug. 8, 2017.*
English language translation of KR 10-2012-0117693, pp. 1-32, Aug. 8, 2017.*
International Search Report re Application No. PCT/IB2016/050685, dated May 24, 2016.
Written Opinion re Application No. PCT/IB2016/050685, dated May 24, 2016.
Iinvitation to Pay Additional Fees re Application No. PCT/IB2016/050685, International Searching Authority, dated Mar. 29, 2016.
中国語の為、入力不可, "OLED" document, dated Aug. 31, 2014, pp. 240-242.

* cited by examiner

*Primary Examiner* — Alexander C Kollias
(74) *Attorney, Agent, or Firm* — Husch Blackwell LP

(57) ABSTRACT

A novel organic compound that can be used as an electron-injection material or an electron-transport material of a light-emitting element is provided. An organic compound with which a display device having less crosstalk can be obtained is provided. A light-emitting device, a display device, and an electronic device each having less crosstalk are provided. An organic compound including two or three benzo[h]quinazoline rings is provided. In the organic compound, two or three benzo[h]quinazoline rings are preferably included in the substituent including an aromatic ring or a heteroaromatic ring and having 3 to 30 carbon atoms. When two or three benzo[h]quinazoline rings are included in a substituent particularly including a heteroaromatic ring and having 3 to 30 carbon atoms, a high electron-transport property can be obtained.

21 Claims, 28 Drawing Sheets

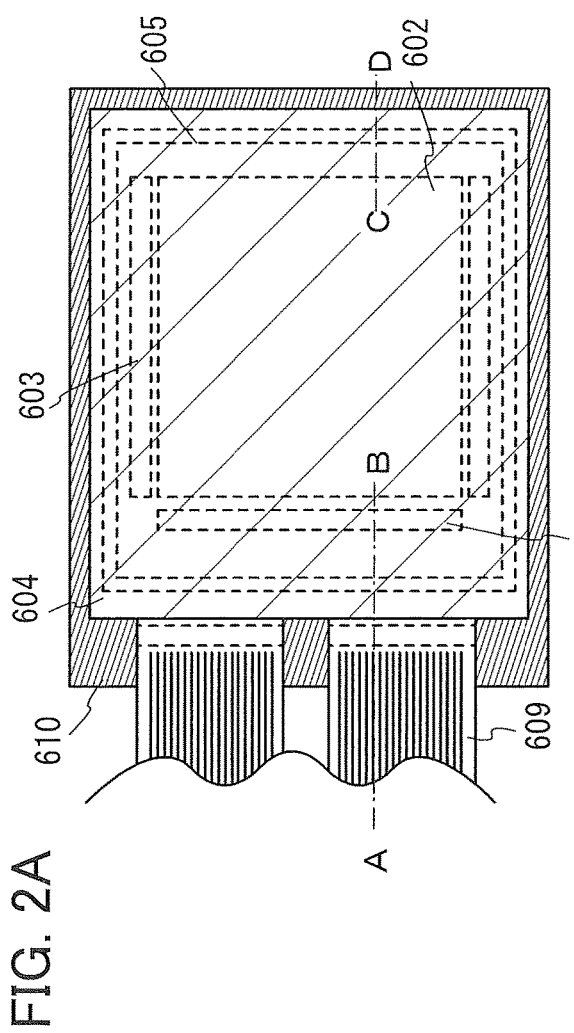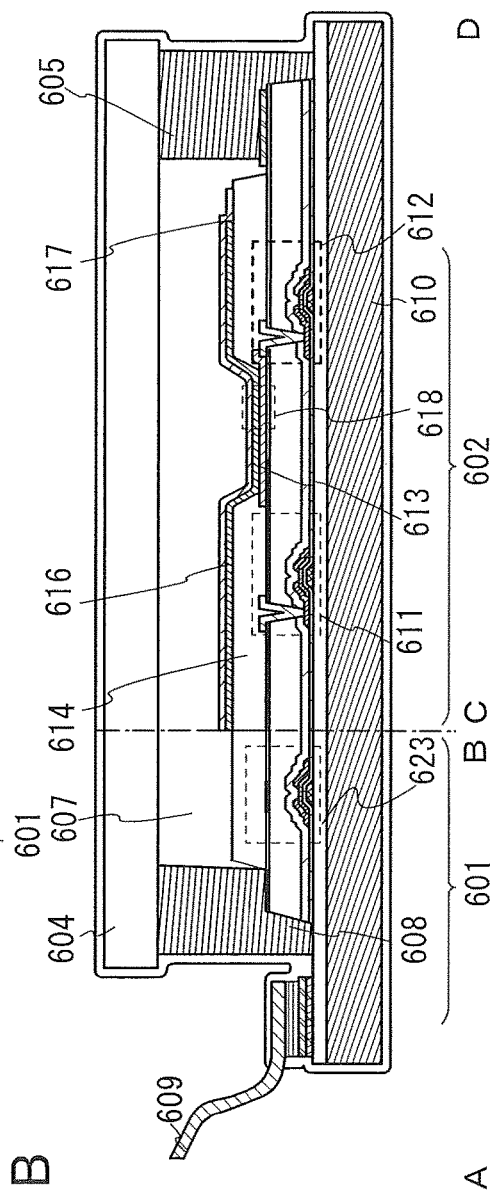

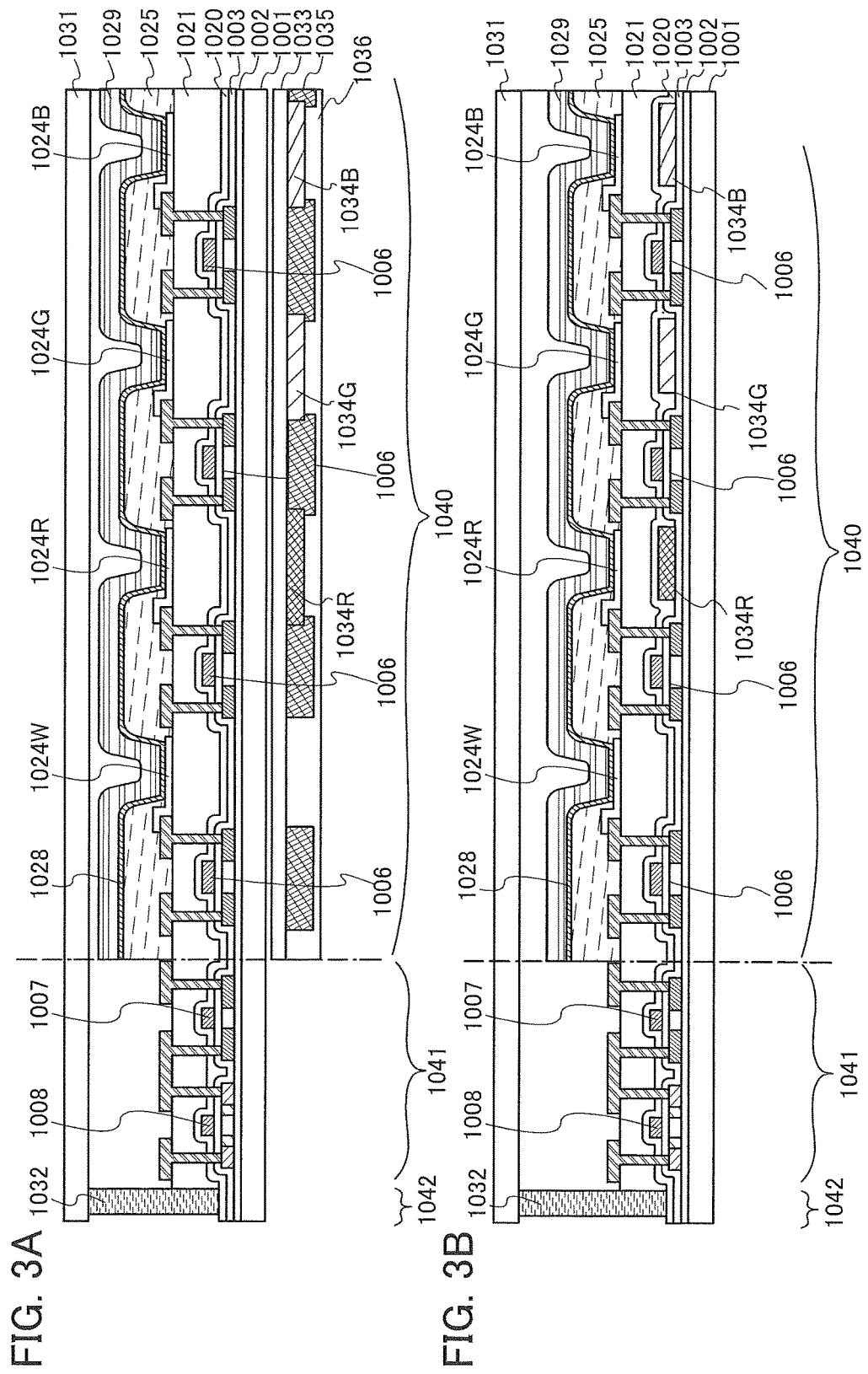

FIG. 7A
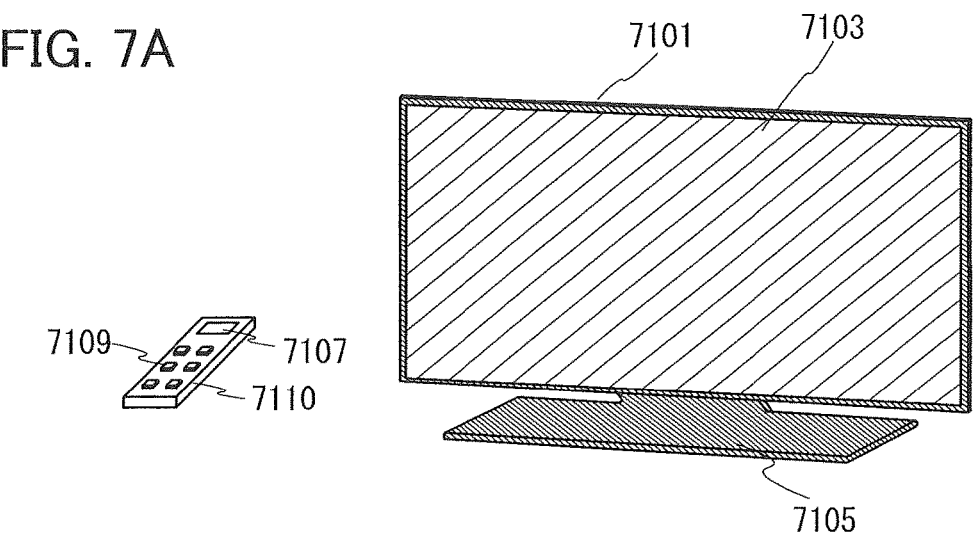
FIG. 7B1
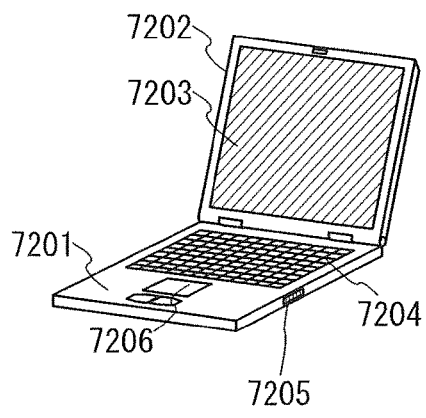
FIG. 7B2
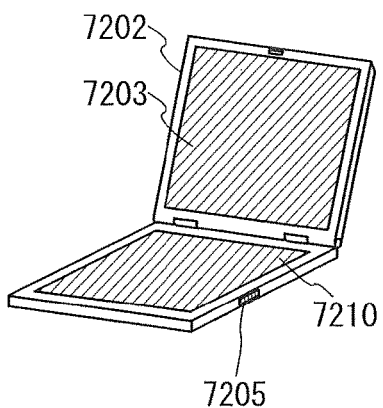
FIG. 7C
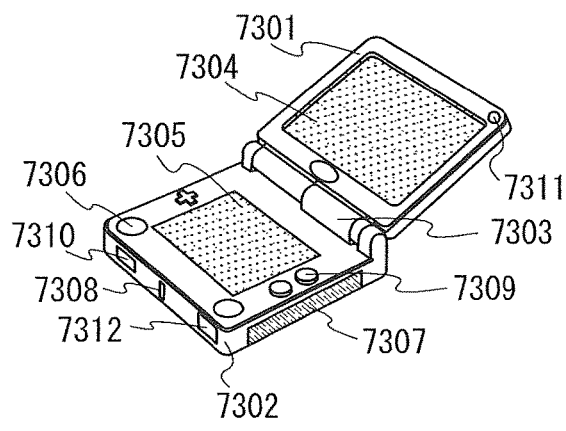
FIG. 7D
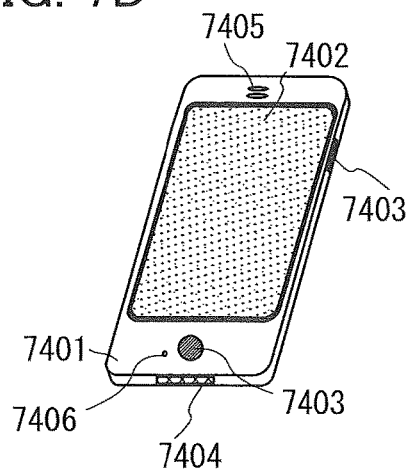

ORGANIC COMPOUND, LIGHT-EMITTING ELEMENT, DISPLAY MODULE, LIGHTING MODULE, LIGHT-EMITTING DEVICE, DISPLAY DEVICE, ELECTRONIC DEVICE, AND LIGHTING DEVICE

TECHNICAL FIELD

One embodiment of the present invention relates to an organic compound and a light-emitting element, a display module, a lighting module, a display device, a light-emitting device, an electronic device, and a lighting device in which the organic compound is used. Note that one embodiment of the present invention is not limited to the above technical field. The technical field of one embodiment of the invention disclosed in this specification and the like relates to an object, a method, or a manufacturing method. In addition, one embodiment of the present invention relates to a process, a machine, manufacture, or a composition of matter. Specifically, examples of the technical field of one embodiment of the present invention disclosed in this specification include a semiconductor device, a display device, a liquid crystal display device, a light-emitting device, a lighting device, a power storage device, a memory device, an imaging device, a method of driving any of them, and a method of manufacturing any of them.

BACKGROUND ART

Light-emitting elements (organic EL elements) including organic compounds and utilizing electroluminescence (EL) have been put to more practical use. In the basic structure of such a light-emitting element, an organic compound layer containing a light-emitting substance (an EL layer) is provided between a pair of electrodes. By voltage application to this element, light emission from the light-emitting substance can be obtained.

Since such light-emitting elements are of self-light-emitting type, light-emitting elements have advantages over liquid crystal displays when used as pixels of a display in that visibility of pixels is high and backlight is not required. Thus, light-emitting elements are suitable as flat panel display elements. A display including such a light-emitting element is also highly advantageous in that it can be thin and lightweight. Besides, very high speed response is one of the features of such an element.

Since light-emitting layers of such light-emitting elements can be successively formed two-dimensionally, planar light emission can be achieved. This feature is difficult to realize with point light sources typified by incandescent lamps and LEDs or linear light sources typified by fluorescent lamps. Thus, light-emitting elements also have great potential as planar light sources, which can be applied to lighting devices and the like.

Although displays or lighting devices including light-emitting elements can be suitably used for a variety of electronic devices as described above, their performance and cost competitiveness have plenty of room to improve. In order to achieve this, materials that have good characteristics and are easily handled are required. There are particularly great demands on heat resistance and reliability such as a lifetime.

Patent Document 1 discloses a pyrimidine- or triazine-based derivative, an electron-transport material containing the same, and an organic electroluminescent element containing the same.

REFERENCE

[Patent Document 1] Japanese Published Patent Application No. 2009-184987

DISCLOSURE OF INVENTION

An object of one embodiment of the present invention is to provide a novel organic compound. An object of another embodiment of the present invention is to provide a novel organic compound that can be used as an electron-transport material of a light-emitting element. An object of another embodiment of the present invention is to provide a novel organic compound that can be used as an electron-injection material of a light-emitting element. An object of another embodiment of the present invention is to provide a novel compound that can be used as an electron-injection material of a light-emitting element and that has high heat resistance. An object of another embodiment of the present invention is to provide an organic compound with which a highly reliable light-emitting element can be manufactured. An object of another embodiment of the present invention is to provide an organic compound with which a light-emitting element having emission efficiency can be manufactured. An object of another embodiment of the present invention is to provide an organic compound with which a display device having less crosstalk can be obtained.

An object of another embodiment of the present invention is to provide a light-emitting device, a display device, and an electronic device each having less crosstalk.

An object of another embodiment of the present invention is to provide a light-emitting element, a display module, a lighting module, a light-emitting device, a display device, and an electronic device each having high reliability. An object of another embodiment of the present invention is to provide a light-emitting element, a display module, a lighting module, a light-emitting device, a display device, and an electronic device each having high display quality. An object of another embodiment of the present invention is to provide a light-emitting element, a display module, a lighting module, a light-emitting device, a display device, and an electronic device each having low power consumption.

It is only necessary that at least one of the above-described objects be achieved in the present invention.

One embodiment of the present invention is an organic compound represented by the following general formula (G1).

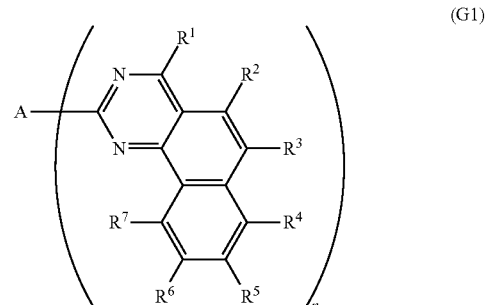

In the general formula (G1), a substituent A represents a substituent including an aromatic ring or a heteroaromatic ring and having 3 to 30 carbon atoms. In addition, each of $R^1$ to $R^7$ independently represents any of hydrogen, an alkyl group having 1 to 6 carbon atoms, and a substituted or unsubstituted aromatic hydrocarbon group having 6 to 13 carbon atoms, and n is 2 or 3.

Another embodiment of the present invention is an organic compound represented by the following general formula (G2).

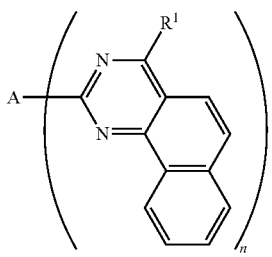

(G2)

In the general formula (G2), a substituent A represents a substituent including an aromatic ring or a heteroaromatic ring and having 3 to 30 carbon atoms. In addition, $R^1$ represents any of hydrogen, an alkyl group having 1 to 6 carbon atoms, and an aromatic hydrocarbon group having 6 to 13 carbon atoms, and n is 2 or 3.

Another embodiment of the present invention is any of the above-described organic compounds, in which n is 2.

Another embodiment of the present invention is an organic compound represented by the following general formula (G3).

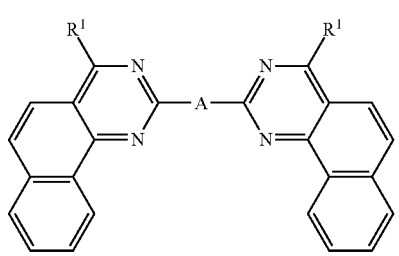

(G3)

In the general formula (G3), a substituent A represents a substituent including an aromatic ring or a heteroaromatic ring and having 3 to 30 carbon atoms. In addition, $R^1$ represents any of hydrogen, an alkyl group having 1 to 6 carbon atoms, and an aromatic hydrocarbon group having 6 to 13 carbon atoms.

Another embodiment of the present invention is any of the above-described organic compounds, in which the substituent A represents a substituent including one or more benzene skeletons or pyridine skeletons and having less than or equal to 30 carbon atoms.

Another embodiment of the present invention is any of the above-described organic compounds, in which the substituent A represents a substituent including one benzene skeleton or one pyridine skeleton and having less than or equal to 30 carbon atoms.

Another embodiment of the present invention is any of the above-described organic compounds, in which the substituent A represents a phenylene group or a pyridine diyl group.

Another embodiment of the present invention is an organic compound represented by the following general formula (G4).

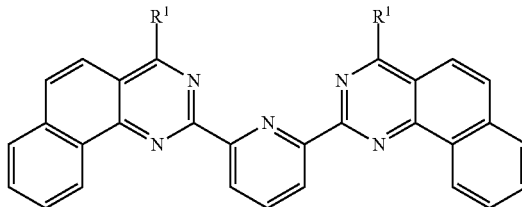

(G4)

In the general formula (G4), $R^1$ represents any of hydrogen, an alkyl group having 1 to 6 carbon atoms, and an aromatic hydrocarbon group having 6 to 13 carbon atoms.

Another embodiment of the present invention is any of the above-described organic compounds, in which $R^1$ represents a phenyl group or a naphthyl group.

Another embodiment of the present invention is a light-emitting element that contains any of the above-described organic compounds.

Another embodiment of the present invention is a light-emitting element that contains any of the above-described organic compounds in an electron-transport layer.

Another embodiment of the present invention is a light-emitting element that contains any of the above-described organic compounds in an electron-injection layer.

Another embodiment of the present invention is a tandem light-emitting element that contains any of the above-described organic compounds.

Another embodiment of the present invention is a light-emitting element that contains any of the above-described organic compounds in a layer in contact with an anode side of a charge-generation layer.

Another embodiment of the present invention is a light-emitting element including an anode, a cathode, and an EL layer between the anode and the cathode. The EL layer includes a plurality of layered regions having different functions. One of the layered regions which is in contact with the cathode includes an organic compound including two or three benzo[h]quinazoline rings.

Another embodiment of the present invention is a light-emitting element including an anode, a cathode, and an EL layer between the anode and the cathode. The EL layer includes at least a light-emitting layer and an electron-injection layer. The electron-injection layer includes an organic compound including two or three benzo[h]quinazoline skeletons.

Another embodiment of the present invention is a light-emitting element including an anode, a cathode, and an EL layer between the anode and the cathode. The EL layer includes at least a light-emitting layer and a charge-generation layer. The charge-generation layer includes an organic compound including two or three benzo[h]quinazoline skeletons.

Another embodiment of the present invention is a light-emitting element including an anode, a cathode, and an EL layer between the anode and the cathode. The EL layer includes at least a light-emitting layer and an electron-transport layer. The electron-transport layer includes an organic compound including two or three benzo[h]quinazoline skeletons.

Another embodiment of the present invention is a light-emitting element having any of the above structures, in which the two or three benzo[h]quinazoline skeletons in the organic compound are bonded to a substituent including an aromatic ring or a heteroaromatic ring and having 3 to 30 carbon atoms.

Another embodiment of the present invention is a light-emitting element having any of the above structures, in which the two or three benzo[h]quinazoline skeletons in the organic compound are bonded to a substituent including a heteroaromatic ring and having 3 to 30 carbon atoms.

Another embodiment of the present invention is a light-emitting element having any of the above structures, in which the two or three benzo[h]quinazoline skeletons in the organic compound are bonded to a pyridine ring.

Another embodiment of the present invention is a light-emitting element having any of the above structures, in which the two benzo[h]quinazoline skeletons in the organic compound are bonded to a pyridine ring.

Another embodiment of the present invention is a light-emitting element having the above structure in which the 2- and 6-positions of the pyridine ring in the organic compound are substituted.

Another embodiment of the present invention is a light-emitting element having any of the above structures, in which the 2-position of the benzo[h]quinazoline skeleton in the organic compound is substituted.

Another embodiment of the present invention is a display module including a light-emitting element having any of the above structures.

Another embodiment of the present invention is a lighting module including a light-emitting element having any of the above structures.

Another embodiment of the present invention is a light-emitting device including the above light-emitting element and a unit for controlling the light-emitting element.

Another embodiment of the present invention is a display device that includes a light-emitting element having any of the above structures in a display portion and a unit for controlling the light-emitting element.

Another embodiment of the present invention is a lighting device including a light-emitting element having any of the above structures in a lighting portion and a unit for controlling the light-emitting element.

Another embodiment of the present invention is an electronic device that includes a light-emitting element having any one of the above structures.

Note that the light-emitting device in this specification includes, in its category, an image display device with a light-emitting element. The light-emitting device may be included in a module in which a light-emitting element is provided with a connector such as an anisotropic conductive film or a tape carrier package (TCP), a module in which a printed wiring board is provided at the end of a TCP, or a module in which an integrated circuit (IC) is directly mounted on a light-emitting element by a chip on glass (COG) method. The light-emitting device may be included in lighting equipment or the like.

One embodiment of the present invention is a novel organic compound. Another embodiment of the present invention is a novel organic compound that can be used as an electron-transport material of a light-emitting element. Another embodiment of the present invention is an organic compound that can be used as an electron-injection material of a light-emitting element. Another embodiment of the present invention is an organic compound that can be used as an electron-injection material of a light-emitting element and that has high heat resistance. Another embodiment of the present invention is an organic compound with which a highly reliable light-emitting element can be manufactured.

Another embodiment of the present invention is an organic compound with which a display device having less crosstalk can be provided.

Another embodiment of the present invention can provide a light-emitting device, a display device, and an electronic device each having less crosstalk.

Another embodiment of the present invention can provide a light-emitting element, a light-emitting device, a display device, and an electronic device each having high reliability. Another embodiment of the present invention can provide a light-emitting device, a display device, and an electronic device each having high display quality. Another embodiment of the present invention can provide a novel organic compound, a novel light-emitting element, a novel display module, a novel lighting module, a novel light-emitting device, a novel display device, a novel electronic device, and a novel lighting device.

Note that the descriptions of these effects do not preclude the existence of other effects. One embodiment of the present invention does not necessarily achieve all the above effects. Other effects will be apparent from and can be derived from the descriptions of the specification, the drawings, the claims, and the like.

BRIEF DESCRIPTION OF DRAWINGS

FIGS. 2A and 2B are schematic diagrams of an active matrix light-emitting device.

FIGS. 3A and 3B are schematic diagrams of an active matrix light-emitting device.

FIGS. 7A, 7B1, 7B2, 7C, and 7D illustrate electronic devices.

BEST MODE FOR CARRYING OUT THE INVENTION

Figure 1A:
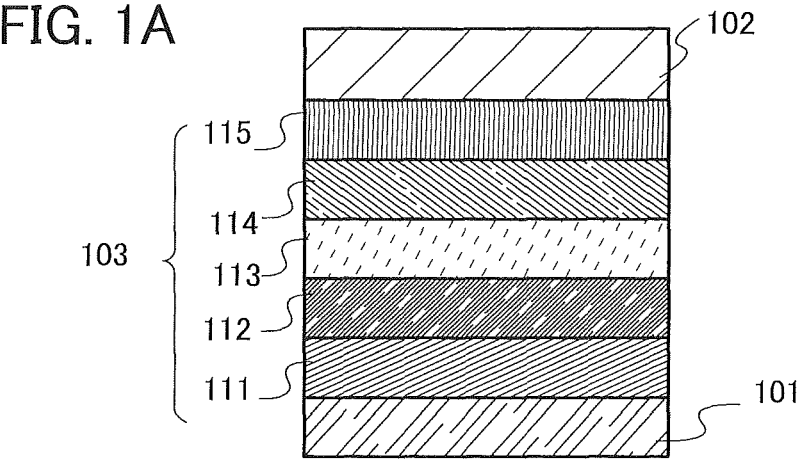
FIGS. 1A to 1C are schematic diagrams of light-emitting elements.

Embodiments of the present invention will be described below in detail with reference to the drawings. Note that the present invention is not limited to the following description, and it will be easily understood by those skilled in the art that various changes and modifications can be made without departing from the spirit and scope of the present invention. Therefore, the present invention should not be construed as being limited to the description in the following embodiments.

Embodiment 1

One embodiment of the present invention is an organic compound including two or three benzo[h]quinazoline rings.

The organic compound with the above-described structure has a favorable carrier-transport property, particularly an excellent electron-transport property. The organic compound is accordingly suitable for a host material or a carrier-transport layer, particularly an electron-transport layer or an electron-injection layer, in a light-emitting element. The organic compound has high heat resistance, with which a highly reliable light-emitting element can be provided.

When a light-emitting element includes a charge-generation layer and the organic compound having the above-described structure in one embodiment of the present invention is used for a layer that is included in an EL layer and in contact with a surface of the charge-generation layer on the anode side, the degree of crosstalk can be reduced, and this makes it easy to provide a display device having high display quality. The charge-generation layer is described in detail in a later description of light-emitting elements.

In the above organic compound, the two or three benzo[h]quinazoline rings are preferably included in the substituent including an aromatic ring or a heteroaromatic ring and having 3 to 30 carbon atoms. Preferably, the two or three benzo[h]quinazoline rings are included in a substituent including a heteroaromatic ring in particular and having 3 to 30 carbon atoms, in which case a high electron-transport property can be obtained.

The heteroaromatic ring having 3 to 30 carbon atoms which is described above is preferably a pyridine ring. The number of the benzo[h]quinazoline rings is preferably two. With such a structure, an appropriate LUMO level in addition to the high electron-transport property can be obtained, leading to a lower voltage. Furthermore, the benzo[h]quinazoline rings, each of which is a rigid structure, are effective in improving heat resistance and capable of reducing crosstalk.

In an organic compound in which two benzo[h]quinazoline rings are bonded to a pyridine ring, the benzo[h]quinazoline rings are preferably bonded to the 2- and 6-positions of the pyridine ring. With such a structure, an appropriate LUMO level in addition to the high electron-transport property can be obtained and the voltage of a light-emitting element can be reduced. In particular, a feature of the organic compound with such a structure is that molecular planarity is likely to be kept and accordingly conjugation can be easily connected, so that the electron-transport property can be improved. In addition, this feature allows the organic compound to more effectively function as a charge-generation layer, leading to low-voltage driving.

The 2-position of a benzo[h]quinazoline ring included in the above organic compound is preferably bonded to another skeleton. With such a structure, an appropriate LUMO level can be obtained and the voltage of a light-emitting element can be reduced. The organic compound in which the two benzo[h]quinazoline rings are bonded to the pyridine ring, in particular, a compound in which the benzo[h]quinazoline rings are bonded to the 2- and 6-positions of the pyridine ring and the 2-position of the benzo[h]quinazoline ring is bonded to the pyridine ring, is easily coordinated to a material having a donor property, such as an alkali metal, an alkaline earth metal, a rare earth metal, or a compound thereof, and can accordingly improve the property of injecting electrons (electron-accepting property) from a cathode or from a later-described p-type layer or acceptor material. Thus, the organic compound is suitable for an electron-injection layer or a charge-generation layer.

These organic compounds corresponding to the embodiments of the present invention can be represented by the following general formulae (G1) to (G4).

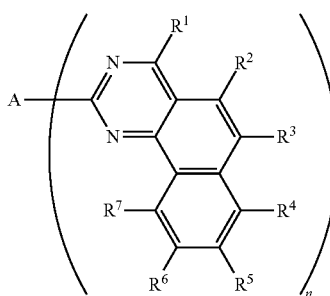

(G1)

In the general formula (G1), a substituent A represents a substituent including an aromatic ring or a heteroaromatic ring and having 3 to 30 carbon atoms. In addition, each of $R^1$ to $R^7$ independently represents any of hydrogen, an alkyl group having 1 to 6 carbon atoms, and a substituted or unsubstituted aromatic hydrocarbon group having 6 to 13 carbon atoms, and n is 2 or 3.

The organic compound represented by the general formula (G1) preferably has a structure where each of $R^2$ to $R^7$ represents hydrogen, in which case the organic compound can be easily synthesized. That is, an organic compound represented by the following general formula (G2) is preferable.

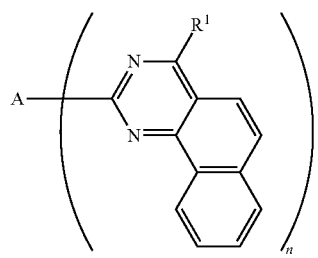

(G2)

In the general formula (G2), a substituent A represents a substituent including an aromatic ring or a heteroaromatic ring and having 3 to 30 carbon atoms. In addition, $R^1$ represents any of hydrogen, an alkyl group having 1 to 6 carbon atoms, and a substituted or unsubstituted aromatic hydrocarbon group having 6 to 13 carbon atoms, and n is 2 or 3.

In the organic compounds represented by the general formulae (G1) and (G2), n is preferably 2. A preferred organic compound is thus represented by the following general formula (G3).

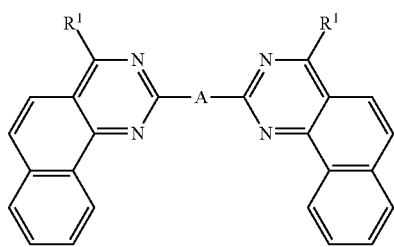

(G3)

In the general formula (G3), a substituent A represents a substituent including an aromatic ring or a heteroaromatic ring and having 3 to 30 carbon atoms. In addition, $R^1$ represents any of hydrogen, an alkyl group having 1 to 6 carbon atoms, and an aromatic hydrocarbon group having 6 to 13 carbon atoms.

In the organic compounds represented by the above general formulae (G1) to (G3), preferably, the substituent A represents a substituent including one or more rings each having a benzene skeleton or one or more pyridine skeletons and having less than or equal to 30 carbon atoms, in which case a high electron-transport property can be obtained. The above substituent having less than or equal to 30 carbon atoms preferably includes one ring having a benzene skeleton or one pyridine skeleton.

In the organic compounds represented by the above general formulae (G1) to (G3), the substituent A preferably represents a phenylene group or a pyridine diyl group. In particular, the substituent A preferably represents a pyridine diyl group, in which case the organic compound has a high electron-transport property and an excellent property of injecting electrons (electron-accepting property) from a cathode or from a later-described p-type layer or acceptor material. Thus, the organic compound is suitable for an electron-injection layer or a charge-generation layer. That is, an organic compound represented by the following general formula (G4) is preferable.

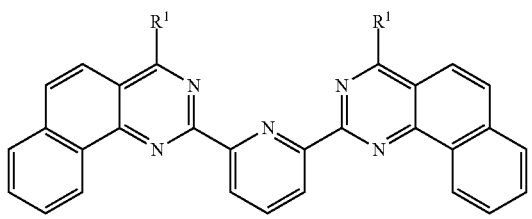

(G4)

In the general formula (G4), $R^1$ represents any of hydrogen, an alkyl group having 1 to 6 carbon atoms, and an aromatic hydrocarbon group having 6 to 13 carbon atoms.

In any of the above organic compounds, $R^1$ preferably represents a phenyl group or a naphthyl group. These groups can improve the stability and thermophysical properties of the organic compound without suppressing the carrier-transport properties, and can also have the effect of reducing crosstalk.

In the above general formulae (G1) to (G4), any of the following can be used as the substituent A: a substituent including one or more rings each having a benzene skeleton; a substituent having one or more pyridine skeletons; a substituent having one or more pyrazine skeletons; a substituent having one or more pyrimidine skeletons; a substituent having one or more pyridazine skeletons; a substituent having one or more triazine skeletons; and the like.

Examples of the substituent that can be preferably used as the substituent A are a phenylene group, a naphthylene group, a pyridinediyl group, a pyrazinediyl group, a pyrimidinediyl group, a pyridazinediyl group, a triazinediyl group, a benzenetriyl group, a triazinetriyl group, and the like. Note that the present invention is not limited to these.

Note that the substituent A may further include a substituent having carbon atoms that are not counted as the above carbon atoms. Examples of such a substituent are an alkyl group having 1 to 6 carbon atoms and a phenyl group.

In addition, each of $R^1$ to $R^7$ independently represents any of hydrogen, an alkyl group having 1 to 6 carbon atoms, and a substituted or unsubstituted aromatic hydrocarbon group having 6 to 13 carbon atoms. Examples of preferable $R^1$ to $R^7$ are hydrogen, a methyl group, an ethyl group, an n-propyl group, an iso-propyl group, an n-butyl group, an iso-butyl group, a sec-butyl group, a tert-butyl group, a pentyl group, a hexyl group, a cyclohexyl group, a phenyl group, a naphthyl group, a fluorenyl group, and the like.

In the case where each of $R^1$ to $R^7$ represents an aromatic hydrocarbon group including a substituent and having 6 to 13 carbon atoms, carbon atoms of the substituent are not counted as the above carbon atoms. Examples of such a substituent are an alkyl group having 1 to 6 carbon atoms and a phenyl group. Specific examples of the alkyl group having 1 to 6 carbon atoms which is used as the substituent include a methyl group, an ethyl group, an n-propyl group, an iso-propyl group, an n-butyl group, an iso-butyl group, a sec-butyl group, a tert-butyl group, a pentyl group, a hexyl group, and a cyclohexyl group.

Note that when the organic compound represented by any of the above general formulae (G1) to (G4) is used for a layer that is included in an EL layer of a light-emitting element having a tandem structure and in contact with the anode side of a charge-generation layer, a display device in which crosstalk is particularly effectively reduced and which has high display quality can be obtained.

Specific examples of the organic compound having the above-described structure include organic compounds listed below.

(100)

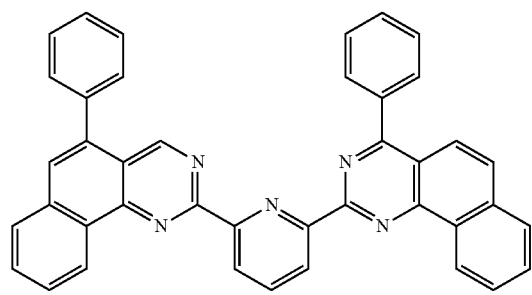

(101)

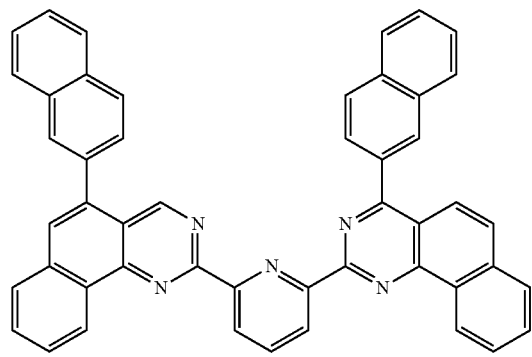

(102)

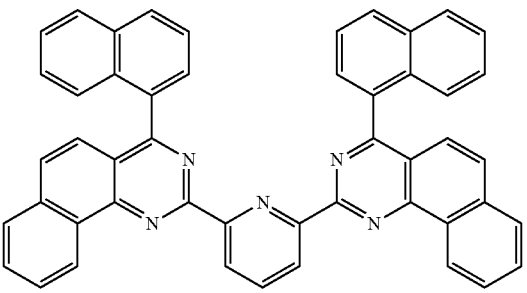

(103)

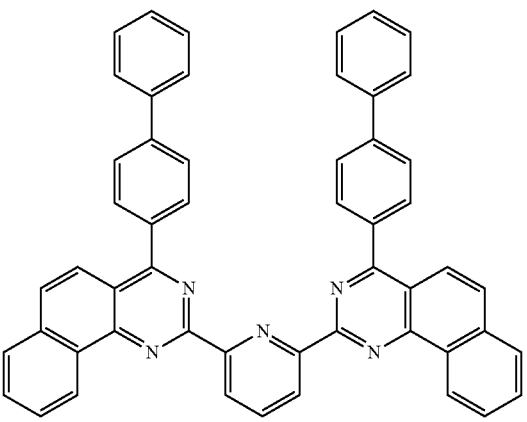

(104)

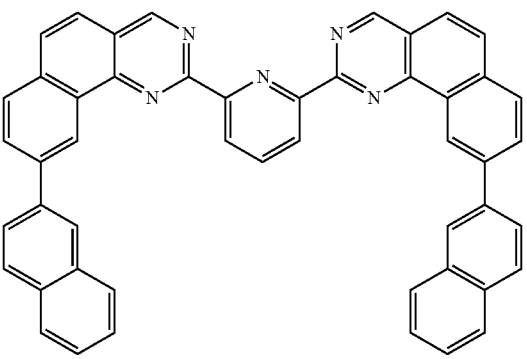

(105)

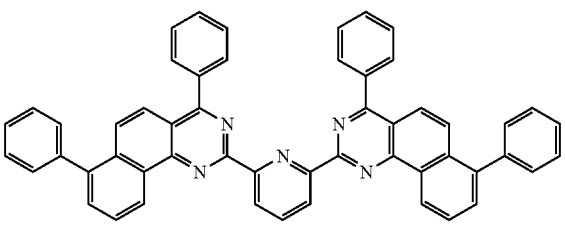

(106)

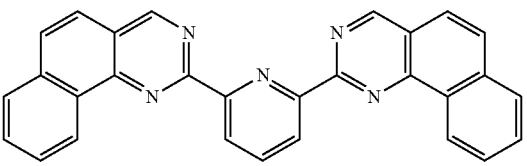

(107)
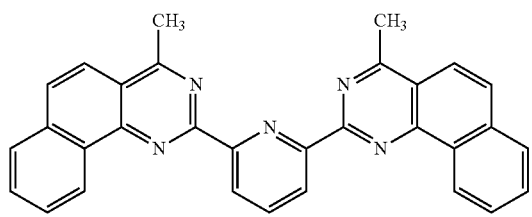
(108)
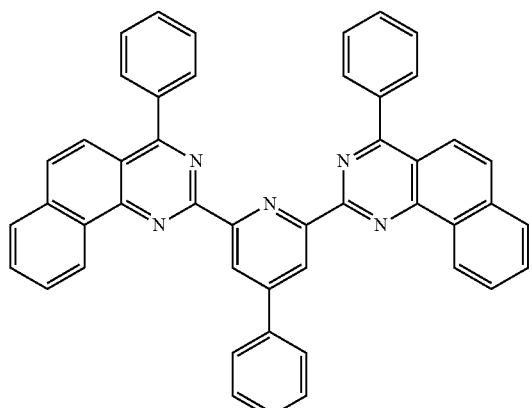
(109)
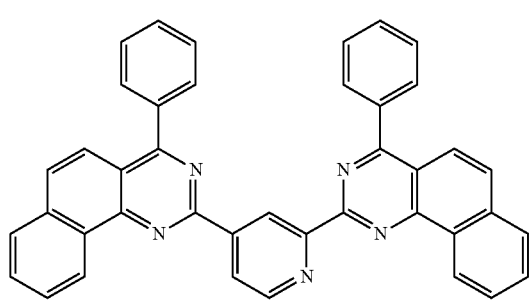
(200)
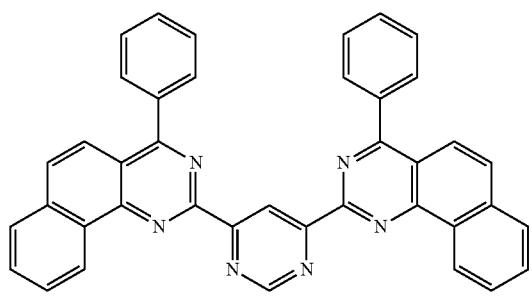
(201)
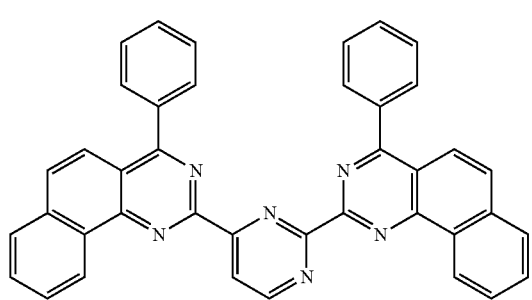
(202)
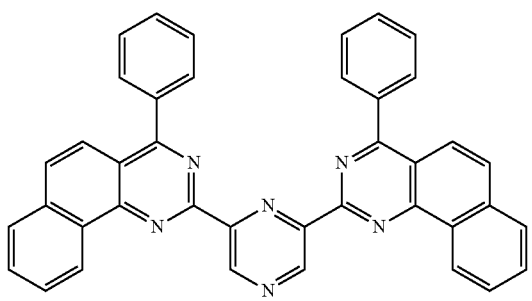
(203)
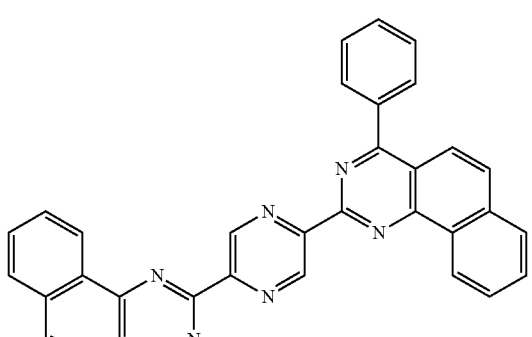
(204)
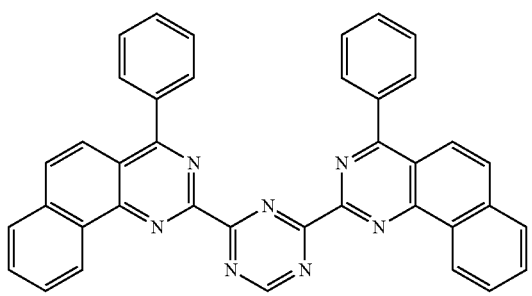
(205)
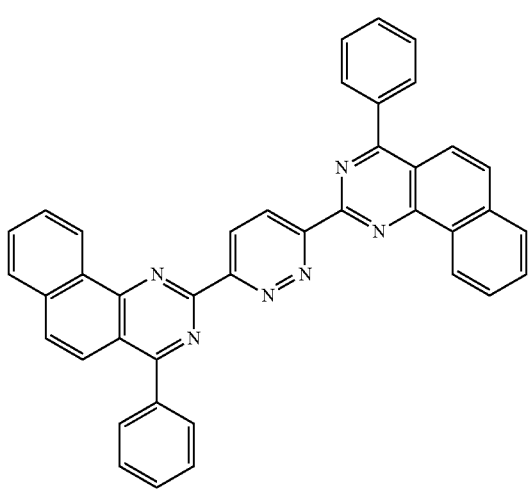

(301)
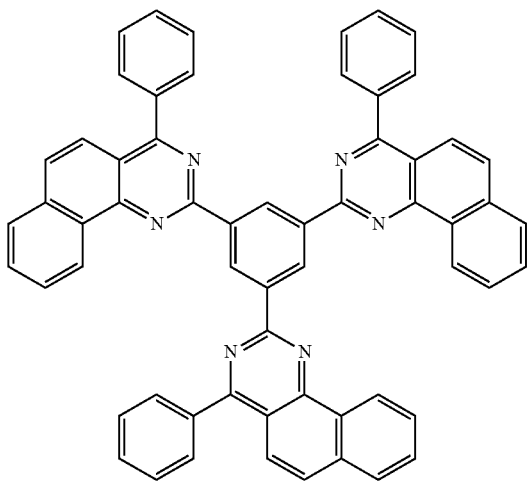
(302)
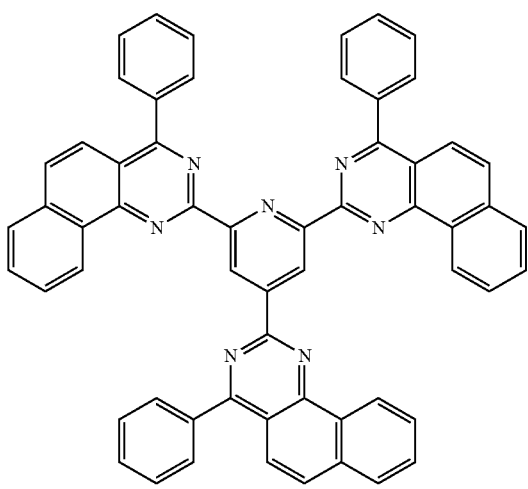
(303)
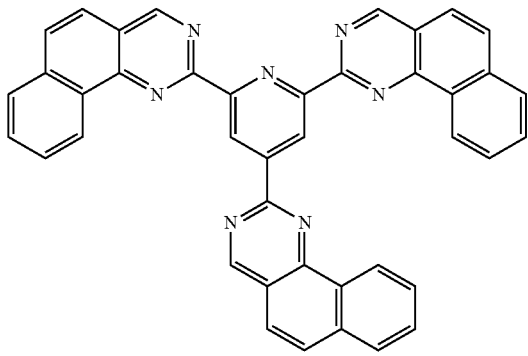
(304)
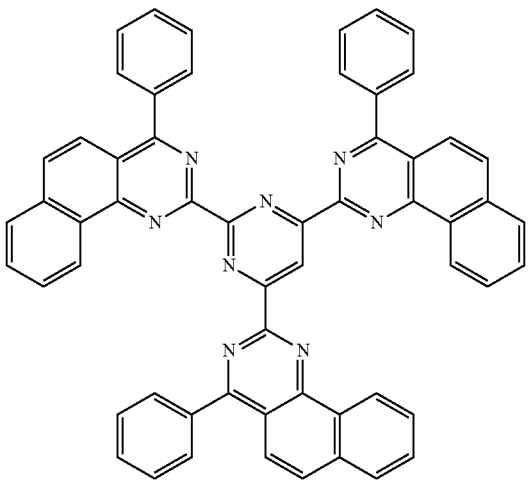
(305)
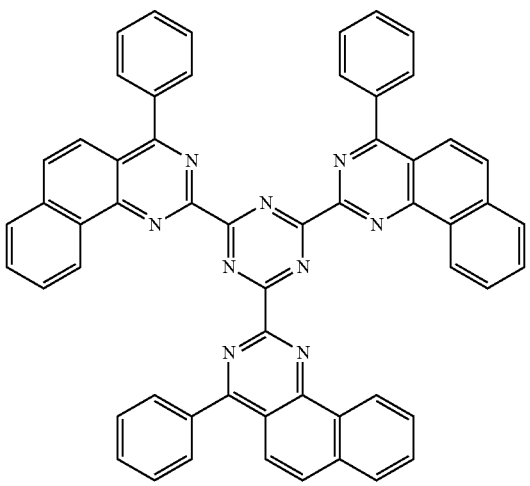
(306)
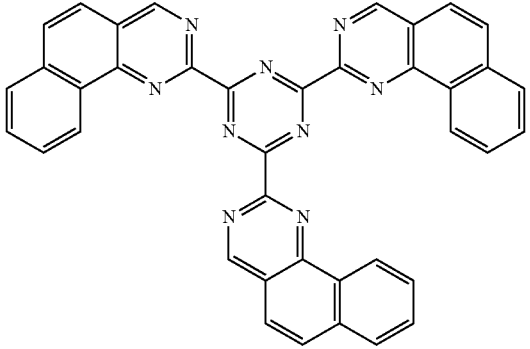

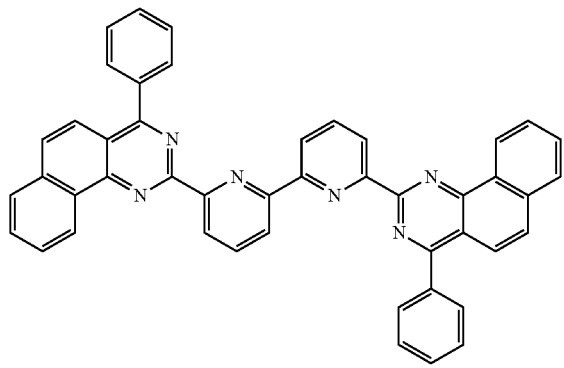
(401)

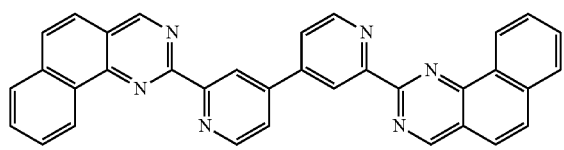
(402)

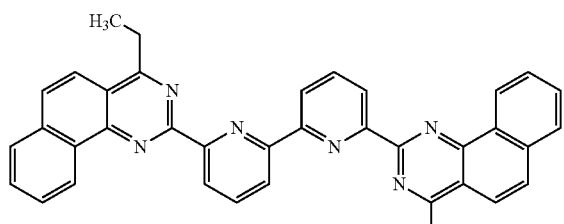
(403)

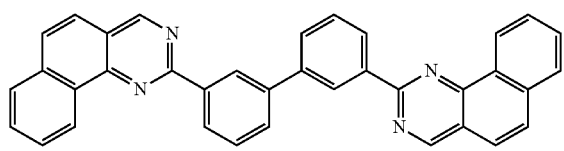
(404)

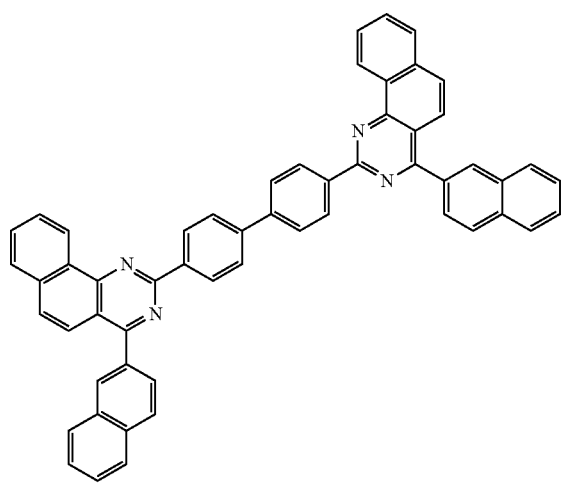
(405)

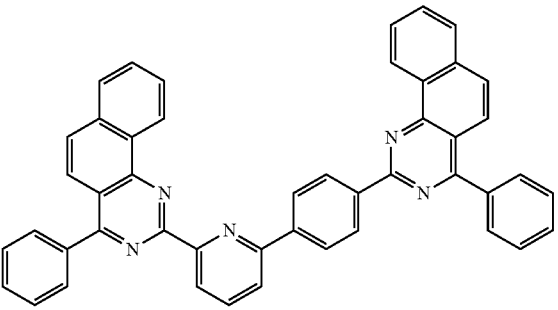
(406)

The organic compound represented by the above general formula (G1), which is typified by the organic compounds represented by such structural formulae, can be synthesized by reaction of an amidine derivative represented by a general formula (G0) with an aldehyde derivative as shown below.

<<Method of Synthesizing Amidine Derivative Represented by General Formula (G0)>>

First, the amidine derivative represented by the general formula (G0) below is synthesized. The amidine derivative represented by the general formula (G0) below can be synthesized by a simple synthesis scheme (A), as shown below. In the scheme (A), an amidine derivative (A1) and a halide of aromatic hydrocarbon (A2), which are raw materials, are coupled to give the amidine derivative represented by the general formula (G0). In the synthesis scheme (A), Q represents a halogen.

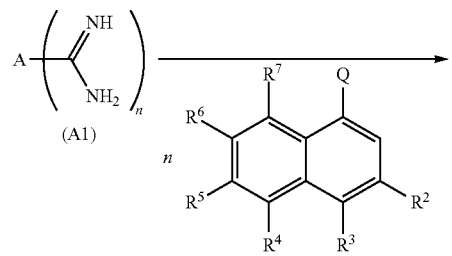
(A)

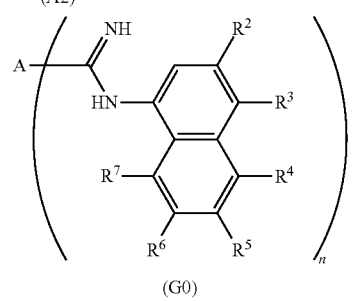
(G0)

In the general formula (G0), the substituent A represents a substituent including an aromatic ring or a heteroaromatic ring and having 3 to 30 carbon atoms. In addition, each of $R^2$ to $R^7$ independently represents any of hydrogen, an alkyl group having 1 to 6 carbon atoms, and an aromatic hydrocarbon group having 6 to 13 carbon atoms, and n is 2 or 3.

Any of the following can be used as the substituent A: a substituent including one or more benzene skeletons; a substituent including one or more pyridine skeletons; a substituent including a pyrazine skeleton; a substituent including one or more pyrimidine skeletons; a substituent including one or more pyridazine skeletons; a substituent including one or more triazine skeletons; and the like. Note that the substituent A may further include a substituent having carbon atoms that are not counted as the above carbon atoms. Examples of such a substituent are an alkyl group having 1 to 6 carbon atoms.

<<Method of Synthesizing Organic Compound Represented by General Formula (G1)>>

Then, the organic compound represented by the general formula (G1) can be synthesized by a simple synthesis scheme (B), as shown below. In the scheme (B), the amidine derivative represented by the general formula (G0) and an aldehyde derivative (A3) are coupled to give the organic compound represented by the general formula (G1). Alternatively, the organic compound may be synthesized via an intermediate (B1). In the case of the synthesis via the intermediate (B1), the intermediate (B1) and a dehydrogenation agent are reacted in an appropriate solvent to give the organic compound represented by the general formula (G1). Examples of the dehydrogenation agent are a benzoquinone derivative, sulfur, and the like.

general formula (G1) can be synthesized. Thus, a feature of the organic compound of one embodiment of the present invention is the abundance of variations.

Although the example of a method of synthesizing the organic compound of one embodiment of the present invention is described above, the present invention is not limited thereto and any other synthesis method may be employed.

Embodiment 2

In this embodiment, a detailed example of the structure of the light-emitting element containing the organic compound described in Embodiment 1 is described below with reference to FIG. 1A.

The light-emitting element in this embodiment includes, between a pair of electrodes, an EL layer including a plurality of layers. Any of the plurality of layers contains the organic compound described in Embodiment 1. In this embodiment, the light-emitting element includes a first electrode 101, a second electrode 102, and an EL layer 103 which is provided between the first electrode 101 and the second electrode 102. Note that in this embodiment, the following description is made on the assumption that the first electrode 101 functions as an anode and that the second electrode 102 functions as a cathode.

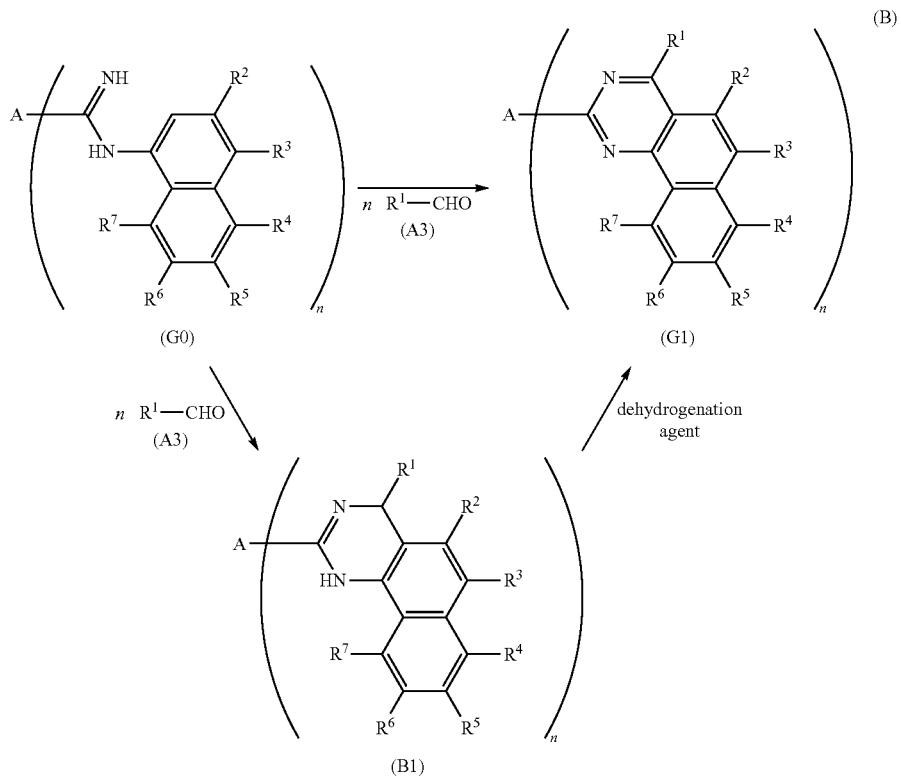

The substituent A, $R^2$ to $R^7$, and n are described for the above synthesis scheme (A) and not again described for the synthesis scheme (B). In the synthesis scheme (B), $R^1$ represents any of hydrogen, an alkyl group having 1 to 6 carbon atoms, and an aromatic hydrocarbon group having 6 to 13 carbon atoms.

Since a wide variety of compounds (A1), (A2), and (A3) used in the synthesis scheme (A) and the synthesis scheme (B) are commercially available or their synthesis is feasible, a great variety of the organic compounds represented by the Since the first electrode 101 functions as the anode, the first electrode 101 is preferably formed using any of metals, alloys, electrically conductive compounds, and mixtures thereof which have a high work function (specifically, a work function of 4.0 eV or more) or the like. Specifically, for example, indium oxide-tin oxide (ITO: indium tin oxide), indium oxide-tin oxide containing silicon or silicon oxide, indium oxide-zinc oxide, indium oxide containing tungsten oxide and zinc oxide (IWZO), and the like can be given. Films of these electrically conductive metal oxides are usually formed by a sputtering method but may be formed by application of a sol-gel method or the like. In an example of the formation method, a film of indium oxide-zinc oxide is formed by a sputtering method using a target in which 1 wt % to 20 wt % of zinc oxide is added to indium oxide. Furthermore, a film of indium oxide containing tungsten oxide and zinc oxide (IWZO) can be formed by a sputtering method using a target in which tungsten oxide and zinc oxide are added to indium oxide at 0.5 wt % to 5 wt % and 0.1 wt % to 1 wt %, respectively. Besides, gold (Au), platinum (Pt), nickel (Ni), tungsten (W), chromium (Cr), molybdenum (Mo), iron (Fe), cobalt (Co), copper (Cu), palladium (Pd), nitrides of metal materials (e.g., titanium nitride), and the like can be given. Graphene can also be used. Note that when a composite material described later is used for a layer which is in contact with the first electrode 101 in the EL layer 103, an electrode material can be selected regardless of its work function.

Figure 1B:
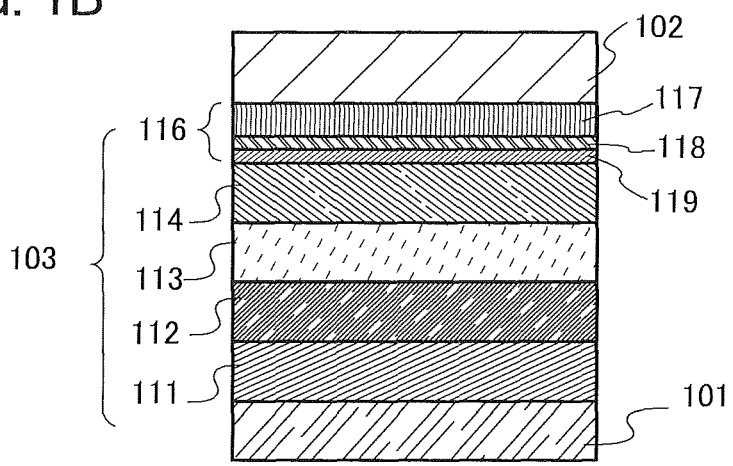

There is no particular limitation on the stacked-layer structure of the EL layer 103 as long as the organic compound described in Embodiment 1 is contained in any of the stacked layers. For example, the EL layer 103 can be formed by combining a hole-injection layer, a hole-transport layer, a light-emitting layer, an electron-transport layer, an electron-injection layer, a carrier-blocking layer, a charge-generation layer, and the like as appropriate. In this embodiment, the EL layer 103 has either of the following two structures: a structure in which a hole-injection layer 111, a hole-transport layer 112, a light-emitting layer 113, an electron-transport layer 114, and an electron-injection layer 115 are stacked in this order over the first electrode 101, as illustrated in FIG. 1A; and a structure in which the hole-injection layer 111, the hole-transport layer 112, the light-emitting layer 113, the electron-transport layer 114, and a charge-generation layer 116 are stacked over the first electrode 101, as illustrated in FIG. 1B. As a host material of the light-emitting layer or as a material of the electron-transport layer or the electron-injection layer, the organic compound described in Embodiment 1 is preferably used; however, one embodiment of the present invention is not limited thereto. Specific examples of materials used for the layers are given below.

The hole-injection layer 111 contains a substance having a high hole-injection property. Molybdenum oxide, vanadium oxide, ruthenium oxide, tungsten oxide, manganese oxide, or the like can be used. Alternatively, the hole-injection layer 111 can be formed using a phthalocyanine-based compound such as phthalocyanine (abbreviation: $H_2Pc$) and copper phthalocyanine (CuPc), an aromatic amine compound such as 4,4'-bis[N-(4-diphenylaminophenyl)-N-phenylamino]biphenyl (abbreviation: DPAB) and {4-[bis(3-methylphenyl)amino]phenyl}-N,N'-diphenyl-(1,1'-biphenyl)-4,4'-diamine (abbreviation: DNTPD), or a high molecular compound such as poly(3,4-ethylenedioxythiophene)/poly(styrenesulfonic acid) (PEDOT/PSS).

Alternatively, a composite material in which a substance having a hole-transport property contains a substance having an acceptor property can be used for the hole-injection layer 111. Note that the use of such a substance having a hole-transport property which contains a substance having an acceptor property enables selection of a material used to form an electrode regardless of its work function. In other words, besides a material having a high work function, a material having a low work function can also be used for the first electrode 101. Examples of the substance having an acceptor property include compounds having an electron-withdrawing group (a halogen group or a cyano group) such as 7,7,8,8-tetracyano-2,3,5,6-tetrafluoroquinodimethane (abbreviation: $F_4$-TCNQ), chloranil, and 2,3,6,7,10,11-hexacyano-1,4,5,8,9,12-hexaazatriphenylene (HAT-CN). In particular, a compound in which electron-withdrawing groups are bonded to a condensed aromatic ring having a plurality of hetero atoms, like HAT-CN, is thermally stable and preferable. In addition, transition metal oxides can be given. Oxides of the metals that belong to Groups 4 to 8 of the periodic table can be given. Specifically, vanadium oxide, niobium oxide, tantalum oxide, chromium oxide, molybdenum oxide, tungsten oxide, manganese oxide, and rhenium oxide are preferable in that their electron-accepting property is high. Among these oxides, molybdenum oxide is particularly preferable in that it is stable in the air, has a low hygroscopic property, and is easy to handle.

As the substance having a hole-transport property which is used for the composite material, any of a variety of organic compounds such as aromatic amine compounds, carbazole derivatives, aromatic hydrocarbons, and high molecular compounds (e.g., oligomers, dendrimers, or polymers) can be used. Note that the organic compound used for the composite material is preferably an organic compound having a high hole-transport property. Specifically, a substance having a hole mobility of $10^{-6}$ $cm^2/Vs$ or more is preferably used. Organic compounds that can be used as the substance having a hole-transport property in the composite material are specifically given below.

Examples of the aromatic amine compounds are N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), 1,3,5-tris[N-(4-diphenylaminophenyl)-N-phenylamino]benzene (abbreviation: DPA3B), and the like.

Examples of carbazole derivatives that can be used for the composite material are 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Other examples of carbazole derivatives that can be used for the composite material are 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthracenyl)phenyl]-9H-carbazole (abbreviation: CzPA), 1,4-bis[4-(N-carbazolyl)phenyl]-2,3,5,6-tetraphenylbenzene, and the like.

Examples of aromatic hydrocarbons that can be used for the composite material are 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-b is [2-(1-naphthyl)phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Besides, pentacene, coronene, or the like can also be used. The aromatic hydrocarbon which has a hole mobility of 1×10$^{-6}$ cm$^2$/Vs or more and which has 14 to 42 carbon atoms is particularly preferable.

Note that the aromatic hydrocarbons that can be used for the composite material may have a vinyl skeleton. Examples of the aromatic hydrocarbon having a vinyl group are 4,4'-bis(2,2-diphenylvinyl)biphenyl (abbreviation: DPVBi) and 9,10-bis[4-(2,2-diphenylvinyl)phenyl]anthracene (abbreviation: DPVPA).

A high molecular compound such as poly(N-vinylcarbazole) (abbreviation: PVK), poly(4-vinyltriphenylamine) (abbreviation: PVTPA), poly[N-(4-{N'-[4-(4-diphenylamino) phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

By providing a hole-injection layer, a high hole-injection property can be achieved to allow a light-emitting element to be driven at a low voltage.

Note that the hole-injection layer may be formed of the above-described acceptor material alone or of the above-described acceptor material and another material in combination. In this case, the acceptor material extracts electrons from the hole-transport layer, so that holes can be injected into the hole-transport layer. The acceptor material transfers the extracted electrons to the anode.

The hole-transport layer 112 contains a substance having a hole-transport property. Examples of the substance having a hole-transport property are aromatic amine compounds such as 4,4'-bis[N-(1-naphthyl)-N-phenylamino]biphenyl (abbreviation: NPB), N,N'-bis(3-methylphenyl)-N,N-diphenyl-[1,1'-biphenyl]-4,4'-diamine (abbreviation: TPD), 4,4',4"-tris(N,N-diphenylamino)triphenylamine (abbreviation: TDATA), 4,4',4"-tris[N-(3-methylphenyl)-N-phenylamino] triphenylamine (abbreviation: MTDATA), 4,4'-bis[N-(spiro-9,9'-bifluoren-2-yl)-N-phenylamino]biphenyl (abbreviation: BSPB), and 4-phenyl-4'-(9-phenylfluoren-9-yl)triphenylamine (abbreviation: BPAFLP). The substances mentioned here have a high hole-transport property and are mainly ones that have a hole mobility of 10$^{-6}$ cm$^2$/Vs or more. An organic compound given as an example of the substance having a hole-transport property in the composite material described above can also be used for the hole-transport layer 112. A high molecular compound such as poly(N-vinylcarbazole) (abbreviation: PVK) and poly(4-vinyltriphenylamine) (abbreviation: PVTPA) can also be used. Note that the layer that contains the substance having a hole-transport property is not limited to a single layer, and may be a stack of two or more layers including any of the above substances.

The light-emitting layer 113 may be a layer that contains a fluorescent substance and emits fluorescence, a layer that contains a phosphorescent substance and emits phosphorescence, or a layer that contains a substance emitting thermally activated delayed fluorescence (TADF) and emits TADF. Furthermore, the light-emitting layer 113 may be a single layer or include a plurality of layers containing different light-emitting substances.

Examples of materials that can be used as the fluorescent substance in the light-emitting layer 113 are as follows. Other various fluorescent substances can also be used.

The examples include 5,6-bis[4-(10-phenyl-9-anthryl) phenyl]-2,2'-bipyridine (abbreviation: PAP2BPy), 5,6-bis [4'-(10-phenyl-9-anthryl)biphenyl-4-yl]-2,2'-bipyridine (abbreviation: PAPP2BPy), N,N'-bis[4-(9-phenyl-9H-fluoren-9-yl)phenyl]-N,N'-diphenyl-pyrene-1,6-diamine (abbreviation: 1,6FLPAPrn), N,N'-bis(3-methylphenyl)-N,N'-bis[3-(9-phenyl-9H-fluoren-9-yl)phenyl]-pyrene-1,6-diamine (abbreviation: 1,6mMemFLPAPm), N,N'-bis[4-(9H-carbazol-9-yl)phenyl]-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N"-(2-tert-butylanthracene-9,10-diyldi-4,1-phenylene)bis [N,N',N"-triphenyl-1,4-phenylenedia mine] (abbreviation: DPABPA), N,9-diphenyl-N-[4-(9,10-diphenyl-2-anthryl) phenyl]-9H-carbazol-3-amine (abbreviation: 2PCAPPA), N-[4-(9,10-diphenyl-2-anthryl)phenyl]-N, N',N"-triphenyl-1,4-phenylenediamine (abbreviation: 2DPAPPA), N,N,N', N',N",N",N"',N"'-octaphenyldibenzo[g,p]chrysene-2,7,10, 15-tetraamine (abbreviation: DBC1), coumarin 30, N-(9,10-diphenyl-2-anthryl)-N9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N,N'-triphenyl-1,4-phenylenediamine (abbreviation: 2DPAPA), N-[9, 10-bis(1,1'-biphenyl-2-yl)-2-anthryl]-N,N',N'-triphenyl-1,4-phenylenediamine (abbreviation: 2DPABPhA), 9,10-bis(1, 1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylide ne}propanedinitrile (abbreviation: DCM2), N,N,N',N'-tetrakis(4-methylphenyl) tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethe nyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethe nyl]-4H-pyran-4-ylidene}propanedinitrile (abbreviation: DCJTB), 2-(2,6-bis {2-[4-(dimethylamino)phenyl]ethenyl}-4H-pyran-4-ylidene)propanedinitrile (abbreviation: BisDCM), and 2-{2, 6-bis[2-(8-methoxy-1,1,7,7-tetramethyl-2,3,6,7-tetrahydro-1H,5H-benzo[ij]quinolizin-9-yl) ethenyl]-4H-pyran-4-ylidene}propanedinitrile (abbreviation: BisDCJTM). Condensed aromatic diamine compounds typified by pyrenediamine compounds such as 1,6FLPAPrn and 1,6mMemFLPAPrn are particularly preferable because of their moderate hole-trapping property, high emission efficiency, and high reliability.

Examples of materials that can be used as the phosphorescent substance in the light-emitting layer 113 are as follows.

The examples include organometallic iridium complexes having 4H-triazole skeletons, such as tris {2-[5-(2-methylphenyl)-4-(2,6-dimethylphenyl)-4H-1, 2,4-triazol-3-yl-κN2]phenyl-κC}iridiu m(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato] iridium(III) (abbreviation: [Ir(iPrptz-3b)$_3$]); organometallic iridium complexes having 1H-triazole skeletons, such as tris[3-methyl-1-(2-methylphenyl)-5-phenyl-1H-1,2,4-triazolato]iridium(III) (abbreviation: [Ir(Mptz1-mp)$_3$]) and tris (1-methyl-5-phenyl-3-propyl-1H-1,2,4-triazolato)iridium (III) (abbreviation: [Ir(Prptz1-Me)$_3$]); organometallic iridium complexes having imidazole skeletons, such as fac-tris[1-(2,6-diisopropylphenyl)-2-phenyl-1H-imidazole] iridium(III) (abbreviation: [Ir(iPrpmi)$_3$]) and tris[3-(2,6-dimethylphenyl)-7-methylimidazo[1,2-j]phenanthridinato] iridium(III) (abbreviation: [Ir(dmpimpt-Me)$_3$]); and organometallic iridium complexes in which aphenylpyridine derivative having an electron-withdrawing group is a ligand, such as bis[2-(4',6'-difluorophenyl)pyridinato-N,C$^{2'}$]iridium (III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl) phenyl]pyridinato-N,C$^{2'}$}iridium(III) picolinate (abbreviation: [Ir(CF$_3$ppy)$_2$(pic)]), and bis[2-(4',6'-difluorophenyl)pyridinato-N,C$^{2'}$]iridium(III) acetylacetonate (abbreviation: FIr(acac)). These are compounds emitting blue phosphorescence and have an emission peak at 440 nm to 520 nm.

Other examples include organometallic iridium complexes having pyrimidine skeletons, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(Ill) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato) bis(4,6-diphenylpyrimidinato)iridium(III) (abbreviation: [Ir (dppm)$_2$(acac)]); organometallic iridium complexes having pyrazine skeletons, such as (acetylacetonato)bis(3,5-dimethyl-2-phenylpyrazinato)iridium(Ill) (abbreviation: [Ir (mppr-Me)$_2$(acac)]) and (acetylacetonato)bis(5-isopropyl-3-methyl-2-phenylpyrazinato)iridium(III) (abbreviation: [Ir (mppr-iPr)$_2$(acac)]); organometallic iridium complexes having pyridine skeletons, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo [h]quinolinato)iridium(III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and rare earth metal complexes such as tris(acetylacetonato)(monophenanthroline)terbium(III) (abbreviation: [Tb(acac)$_3$ (Phen)]). These are mainly compounds emitting green phosphorescence and have an emission peak at 500 nm to 600 nm. Note that organometallic iridium complexes having pyrimidine skeletons have distinctively high reliability and emission efficiency and thus are especially preferable.

Other examples include organometallic iridium complexes having pyrimidine skeletons, such as (diisobutyrylmethanato)bis[4,6-bis(3-methylphenyl)pyrimidinato] iridium(III) (abbreviation: [Ir(5mdppm)$_2$(dibm)]), bis[4,6-bis(3-methylphenyl)pyrimidinato](dipivaloylmethanato) iridium(III) (abbreviation: [Ir(5mdppm)$_2$(dpm)]), bis[4,6-di (naphthalen-1-yl)pyrimidinato](dipivaloyhnethanato) iridium(III) (abbreviation: [Ir(d1npm)$_2$(dpm)]); organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having pyridine skeletons, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); platinum complexes such as 2,3,7,8,12,13,17,18-octaethyl-21H,23H-porphyrin platinum (II) (abbreviation: PtOEP); and rare earth metal complexes such as tris(1,3-diphenyl-1,3-propanedionato)(monophenanthroline)europium(III) (abbreviation: [Eu(DBM)$_3$ (Phen)]) and tris[1-(2-thenoyl)-3,3,3-trifluoroacetonato] (monophenanthroline)europium(III) (abbreviation: [Eu (TTA)$_3$(Phen)]). These are compounds emitting red phosphorescence and have an emission peak at 600 nm to 700 nm. Furthermore, organometallic iridium complexes having pyrazine skeletons can provide red light emission with favorable chromaticity.

As well as the above phosphorescent compounds, known phosphorescent materials may be selected and used.

Examples of the TADF material include a fullerene, a derivative thereof, an acridine derivative such as proflavine, eosin, or the like, and a metal-containing porphyrin such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)), which are shown in the following structural formulae.

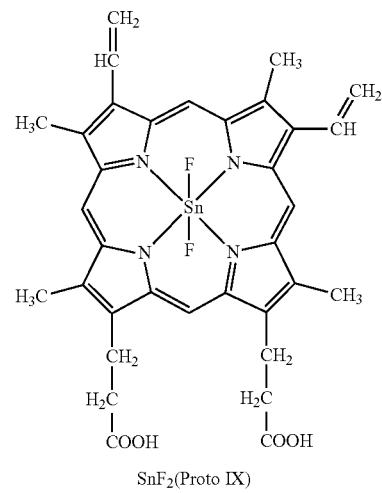

SnF$_2$(Proto IX)

-continued

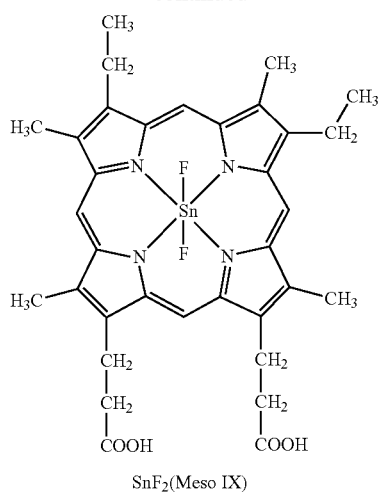
SnF₂(Meso IX)

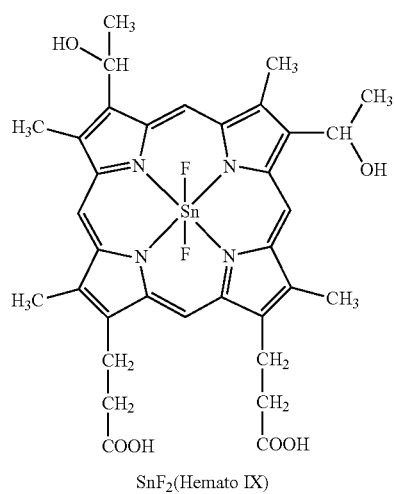
SnF₂(Hemato IX)

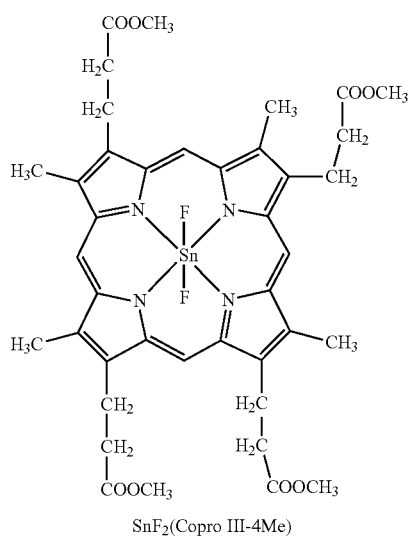
SnF₂(Copro III-4Me)

-continued

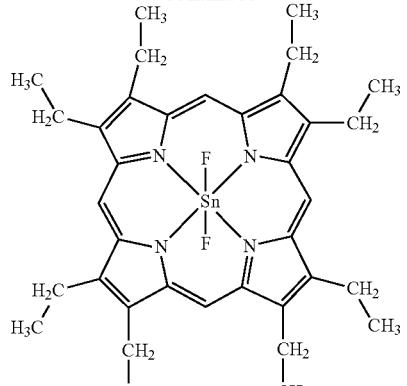
SnF₂(OEP)

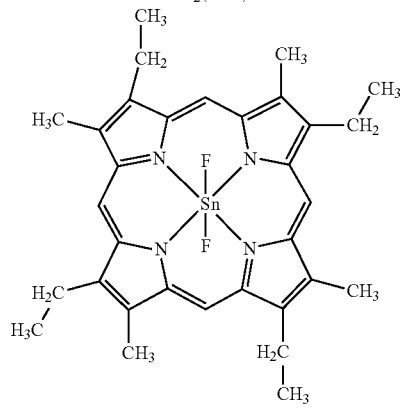
SnF₂(Etio I)

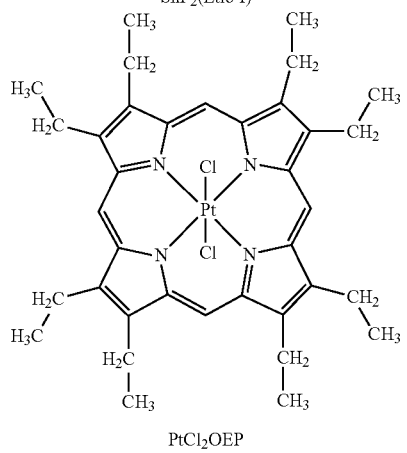
PtCl₂OEP

Alternatively, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (PIC-TRZ) shown in the following structural formula, can be used. The heterocyclic compound is preferably used because of the π-electron rich heteroaromatic ring and the π-electron deficient heteroaromatic ring, for which the electron-transport property and the hole-transport property are high. Note that a substance in which the π-electron rich heteroaromatic ring is directly bonded to the π-electron deficient heteroaromatic ring is particularly preferably used because the donor property of the π-electron rich heteroaromatic ring and the acceptor property of the π-electron deficient heteroaromatic ring are both increased and the energy difference between the $S_1$ level and the $T_1$ level becomes small.

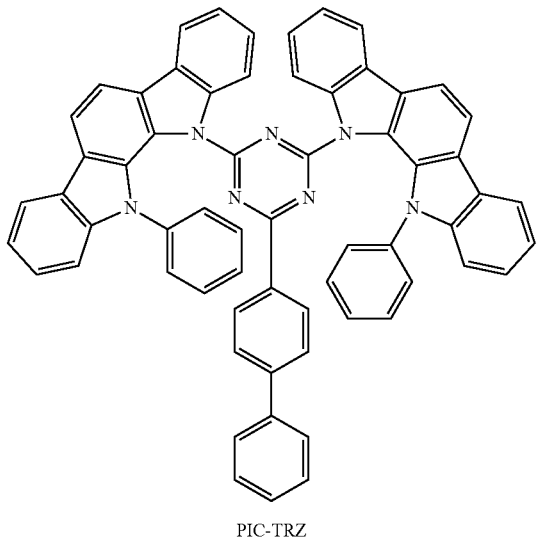 [SMILES: c1ccc(-c2ccc(-c3nc(-n4c5ccccc5c5ccc6c7ccccc7n(-c7ccccc7)c6c54)nc(-n4c5ccccc5c5ccc6c7ccccc7n(-c7ccccc7)c6c54)n3)cc2)cc1]

PIC-TRZ

A variety of carrier-transport materials can be used as the host material of the light-emitting layer. As the carrier-transport material, any of substances having a hole-transport property and substances having an electron-transport property listed below and the like can be used. It is needless to say that it is possible to use a material having a hole-transport property, a material having an electron-transport property, or a bipolar material other than the substances listed below.

The following are examples of materials having a hole-transport property: compounds having aromatic amine skeletons, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having carbazole skeletons, such as 1,3-bis(N-carbazolyObenzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having thiophene skeletons, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having furan skeletons, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above materials, the compounds having aromatic amine skeletons and the compounds having carbazole skeletons are preferred because these compounds are highly reliable and have a high hole-transport property and contribute to a reduction in drive voltage.

The following are examples of materials having an electron-transport property: the organic compound described in Embodiment 1; metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc (II) (abbreviation: ZnPBO), and bis[2-(2-benzothiazolyl)phenolato]zinc(II) (abbreviation: ZnBTZ); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II); and heterocyclic compounds having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, the heterocyclic compounds having diazine skeletons and the heterocyclic compounds having pyridine skeletons are highly reliable and preferred. In particular, the heterocyclic compounds having diazine (pyrimidine or pyrazine) skeletons have a high electron-transport property and contribute to a decrease in drive voltage.

Note that the host material may be a mixture of a plurality of kinds of substances, and in the case of using a mixed host material, it is preferable to mix a material having an electron-transport property with a material having a hole-transport property. By mixing the material having an electron-transport property with the material having a hole-transport property, the transport property of the light-emitting layer 113 can be easily adjusted and a recombination region can be easily controlled. The ratio of the content of the material having a hole-transport property to the content of the material having an electron-transport property may be 1:9 to 9:1.

An exciplex may be formed by these mixed materials. When these mixed materials are selected so as to form an exciplex that exhibits light emission whose wavelength overlaps with the wavelength of a lowest-energy-side absorption band of the light-emitting material, energy can be transferred smoothly and light emission can be obtained efficiently. In addition, such a combination is preferable because the use of the exciplex for the energy transfer leads to a lower drive voltage.

The light-emitting layer 113 having the above-described structure can be formed by co-evaporation by a vacuum evaporation method, or a gravure printing method, an offset printing method, an inkjet method, a spin coating method, a dip coating method, or the like using a mixed solution.

The electron-transport layer 114 contains a substance having an electron-transport property. As the substance having an electron-transport property, it is possible to use any of the above-listed substances having an electron-transport property that can be used as a host material. The organic compound of one embodiment of the present invention which is described in Embodiment 1 can be suitably used. It is particularly preferable that the organic compound of the present invention be contained in a portion of the electron-transport layer 114 in contact with the electron-injection layer 115 because the reliability of the light-emitting element can be improved.

Between the electron-transport layer 114 and the light-emitting layer 113, a layer that controls transport of electron carriers may be provided. This is a layer formed by addition of a small amount of a substance having an electron-trapping property to the aforementioned materials having an electron-transport property, and the layer is capable of adjusting carrier balance by retarding transport of electron carriers. Such a structure is very effective in preventing a problem (such as a reduction in element lifetime) caused when electrons pass through the light-emitting layer.

In addition, the electron-injection layer 115 may be provided in contact with the second electrode 102 between the electron-transport layer 114 and the second electrode 102. For the electron-injection layer 115, an alkali metal, an alkaline earth metal, or a compound thereof, such as lithium fluoride (LiF), cesium fluoride (CsF), or calcium fluoride ($CaF_2$), can be used. For example, a layer that is formed using a substance having an electron-transport property and contains an alkali metal, an alkaline earth metal, or a compound thereof can be used. An electride may also be used for the electron-injection layer 115. Examples of the electride include a substance in which electrons are added at high concentration to calcium oxide-aluminum oxide.

Note that a layer that is formed using a substance having an electron-transport property and contains an alkali metal or an alkaline earth metal is preferably used as the electron-injection layer 115, in which case electron injection from the second electrode 102 is efficiently performed. Note that it is further preferable to use the organic compound of one embodiment of the present invention as the substance having an electron-transport property.

Instead of the electron-injection layer 115, the charge-generation layer 116 may be provided (FIG. 1B). The charge-generation layer 116 refers to a layer capable of injecting holes into a layer in contact with the cathode side of the charge-generation layer 116 and electrons into a layer in contact with the anode side thereof when a potential is applied. The charge-generation layer 116 includes at least a p-type layer 117. The p-type layer 117 is preferably formed using any of the composite materials given above as examples of materials that can be used for the hole-injection layer 111. The p-type layer 117 may be formed by stacking a film containing the above-described acceptor material as a material included in the composite material and a film containing a hole-transport material. When a potential difference is applied to the p-type layer 117, electrons are injected into the electron-transport layer 114 and holes are injected into the second electrode 102 serving as a cathode from the p-type layer 117; thus, the light-emitting element operates. When a layer containing the organic compound of one embodiment of the present invention exists in the electron-transport layer 114 so as to be in contact with the charge-generation layer 116, a luminance decrease due to accumulation of driving time of the light-emitting element can be suppressed, and thus, the light-emitting element can have a long lifetime.

Note that the charge-generation layer 116 preferably includes either an electron-relay layer 118 or an electron-injection buffer layer 119 or both in addition to the p-type layer 117.

The electron-relay layer 118 contains at least the substance having an electron-transport property and has a function of preventing an interaction between the electron-injection buffer layer 119 and the p-type layer 117 and smoothly transferring electrons. The LUMO level of the substance having an electron-transport property contained in the electron-relay layer 118 is preferably between the LUMO level of the substance having an acceptor property in the p-type layer 117 and the LUMO level of a substance contained in a layer of the electron-transport layer 114 in contact with the charge-generation layer 116. As a specific value of the energy level, the LUMO level of the substance having an electron-transport property in the electron-relay layer 118 is preferably higher than or equal to −5.0 eV, more preferably higher than or equal to −5.0 eV and lower than or equal to −3.0 eV. Note that as the substance having an electron-transport property in the electron-relay layer 118, a phthalocyanine-based material or a metal complex having a metal-oxygen bond and an aromatic ligand is preferably used.

A substance having a high electron-injection property can be used for the electron-injection buffer layer 119. For example, an alkali metal, an alkaline earth metal, a rare earth metal, or a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)) can be used.

In the case where the electron-injection buffer layer 119 contains the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound of the above metal (e.g., an alkali metal compound (including an oxide such as lithium oxide, a halide, and a carbonate such as lithium carbonate or cesium carbonate), an alkaline earth metal compound (including an oxide, a halide, and a carbonate), and a rare earth metal compound (including an oxide, a halide, and a carbonate)). Note that as the substance having an electron-transport property, a material similar to the above-described material used for the electron-transport layer 114 can be used. Furthermore, the organic compound of one embodiment of the present invention can be used.

For the second electrode 102, any of metals, alloys, electrically conductive compounds, and mixtures thereof which have a low work function (specifically, a work function of 3.8 eV or less) or the like can be used. Specific examples of such a cathode material are elements belonging to Groups 1 and 2 of the periodic table, such as alkali metals (e.g., lithium (Li) and cesium (Cs)), magnesium (Mg), calcium (Ca), and strontium (Sr), alloys thereof (e.g., MgAg and AlLi), rare earth metals such as europium (Eu) and ytterbium (Yb), alloys thereof, and the like. However, when the electron-injection layer is provided between the second electrode 102 and the electron-transport layer, for the second electrode 102, any of a variety of conductive materials such as Al, Ag, ITO, or indium oxide-tin oxide containing silicon or silicon oxide can be used regardless of the work function. Films of these conductive materials can be formed by a dry method such as a vacuum evaporation method or a sputtering method, an inkjet method, a spin coating method, or the like. In addition, the electrode may be formed by a wet method using a sol-gel method, or by a wet method using paste of a metal material.

Any of a variety of methods can be used to form the EL layer 103 regardless of whether it is a dry process or a wet process. For example, a vacuum evaporation method, a gravure printing method, an offset printing method, a screen printing method, an inkjet method, a spin coating method, or the like may be used.

Different methods may be used to form the electrodes or the layers described above.

In the light-emitting element having the above-described structure, current flows due to a potential difference generated between the first electrode 101 and the second electrode 102, and holes and electrons recombine in the light-emitting layer 113, which is a layer containing a substance having a high light-emitting property, so that light is emitted.

Light generated in the light-emitting layer is extracted out through one or both of the first electrode 101 and the second electrode 102. Therefore, one or both of the first electrode 101 and the second electrode 102 are light-transmitting electrodes. In the case where only the first electrode 101 is a light-transmitting electrode, light emission is extracted through the first electrode 101. In the case where only the second electrode 102 is a light-transmitting electrode, light emission is extracted through the second electrode 102. In the case where both the first electrode 101 and the second electrode 102 are light-transmitting electrodes, light emission is extracted through the first electrode 101 and the second electrode 102.

The structure of the layers provided between the first electrode 101 and the second electrode 102 is not limited to the above-described structure. Preferably, a light-emitting region where holes and electrons recombine is positioned away from the first electrode 101 and the second electrode 102 so that quenching due to the proximity of the light-emitting region and a metal used for electrodes and carrier-injection layers can be prevented.

Furthermore, in order that transfer of energy from an exciton generated in the light-emitting layer can be suppressed, preferably, carrier-transport layers such as the hole-transport layer and the electron-transport layer which are in contact with the light-emitting layer 113, particularly a carrier-transport layer in contact with a side closer to the recombination region in the light-emitting layer 113, are formed using a substance having a wider band gap than the light-emitting substance of the light-emitting layer or the emission center substance included in the light-emitting layer.

Next, an embodiment of a light-emitting element with a structure in which a plurality of light-emitting units are stacked (this type of light-emitting element is also referred to as a stacked element or a tandem element) is described with reference to FIG. 1C. In this light-emitting element, a plurality of light-emitting units are provided between an anode and a cathode. One light-emitting unit has a structure similar to that of the EL layer 103, which is illustrated in FIG. 1A. In other words, the light-emitting element illustrated in FIG. 1C is a light-emitting element including a plurality of light-emitting units; each of the light-emitting elements illustrated in FIGS. 1A and 1B is a light-emitting element including a single light-emitting unit.

Figure 1C:
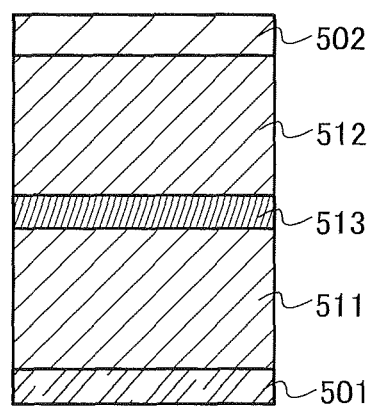

In FIG. 1C, a first light-emitting unit 511 and a second light-emitting unit 512 are stacked between a first electrode 501 and a second electrode 502, and a charge-generation layer 513 is provided between the first light-emitting unit 511 and the second light-emitting unit 512. The first electrode 501 and the second electrode 502 correspond, respectively, to the first electrode 101 and the second electrode 102 illustrated in FIG. 1A, and the materials given in the description for FIG. 1A can be used. Furthermore, the first light-emitting unit 511 and the second light-emitting unit 512 may have the same structure or different structures.

The charge-generation layer 513 has a function of injecting electrons into one of the light-emitting units and injecting holes into the other of the light-emitting units when a voltage is applied between the first electrode 501 and the second electrode 502. That is, in FIG. 1C, the charge-generation layer 513 injects electrons into the first light-emitting unit 511 and holes into the second light-emitting unit 512 when a voltage is applied so that the potential of the first electrode becomes higher than the potential of the second electrode.

The charge-generation layer 513 preferably has a structure similar to the charge-generation layer 116 described with reference to FIG. 1B. Since the composite material of an organic compound and a metal oxide is superior in carrier-injection property and carrier-transport property, low-voltage driving or low-current driving can be achieved. Note that when a surface of a light-emitting unit on the anode side is in contact with the charge-generation layer 513, the charge-generation layer 513 can also serve as a hole-injection layer in the light-emitting unit and a hole-transport layer is not necessarily formed in the light-emitting unit.

In the case where the electron-injection buffer layer 119 is provided, the electron-injection buffer layer serves as the electron-injection layer in the light-emitting unit on the anode side which is in contact with the electron-injection buffer layer 119 and the light-emitting unit does not necessarily further need an electron-injection layer.

In a light-emitting unit, when the organic compound of one embodiment of the present invention which is described in Embodiment 1 is contained in a layer in contact with a surface of the charge-generation layer 513 on the anode side (typically, the electron-transport layer in the light-emitting unit on the anode side), a luminance decrease due to accumulation of driving time can be suppressed; consequently, the light-emitting element can be highly reliable.

The light-emitting element having two light-emitting units is described with reference to FIG. 1C; however, the present invention can be similarly applied to a light-emitting element in which three or more light-emitting units are stacked. With a plurality of light-emitting units partitioned by the charge-generation layer 513 between a pair of electrodes as in the light-emitting element according to this embodiment, it is possible to provide a light-emitting element which can emit light with high luminance with the current density kept low and has a long lifetime. Moreover, a light-emitting device having low power consumption, which can be driven at low voltage, can be achieved.

Furthermore, when emission colors of light-emitting units are made different, light emission of a desired color can be provided from the light-emitting element as a whole. For example, in a light-emitting element having two light-emitting units, the emission colors of the first light-emitting unit may be red and green and the emission color of the second light-emitting unit may be blue, so that the light-emitting element can emit white light as the whole element.

The above-described structure can be combined with any of the structures in this embodiment and the other embodiments.

The light-emitting element having the above structure in this embodiment has high reliability and high heat resistance.

Embodiment 3

In this embodiment, a light-emitting device including the light-emitting element containing the organic compound of one embodiment of the present invention which is described in Embodiment 1 is described.

In this embodiment, the light-emitting device manufactured using the light-emitting element containing the organic compound of one embodiment of the present invention which is described in Embodiment 1 is described with reference to FIGS. 2A and 2B. Note that FIG. 2A is a top view of the light-emitting device and FIG. 2B is a cross-sectional view taken along the lines A-B and C-D in FIG. 2A. This light-emitting device includes a driver circuit portion (source line driver circuit) 601, a pixel portion 602, and a driver circuit portion (gate line driver circuit) 603, which are to control light emission of a light-emitting element and illustrated with dotted lines. Reference numeral 604 denotes a sealing substrate; 605, a sealing material; and 607, a space surrounded by the sealing material 605.

Reference numeral 608 denotes a lead wiring for transmitting signals to be input to the source line driver circuit 601 and the gate line driver circuit 603 and receiving signals such as a video signal, a clock signal, a start signal, and a reset signal from a flexible printed circuit (FPC) 609 serving as an external input terminal. Although only the FPC is illustrated here, a printed wiring board (PWB) may be attached to the FPC. The light-emitting device in the present specification includes, in its category, not only the light-emitting device itself but also the light-emitting device provided with the FPC or the PWB.

Next, a cross-sectional structure will be described with reference to FIG. 2B. The driver circuit portions and the pixel portion are formed over an element substrate 610; FIG. 2B shows the source line driver circuit 601, which is a driver circuit portion, and one pixel in the pixel portion 602.

The element substrate 610 may be a substrate containing glass, quartz, an organic resin, a metal, an alloy, or a semiconductor or a plastic substrate formed of fiber reinforced plastic (FRP), poly(vinyl fluoride) (PVF), polyester, or acrylic.

The structure of transistors used in pixels and driver circuits is not particularly limited. For example, inverted staggered transistors may be used, or staggered transistors may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as an In—Ga—Zn-based metal oxide, may be used.

There is no particular limitation on the crystallinity of a semiconductor material used for the transistors, and an amorphous semiconductor or a semiconductor having crystallinity (a microcrystalline semiconductor, a polycrystalline semiconductor, a single crystal semiconductor, or a semiconductor partly including crystal regions) may be used. It is preferable that a semiconductor having crystallinity be used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. When an oxide semiconductor having a wider band gap than silicon is used, off-state current of the transistors can be reduced.

The oxide semiconductor preferably contains at least indium (In) or zinc (Zn). Further preferably, the oxide semiconductor contains an oxide represented by an In-M-Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such materials for the semiconductor layer makes it possible to provide a highly reliable transistor in which a change in the electrical characteristics is suppressed.

Charge accumulated in a capacitor through a transistor including the above-described semiconductor layer can be held for a long time because of the low off-state current of the transistor. When such a transistor is used in a pixel, operation of a driver circuit can be stopped while a gray scale of an image displayed in each display region is maintained. As a result, an electronic device with extremely low power consumption can be obtained.

For stable characteristics of the transistor, a base film is preferably provided. The base film can be formed with a single-layer structure or a stacked-layer structure using an inorganic insulating film such as a silicon oxide film, a silicon nitride film, a silicon oxynitride film, or a silicon nitride oxide film. The base film can be formed by a sputtering method, a chemical vapor deposition (CVD) method (e.g., a plasma CVD method, a thermal CVD method, or a metal organic CVD (MOCVD) method), an atomic layer deposition (ALD) method, a coating method, a printing method, or the like. Note that the base film is not necessarily provided.

Note that an FET 623 is illustrated as a transistor formed in the driver circuit portion 601. In addition, the driver circuit may be formed with any of a variety of circuits such as a CMOS circuit, a PMOS circuit, or an NMOS circuit. Although a driver integrated type in which the driver circuit is formed over the substrate is illustrated in this embodiment, the driver circuit is not necessarily formed over the substrate, and the driver circuit can be formed outside, not over the substrate.

The pixel portion 602 includes a plurality of pixels including a switching FET 611, a current controlling FET 612, and a first electrode 613 electrically connected to a drain of the current controlling FET 612. One embodiment of the present invention is not limited to the structure. The pixel portion 602 may include three or more FETs and a capacitor in combination.

Note that to cover an end portion of the first electrode 613, an insulator 614 is formed, for which a positive photosensitive acrylic resin film is used here.

In order to improve coverage with an EL layer or the like which is formed later, the insulator 614 is formed to have a curved surface with curvature at its upper or lower end portion. For example, in the case where positive photosensitive acrylic is used as a material of the insulator 614, only the upper end portion of the insulator 614 preferably has a curved surface with a curvature radius (0.2 µm to 3 µm). As the insulator 614, either a negative photosensitive resin or a positive photosensitive resin can be used.

An EL layer 616 and a second electrode 617 are formed over the first electrode 613. Here, as a material used for the first electrode 613 functioning as an anode, a material having a high work function is preferably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stack of a titanium nitride film and a film containing aluminum as its main component, a stack of three layers of a titanium nitride film, a film containing aluminum as its main component, and a titanium nitride film, or the like can be used. The stacked-layer structure enables low wiring resistance, favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 2. As another material included in the EL layer 616, a low molecular compound or a high molecular compound (including an oligomer or a dendrimer) may be used.

As a material used for the second electrode 617, which is formed over the EL layer 616 and functions as a cathode, a material having a low work function (e.g., Al, Mg, Li, and Ca, or an alloy or a compound thereof, such as MgAg, MgIn, and AlLi) is preferably used. In the case where light generated in the EL layer 616 is transmitted through the second electrode 617, a stack of a thin metal film and a transparent conductive film (e.g., ITO, indium oxide containing zinc oxide at 2 wt % to 20 wt %, indium tin oxide containing silicon, or zinc oxide (ZnO)) is preferably used for the second electrode 617.

Note that the light-emitting element is formed with the first electrode 613, the EL layer 616, and the second electrode 617. The light-emitting element is the light-emitting element containing the organic compound described in Embodiment 1. In the light-emitting device of this embodiment, the pixel portion, which includes a plurality of light-emitting elements, may include both the light-emitting element containing the organic compound described in Embodiment 1 and a light-emitting element having a different structure.

The sealing substrate 604 is attached to the element substrate 610 with the sealing material 605, so that a light-emitting element 618 is provided in the space 607 surrounded by the element substrate 610, the sealing substrate 604, and the sealing material 605. The space 607 may be filled with a filler, or may be filled with an inert gas (such as nitrogen or argon), or the sealing material. It is preferable that the sealing substrate be provided with a recessed portion and a drying agent be provided in the recessed portion, in which case deterioration due to influence of moisture can be suppressed.

An epoxy-based resin or glass frit is preferably used for the sealing material 605. It is preferable that such a material not be permeable to moisture or oxygen as much as possible. As the sealing substrate 604, a glass substrate, a quartz substrate, or a plastic substrate formed of fiber reinforced plastic (FRP), polyvinyl fluoride) (PVF), polyester, and acrylic can be used.

Although not illustrated in FIGS. 2A and 2B, a protective film may be provided over the second electrode. As the protective film, an organic resin film or an inorganic insulating film may be formed. The protective film may be formed so as to cover an exposed portion of the sealing material 605. The protective film may be provided so as to cover surfaces and side surfaces of the pair of substrates and exposed side surfaces of a sealing layer, an insulating layer, and the like.

The protective film can be formed using a material through which an impurity such as water does not permeate easily. Thus, diffusion of an impurity such as water from the outside into the inside can be effectively suppressed.

As a material of the protective film, an oxide, a nitride, a fluoride, a sulfide, a ternary compound, a metal, a polymer, or the like can be used. For example, the material may contain aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide, aluminum nitride, hafnium nitride, silicon nitride, tantalum nitride, titanium nitride, niobium nitride, molybdenum nitride, zirconium nitride, gallium nitride, a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method with favorable step coverage. One such method is an atomic layer deposition (ALD) method. A material that can be deposited by an ALD method is preferably used for the protective film. A dense protective film having reduced defects such as cracks or pinholes or a uniform thickness can be formed by an ALD method. Furthermore, damage caused to a process member in forming the protective film can be reduced.

By an ALD method, a uniform protective film with few defects can be formed even on, for example, a surface with a complex uneven shape or upper, side, and lower surfaces of a touch panel.

As described above, the light-emitting device manufactured using the light-emitting element containing the organic compound described in Embodiment 1 can be obtained.

The light-emitting device in this embodiment is fabricated using the light-emitting element containing the organic compound described in Embodiment 1 and thus can have favorable characteristics. Specifically, since the light-emitting element containing the organic compound described in Embodiment 1 has high heat resistance, the light-emitting device can have high heat resistance. Since crosstalk can be reduced in the light-emitting device using the light-emitting element containing the organic compound described in Embodiment 1, high display quality can be achieved. In addition, since the light-emitting element can be easily mass-produced, the light-emitting device can be provided at low cost.

FIGS. 3A and 3B each illustrate an example of a light-emitting device in which full color display is achieved by formation of a light-emitting element exhibiting white light emission and with the use of coloring layers (color filters) and the like. In FIG. 3A, a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of light-emitting elements, a partition 1025, an EL layer 1028, a second electrode 1029 of the light-emitting elements, a sealing substrate 1031, a sealing material 1032, and the like are illustrated.

In FIG. 3A, coloring layers (a red coloring layer 1034R, a green coloring layer 1034G, and a blue coloring layer 1034B) are provided on a transparent base material 1033. A black matrix 1035 may be additionally provided. The transparent base material 1033 provided with the coloring layers and the black matrix is aligned and fixed to the substrate 1001. Note that the coloring layers and the black matrix 1035 are covered with an overcoat layer 1036. In FIG. 3A, light emitted from part of the light-emitting layer does not pass through the coloring layers, while light emitted from the other part of the light-emitting layer passes through the coloring layers. Since light which does not pass through the coloring layers is white and light which passes through any one of the coloring layers is red, green, or blue, an image can be displayed using pixels of the four colors.

FIG. 3B illustrates an example in which the coloring layers (the red coloring layer 1034R, the green coloring layer 1034G, and the blue coloring layer 1034B) are provided between the gate insulating film 1003 and the first interlayer insulating film 1020. As in the structure, the coloring layers may be provided between the substrate 1001 and the sealing substrate 1031.

Figure 4:
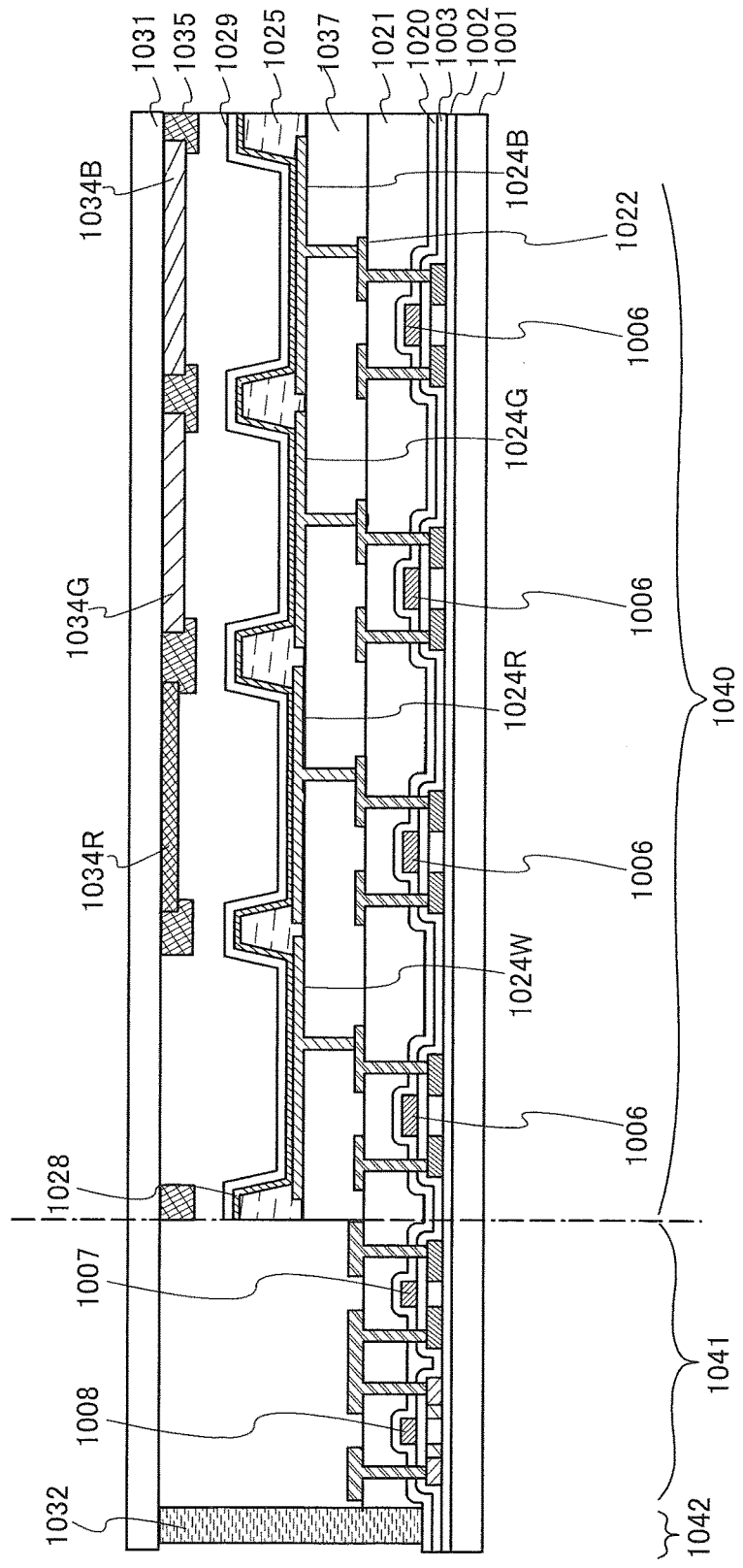
FIG. 4 is a schematic diagram of an active matrix light-emitting device.

The above-described light-emitting device is a light-emitting device having a structure in which light is extracted from the substrate 1001 side where FETs are formed (a bottom emission structure), but may be a light-emitting device having a structure in which light is extracted from the sealing substrate 1031 side (a top emission structure). FIG. 4 is a cross-sectional view of a light-emitting device having a top emission structure. In this case, a substrate which does not transmit light can be used as the substrate 1001. The process up to the step of forming a connection electrode which connects the FET and the anode of the light-emitting element is performed in a manner similar to that of the light-emitting device having a bottom emission structure. Then, a third interlayer insulating film 1037 is formed to cover an electrode 1022. This insulating film may have a planarization function. The third interlayer insulating film 1037 can be formed using a material similar to that of the second interlayer insulating film, and can alternatively be formed using any of other known materials.

The first electrodes 1024W, 1024R, 1024G, and 1024B of the light-emitting elements each serve as an anode here, but may serve as a cathode. Furthermore, in the case of a light-emitting device having a top emission structure as illustrated in FIG. 4, the first electrodes are preferably reflective electrodes. The EL layer 1028 is formed to have a structure similar to the structure of the EL layer 103, which is described in Embodiment 2, with which white light emission can be obtained.

In the case of a top emission structure as illustrated in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031.

Although an example in which full color display is performed using four colors of red, green, blue, and white is shown here, there is no particular limitation and full color display using four colors of red, yellow, green, and blue or three colors of red, green, and blue may be performed.

In the light-emitting device having a top emission structure, a microcavity structure can be favorably employed. A light-emitting element with a microcavity structure is formed with the use of a reflective electrode as the first electrode and a semi-transmissive and semi-reflective electrode as the second electrode. The light-emitting element with a microcavity structure includes at least an EL layer between the reflective electrode and the semi-transmissive and semi-reflective electrode, which includes at least a light-emitting layer serving as a light-emitting region.

Note that the reflective electrode is formed using a conductive material having reflectivity, a visible light reflectivity of 40% to 100%, preferably 70% to 100%, and a resistivity of $1 \times 10^{-2}$ Ωcm or lower. In addition, the semi-transmissive and semi-reflective electrode are formed using a conductive material having reflectivity, a visible light reflectivity of 20% to 80%, preferably 40% to 70%, and a resistivity of $1 \times 10^{-2}$ Ωcm or lower.

Light emitted from the light-emitting layer included in the EL layer is reflected and resonated by the reflective electrode and the semi-transmissive and semi-reflective electrode.

In the light-emitting element, by changing thicknesses of the transparent conductive film, the composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light). For this reason, the optical path length between the reflective electrode and the light-emitting layer is preferably adjusted to $(2n-1)\lambda/4$ (n is a natural number of 1 or larger and $\lambda$ is a wavelength of color to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. The tandem light-emitting element described above may be combined with a plurality of EL layers; for example, a light-emitting element may have a structure in which a plurality of EL layers are provided, a charge-generation layer is provided between the EL layers, and each EL layer includes a plurality of light-emitting layers or a single light-emitting layer.

With the microcavity structure, emission intensity with a specific wavelength in the front direction can be increased, whereby power consumption can be reduced. Note that in the case of a light-emitting device which displays images with subpixels of four colors, red, yellow, green, and blue, the light-emitting device can have favorable characteristics because the luminance can be increased owing to yellow light emission and each subpixel can employ a microcavity structure suitable for wavelengths of the corresponding color.

The light-emitting device in this embodiment is fabricated using the light-emitting element containing the organic compound described in Embodiment 1 and thus can have favorable characteristics. Specifically, since the light-emitting element containing the organic compound described in Embodiment 1 has high heat resistance, the light-emitting device can have high heat resistance. Since crosstalk can be reduced in the light-emitting device using the light-emitting element containing the organic compound described in Embodiment 1, high display quality can be achieved.

Figure 5A:
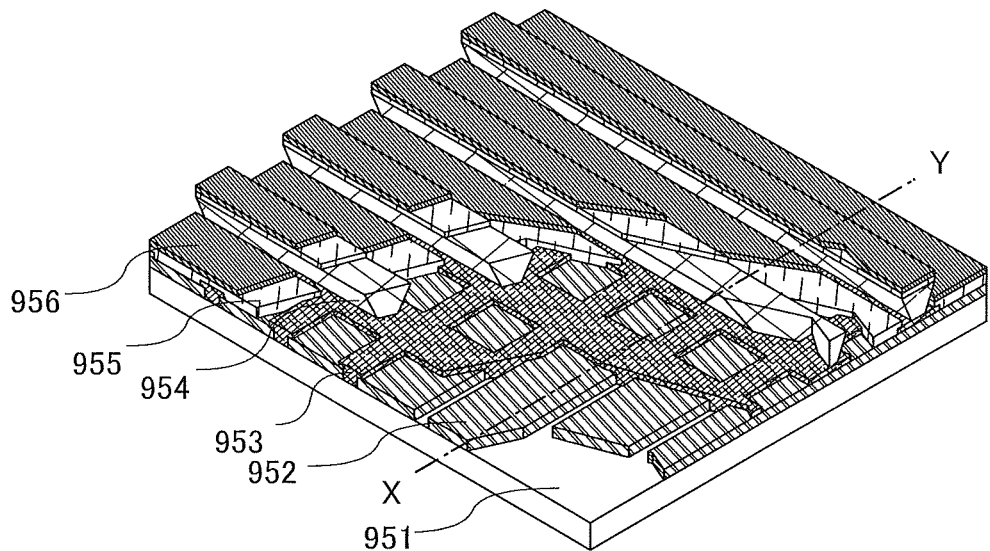
FIGS. 5A and 5B are schematic diagrams of a passive matrix light-emitting device.
Figure 5B:
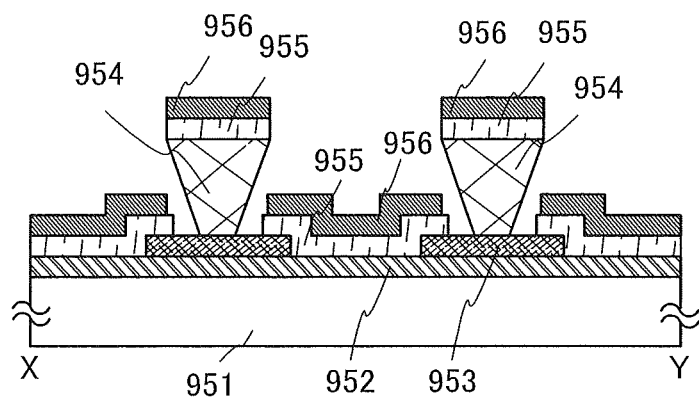

An active matrix light-emitting device is described above, whereas a passive matrix light-emitting device is described below. FIGS. 5A and 5B illustrate a passive matrix light-emitting device manufactured using the present invention. Note that FIG. 5A is a perspective view of the light-emitting device, and FIG. 5B is a cross-sectional view taken along the line X-Y in FIG. 5A. In FIGS. 5A and 5B, over a substrate 951, an EL layer 955 is provided between an electrode 952 and an electrode 956. An end portion of the electrode 952 is covered with an insulating layer 953. A partition layer 954 is provided over the insulating layer 953. The sidewalls of the partition layer 954 are aslope such that the distance between both sidewalls is gradually narrowed toward the surface of the substrate. In other words, a cross section taken along the direction of the short side of the partition layer 954 is trapezoidal, and the lower side (a side of the trapezoid which is parallel to the surface of the insulating layer 953 and is in contact with the insulating layer 953) is shorter than the upper side (a side of the trapezoid which is parallel to the surface of the insulating layer 953 and is not in contact with the insulating layer 953). The partition layer 954 thus provided can prevent defects in the light-emitting element due to static electricity or others. The passive-matrix light-emitting device also includes the light-emitting element containing the organic compound described in Embodiment 1; thus, the light-emitting device can have high heat resistance.

Since many minute light-emitting elements arranged in a matrix in the light-emitting device described above can each be controlled, the light-emitting device can be suitably used as a display device for displaying images.

This embodiment can be freely combined with any of the other embodiments.

Embodiment 4

Figure 6A:
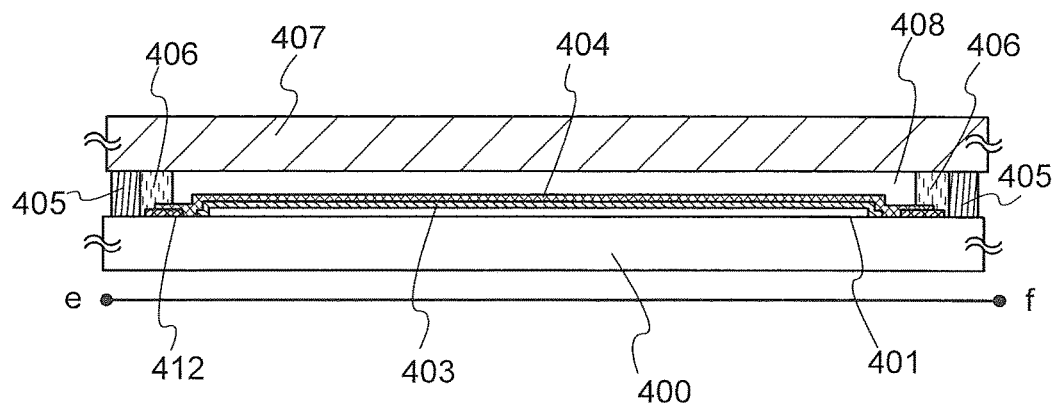
FIGS. 6A and 6B illustrate a lighting device.
Figure 6B:
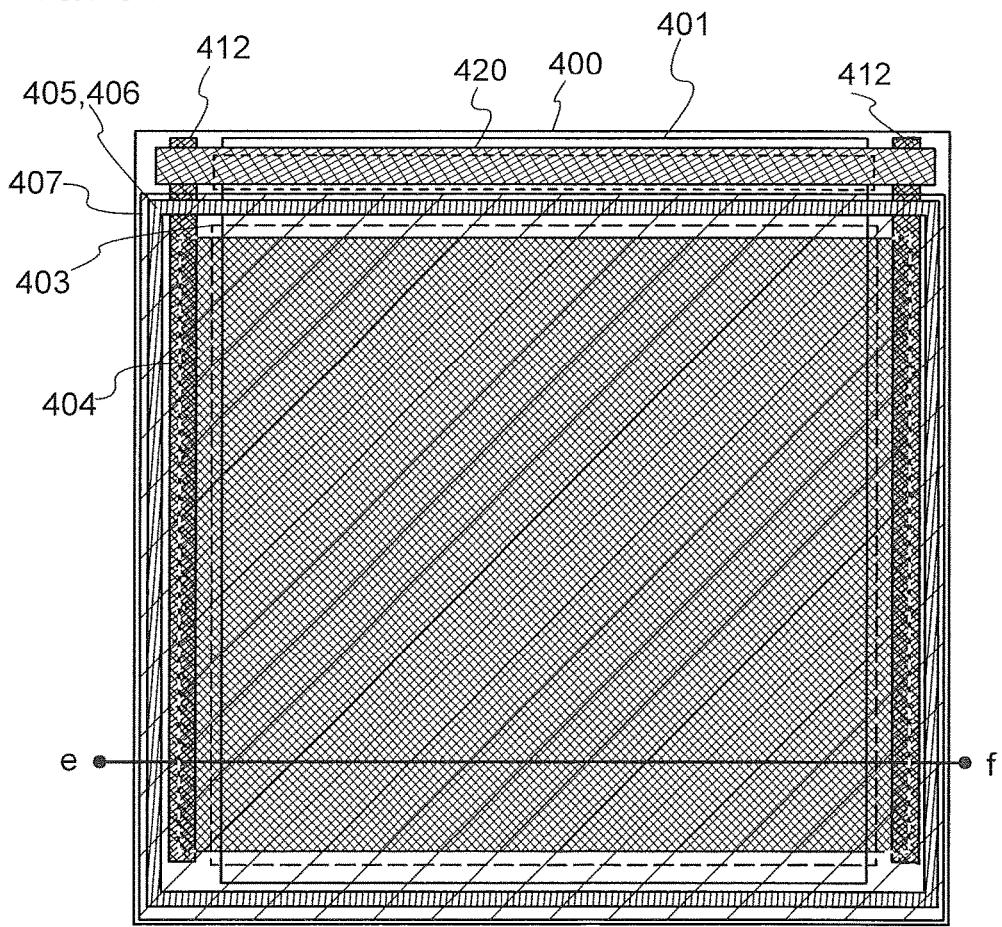

In this embodiment, an example in which the light-emitting element containing the organic compound described in Embodiment 1 is used for a lighting device will be described with reference to FIGS. 6A and 6B. FIG. 6B is a top view of the lighting device, and FIG. 6A is a cross-sectional view taken along the line e-f in FIG. 6B.

In the lighting device in this embodiment, a first electrode 401 is formed over a substrate 400 which is a support and has a light-transmitting property. The first electrode 401 corresponds to the first electrode 101 in Embodiment 2. When light is extracted through the first electrode 401 side, the first electrode 401 is formed using a material having a light-transmitting property.

A pad 412 for applying voltage to a second electrode 404 is provided over the substrate 400.

An EL layer 403 is formed over the first electrode 401. The structure of the EL layer 403 corresponds to, for example, the structure of the EL layer 103 in Embodiment 2, or the structure in which the light-emitting units 511 and 512 and the charge-generation layer 513 are combined. Refer to the descriptions for the structure.

The second electrode 404 is formed to cover the EL layer 403. The second electrode 404 corresponds to the second electrode 102 in Embodiment 2. The second electrode 404 is formed using a material having high reflectance when light is extracted through the first electrode 401 side. The second electrode 404 is connected to the pad 412, whereby voltage is applied.

As described above, the lighting device described in this embodiment includes a light-emitting element including the first electrode 401, the EL layer 403, and the second electrode 404. Since the light-emitting element is a light-emitting element with high emission efficiency, the lighting device in this embodiment can be a lighting device having low power consumption.

The substrate 400 provided with the light-emitting element having the above structure is fixed to a sealing substrate 407 with sealing materials 405 and 406 and sealing is performed, whereby the lighting device is completed. It is possible to use only either the sealing material 405 or the sealing material 406. The inner sealing material 406 (not shown in FIG. 6B) can be mixed with a desiccant which enables moisture to be adsorbed, increasing reliability.

When parts of the pad 412 and the first electrode 401 are extended to the outside of the sealing materials 405 and 406, the extended parts can serve as external input terminals. An IC chip 420 mounted with a converter or the like may be provided over the external input terminals.

The lighting device described in this embodiment includes as an EL element the light-emitting element containing the organic compound described in Embodiment 1; thus, the light-emitting device can have high reliability. The light-emitting device can also have high heat resistance.

Embodiment 5

In this embodiment, examples of electronic devices each including the light-emitting element containing the organic compound described in Embodiment 1 are described. The light-emitting element containing the organic compound described in Embodiment 1 has high heat resistance. As a result, the electronic devices described in this embodiment can each include a light-emitting portion having high reliability. Since crosstalk can be reduced in the light-emitting device using the light-emitting element containing the organic compound described in Embodiment 1, the electronic devices can have high display quality.

Examples of the electronic devices to which the above light-emitting element is applied include television devices (also referred to as TV or television receivers), monitors for computers and the like, cameras such as digital cameras and digital video cameras, digital photo frames, mobile phones (also referred to as cell phones or mobile phone devices), portable game machines, portable information terminals, audio playback devices, large game machines such as pachinko machines, and the like. Specific examples of these electronic devices are given below.

FIG. 7A illustrates an example of a television device. In the television device, a display portion 7103 is incorporated in a housing 7101. Here, the housing 7101 is supported by a stand 7105. Images can be displayed on the display portion 7103, and in the display portion 7103, the light-emitting elements each containing the organic compound described in Embodiment 1 are arranged in a matrix.

Operation of the television device can be performed with an operation switch of the housing 7101 or a separate remote controller 7110. With operation keys 7109 of the remote controller 7110, channels and volume can be controlled and images displayed on the display portion 7103 can be controlled. The remote controller 7110 may be provided with a display portion 7107 for displaying data output from the remote controller 7110.

Note that the television device is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

FIG. 7B1 illustrates a computer, which includes a main body 7201, a housing 7202, a display portion 7203, a keyboard 7204, an external connection port 7205, a pointing device 7206, and the like. Note that this computer is manufactured by arranging light-emitting elements similar to those containing the organic compound described in Embodiment 1 in a matrix in the display portion 7203. The computer illustrated in FIG. 7B1 may have a structure illustrated in FIG. 7B2. The computer illustrated in FIG. 7B2 is provided with a second display portion 7210 instead of the keyboard 7204 and the pointing device 7206. The second display portion 7210 has a touch screen, and input can be performed by operation of images, which are displayed on the second display portion 7210, with a finger or a dedicated pen. The second display portion 7210 can also display images other than the display for input. The display portion 7203 may also have a touch screen. Connecting the two screens with a hinge can prevent troubles; for example, the screens can be prevented from being cracked or broken while the computer is being stored or carried.

FIG. 7C illustrates a portable game machine having two housings, a housing 7301 and a housing 7302, which are connected with a joint portion 7303 so that the portable game machine can be folded. The housing 7301 incorporates a display portion 7304 in which the light-emitting elements each containing the organic compound described in Embodiment 1 are arranged in a matrix, and the housing 7302 incorporates a display portion 7305. In addition, the portable game machine illustrated in FIG. 7C includes a speaker portion 7306, a recording medium insertion portion 7307, an LED lamp 7308, input means (an operation key 7309, a connection terminal 7310, a sensor 7311 (a sensor having a function of measuring or sensing force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), and a microphone 7312), and the like. Needless to say, the structure of the portable game machine is not limited to the above as long as the display portion in which the light-emitting elements each containing the organic compound described in Embodiment 1 are arranged in a matrix is used as either the display portion 7304 or the display portion 7305, or both, and the structure can include other accessories as appropriate. The portable game machine illustrated in FIG. 7C has a function of reading out a program or data stored in a recoding medium to display it on the display portion, and a function of sharing information with another portable game machine by wireless communication. Note that functions of the portable game machine illustrated in FIG. 7C are not limited to them, and the portable game machine can have various functions.

FIG. 7D illustrates an example of a portable terminal. The mobile phone is provided with a display portion 7402 incorporated in a housing 7401, operation buttons 7403, an external connection port 7404, a speaker 7405, a microphone 7406, and the like. Note that the mobile phone 7400 has the display portion 7402 in which the light-emitting elements each containing the organic compound described in Embodiment 1 are arranged in a matrix.

When the display portion 7402 of the portable terminal illustrated in FIG. 7D is touched with a finger or the like, data can be input into the portable terminal. In this case, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating an e-mail, a character input mode is selected for the display portion 7402 so that characters displayed on a screen can be input. In this case, it is preferable to display a keyboard or number buttons on almost the entire screen of the display portion 7402.

When a sensing device including a sensor such as a gyroscope or an acceleration sensor for detecting inclination is provided inside the portable terminal, display on the screen of the display portion 7402 can be automatically changed in direction by determining the orientation of the portable terminal (whether the portable terminal is placed horizontally or vertically).

The screen modes are switched by touch on the display portion 7402 or operation with the operation buttons 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by the display portion 7402 while in touch with the palm or the finger, whereby personal authentication can be performed. Furthermore, by providing a backlight or a sensing light source which emits near-infrared light in the display portion, an image of a finger vein, or a palm vein can be taken.

Note that the structure described in this embodiment can be combined with any of the structures described in Embodiments 1 to 4 as appropriate.

As described above, the application range of the light-emitting device including the light-emitting element containing the organic compound described in Embodiment 1 is wide so that this light-emitting device can be applied to electronic devices in a variety of fields. By using the light-emitting element containing the organic compound described in Embodiment 1, an electronic device having high heat resistance and high reliability can be obtained.

Figure 8:
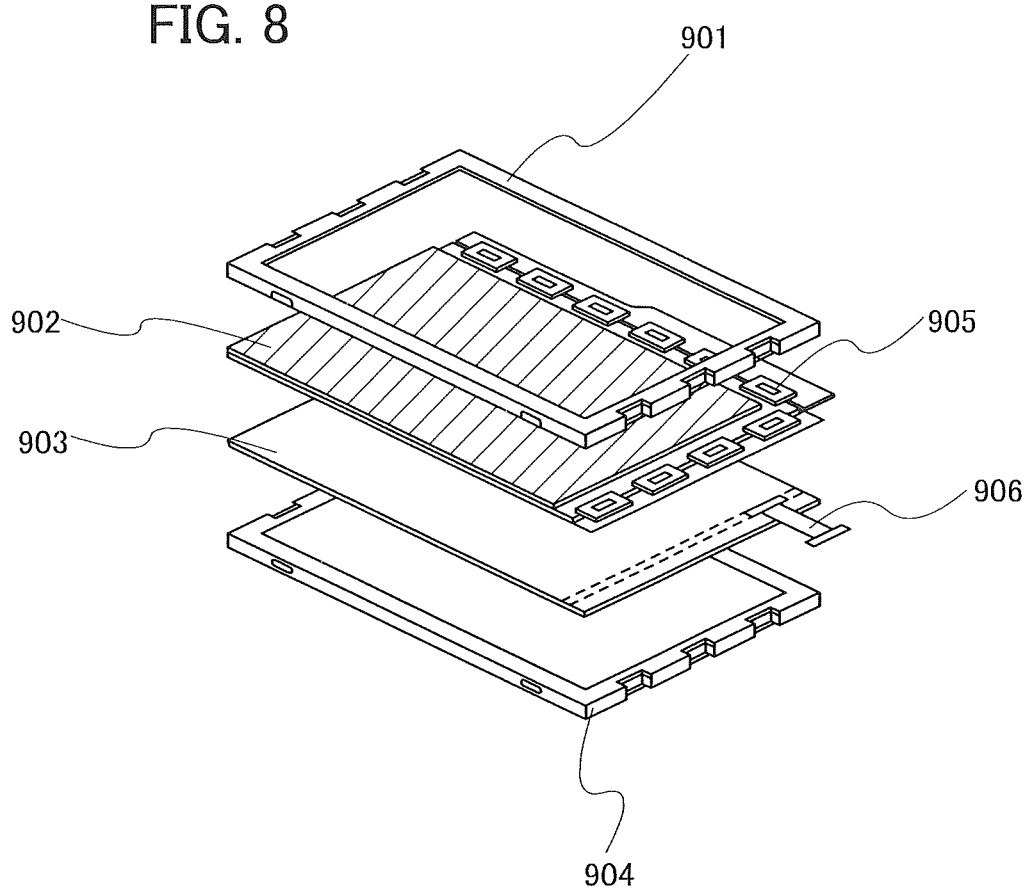
FIG. 8 illustrates a light source device.

FIG. 8 illustrates an example of a liquid crystal display device using the light-emitting element containing the organic compound described in Embodiment 1 for a backlight. The liquid crystal display device illustrated in FIG. 8 includes a housing 901, a liquid crystal layer 902, a backlight unit 903, and a housing 904. The liquid crystal layer 902 is connected to a driver IC 905. The light-emitting element containing the organic compound described in Embodiment 1 is used for the backlight unit 903, to which current is supplied through a terminal 906.

The light-emitting element containing the organic compound described in Embodiment 1 is used for the backlight of the liquid crystal display device; thus, the backlight can have reduced power consumption. In addition, the use of the light-emitting element containing the organic compound described in Embodiment 1 enables manufacture of a planar-emission lighting device and further a larger-area planar-emission lighting device; therefore, the backlight can be a larger-area backlight, and the liquid crystal display device can also be a larger-area device. Furthermore, the light-emitting device including the light-emitting element containing the organic compound described in Embodiment 1 can be thinner than a conventional one; accordingly, the display device can also be thinner.

Figure 9:
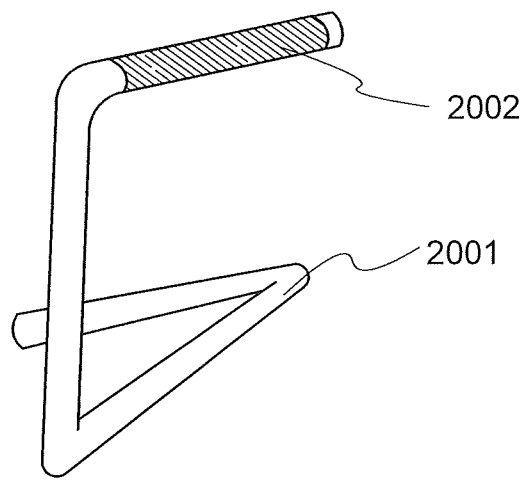
FIG. 9 illustrates a lighting device.

FIG. 9 illustrates an example in which the light-emitting element containing the organic compound described in Embodiment 1 is used for a table lamp which is a lighting device. The table lamp illustrated in FIG. 9 includes a housing 2001 and a light source 2002, and the lighting device described in Embodiment 4 may be used for the light source 2002.

Figure 10:
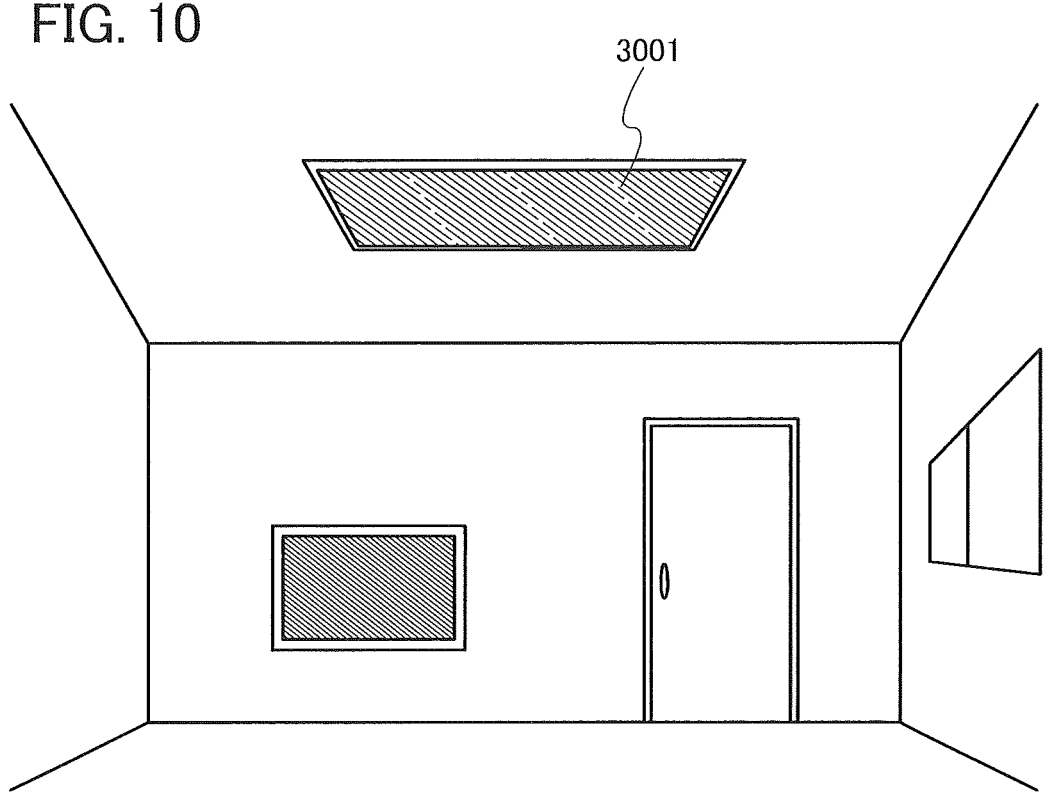
FIG. 10 illustrates a lighting device.

FIG. 10 illustrates an example in which the light-emitting element containing the organic compound described in Embodiment 1 is used for an indoor lighting device 3001. Since the light-emitting element containing the organic compound described in Embodiment 1 has high heat resistance, the lighting device can have high heat resistance. Furthermore, since the light-emitting element containing the organic compound described in Embodiment 1 can have a large area, the light-emitting element can be used for a large-area lighting device. Furthermore, since the light-emitting element containing the organic compound described in Embodiment 1 is thin, the light-emitting element can be used for a lighting device having a reduced thickness.

Figure 11:
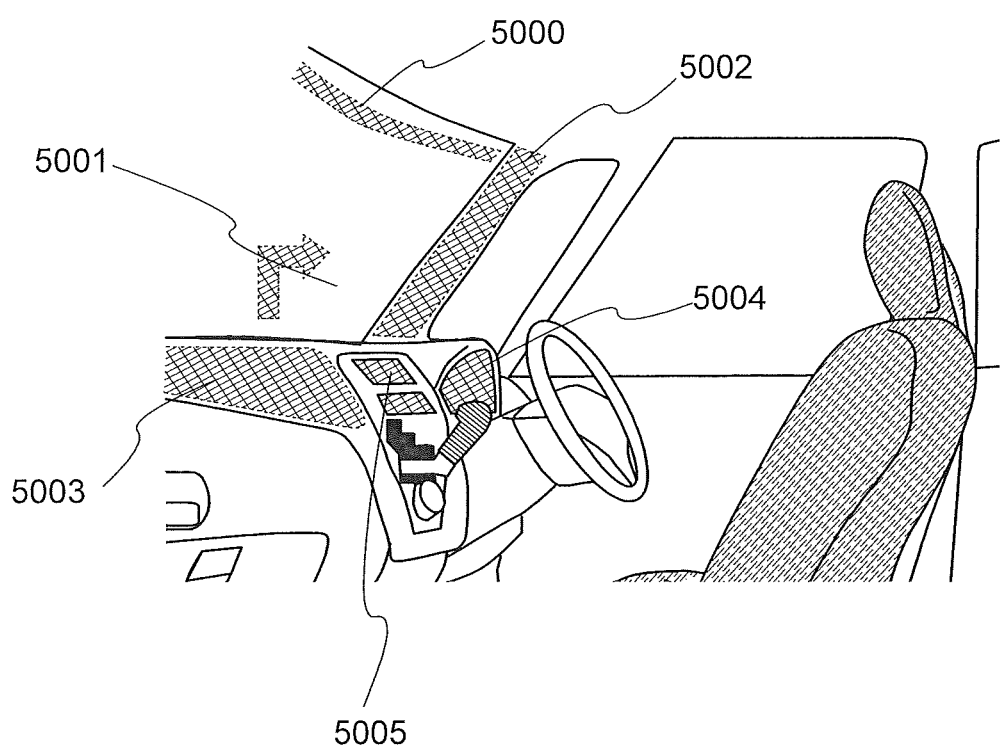
FIG. 11 illustrates in-vehicle display devices and lighting devices.

The light-emitting element containing the organic compound described in Embodiment 1 can also be used for an automobile windshield or an automobile dashboard. FIG. 11 illustrates one mode in which the light-emitting element containing the organic compound described in Embodiment 1 is used for an automobile windshield and an automobile dashboard. Display regions 5000 to 5005 each include the light-emitting element containing the organic compound described in Embodiment 1.

The display region 5000 and the display region 5001 are display devices provided in the automobile windshield in which the light-emitting elements each containing the organic compound described in Embodiment 1 are incorporated. The light-emitting elements each containing the organic compound described in Embodiment 1 can be formed into what is called a see-through display device, through which the opposite side can be seen, by including a first electrode and a second electrode formed of electrodes having a light-transmitting property. Such see-through display devices can be provided even in the automobile windshield, without hindering the vision. Note that in the case where a driving transistor or the like is provided, a transistor having a light-transmitting property, such as an organic transistor using an organic semiconductor material or a transistor using an oxide semiconductor, is preferably used.

The display region 5002 is a display device provided in a pillar portion in which the light-emitting elements each containing the organic compound described in Embodiment 1 are incorporated. The display region 5002 can compensate for the view hindered by the pillar portion by showing an image taken by an imaging unit provided in the car body. Similarly, the display region 5003 provided in the dashboard can compensate for the view hindered by the car body by showing an image taken by an imaging unit provided in the outside of the car body, which leads to elimination of blind areas and enhancement of safety. Showing an image so as to compensate for the area which a driver cannot see makes it possible for the driver to confirm safety easily and comfortably.

The display region 5004 and the display region 5005 can provide a variety of kinds of information such as navigation data, a speedmeter, a tachometer, a mileage, a fuel level, a gearshift state, and air-condition setting. The content or layout of the display can be freely changed by a user as appropriate. Note that such information can also be shown by the display regions 5000 to 5003. The display regions 5000 to 5005 can also be used as lighting devices.

The light-emitting element containing the organic compound described in Embodiment 1 has high heat resistance. Accordingly, the light-emitting element containing the organic compound described in Embodiment 1 can be suitably used for an in-vehicle light-emitting device or lighting device which is placed in a very high-temperature environment in midsummer or the like.

Figure 12A:
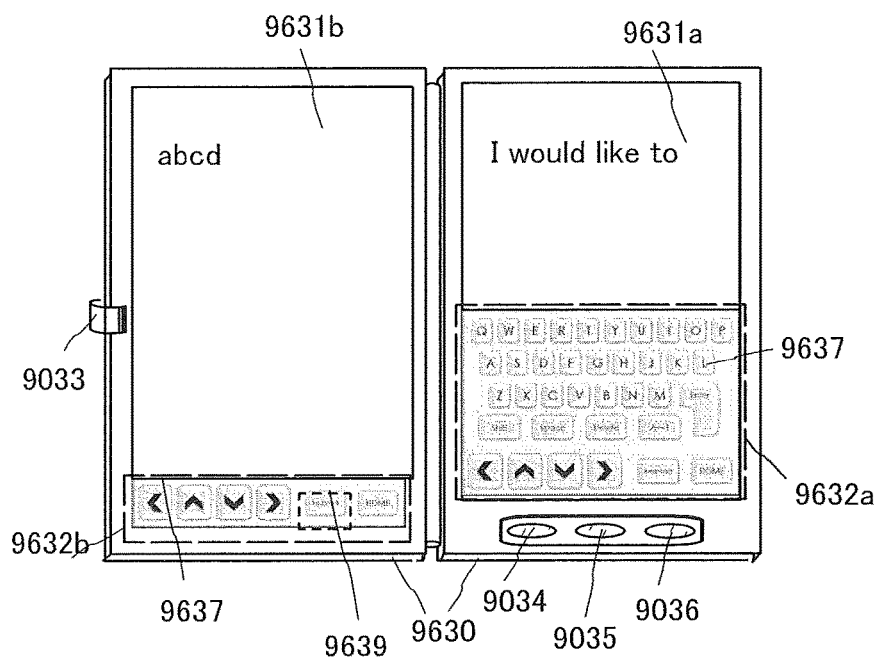
FIGS. 12A to 12C illustrate an electronic device.
Figure 12B:
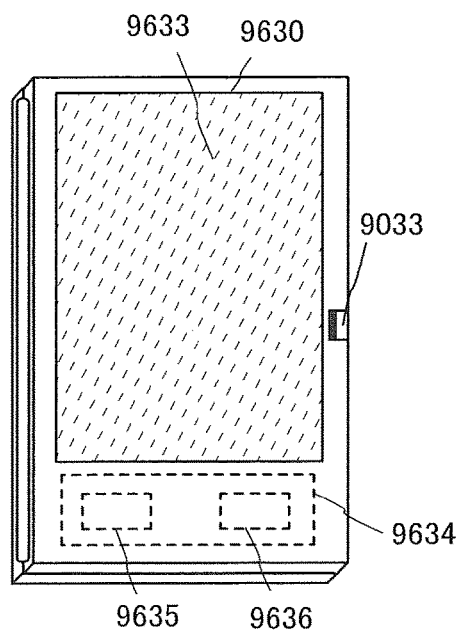

FIGS. 12A and 12B illustrate an example of a foldable tablet terminal. FIG. 12A illustrates the tablet terminal which is unfolded. The tablet terminal includes a housing 9630, a display portion 9631*a*, a display portion 9631*b*, a display mode switch 9034, a power switch 9035, a power-saving mode switch 9036, a clasp 9033, and an operation switch 9038. Note that in the tablet terminal, one or both of the display portion 9631*a* and the display portion 9631*b* is/are formed using a light-emitting device which includes the light-emitting element containing the organic compound described in Embodiment 1.

Part of the display portion 9631*a* can be a touchscreen region 9632*a* and data can be input when a displayed operation key 9637 is touched. Although half of the display portion 9631*a* has only a display function and the other half has a touchscreen function, one embodiment of the present invention is not limited to the structure. The whole display portion 9631*a* may have a touchscreen function. For example, a keyboard can be displayed on the entire region of the display portion 9631*a* so that the display portion 9631*a* is used as a touchscreen, and the display portion 9631*b* can be used as a display screen.

Like the display portion 9631*a*, part of the display portion 9631*b* can be a touchscreen region 9632*b*. When a switching button 9639 for showing/hiding a keyboard on the touchscreen is touched with a finger, a stylus, or the like, the keyboard can be displayed on the display portion 9631*b*.

Touch input can be performed in the touchscreen region 9632*a* and the touchscreen region 9632*b* at the same time.

The display mode switch 9034 can switch the display between portrait mode, landscape mode, and the like, and between monochrome display and color display, for example. The power-saving mode switch 9036 can control display luminance in accordance with the amount of external light in use of the tablet terminal sensed by an optical sensor incorporated in the tablet terminal. Another sensing device including a sensor such as a gyroscope or an acceleration sensor for sensing inclination may be incorporated in the tablet terminal, in addition to the optical sensor.

Although FIG. 12A illustrates an example in which the display portion 9631a and the display portion 9631b have the same display area, one embodiment of the present invention is not limited to the example. The display portion 9631a and the display portion 9631b may have different display areas and different display quality. For example, higher definition images may be displayed on one of the display portions 9631a and 9631b.

FIG. 12B illustrates the tablet terminal which is folded. The tablet terminal in this embodiment includes the housing 9630, a solar cell 9633, a charge and discharge control circuit 9634, a battery 9635, and a DCDC converter 9636. In FIG. 12B, a structure including the battery 9635 and the DCDC converter 9636 is illustrated as an example of the charge and discharge control circuit 9634.

Since the tablet terminal is foldable, the housing 9630 can be closed when the tablet terminal is not in use. As a result, the display portion 9631a and the display portion 9631b can be protected, thereby providing a tablet terminal with high endurance and high reliability for long-term use.

The tablet terminal illustrated in FIGS. 12A and 12B can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs).

The solar cell 9633 provided on a surface of the tablet terminal can supply power to the touchscreen, the display portion, a video signal processing portion, or the like. Note that a structure in which the solar cell 9633 is provided on one or both surfaces of the housing 9630 is preferable because the battery 9635 can be charged efficiently.

Figure 12C:
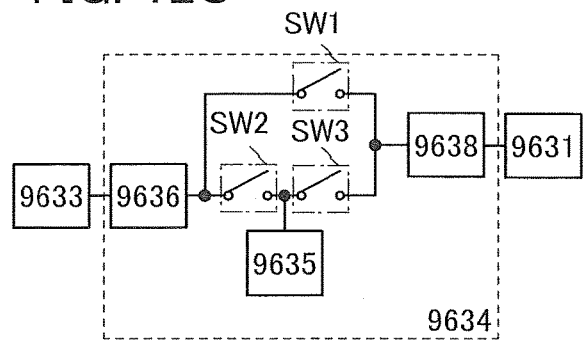

The structure and operation of the charge and discharge control circuit 9634 illustrated in FIG. 12B will be described with reference to a block diagram of FIG. 12C. FIG. 12C illustrates the solar cell 9633, the battery 9635, the DCDC converter 9636, a converter 9638, switches SW1 to SW3, and a display portion 9631. The battery 9635, the DCDC converter 9636, the converter 9638, and the switches SW1 to SW3 correspond to the charge and discharge control circuit 9634 illustrated in FIG. 12B.

First, description is made on an example of the operation in the case where power is generated by the solar cell 9633 with the use of external light. The voltage of the power generated by the solar cell is raised or lowered by the DCDC converter 9636 so as to be voltage for charging the battery 9635. Then, when power from the solar cell 9633 is used for the operation of the display portion 9631, the switch SW1 is turned on and the voltage of the power is raised or lowered by the converter 9638 so as to be voltage needed for the display portion 9631. When images are not displayed on the display portion 9631, the switch SW1 is turned off and the switch SW2 is turned on so that the battery 9635 is charged.

Although the solar cell 9633 is described as an example of a power generation means, the power generation means is not particularly limited, and the battery 9635 may be charged by another power generation means such as a piezoelectric element or a thermoelectric conversion element (Peltier element). The battery 9635 may be charged by a non-contact power transmission module capable of performing charging by transmitting and receiving power wirelessly (without contact), or any of the other charge means used in combination, and the power generation means is not necessarily provided.

One embodiment of the present invention is not limited to the tablet terminal having the shape illustrated in FIGS. 12A to 12C as long as the display portion 9631 is included.

Figure 28A:
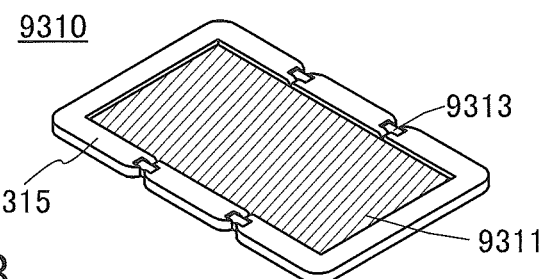
FIGS. 28A to 28C illustrate an electronic device.
Figure 28B:
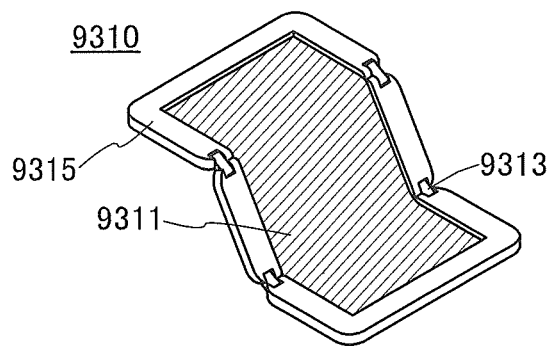
Figure 28C:
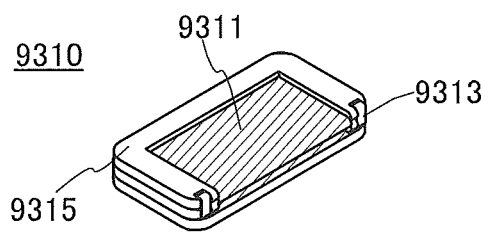

FIGS. 28A to 28C illustrate a foldable portable information terminal 9310. FIG. 28A illustrates the portable information terminal 9310 that is opened. FIG. 28B illustrates the portable information terminal 9310 that is being opened or being folded. FIG. 28C illustrates the portable information terminal 9310 that is folded. The portable information terminal 9310 is highly portable when folded. When the portable information terminal 9310 is opened, a seamless large display region is highly browsable.

A display panel 9311 is supported by three housings 9315 joined together by hinges 9313. The display panel 9311 may be a touch panel (an input/output device) including a touch sensor (an input device). By bending the display panel 9311 at a connection portion between two housings 9315 with the use of the hinges 9313, the portable information terminal 9310 can be reversibly changed in shape from an opened state to a folded state. The light-emitting device of one embodiment of the present invention can be used for the display panel 9311. A display region 9312 in the display panel 9311 includes a display region that is positioned at a side surface of the portable information terminal 9310 that is folded. On the display region 9312, information icons, frequently-used applications, file shortcuts to programs, and the like can be displayed, and confirmation of information and start of application can be smoothly performed.

Example 1

Synthesis Example 1

In this example, a method of synthesizing 2,2'-(pyridine-2,6-diyl)bis(4-phenylbenzo[h]quinazoline) (abbreviation: 2,6(P-Bqn)2Py), which is represented by the structural formula (100) in Embodiment 1, is described. The structure of 2,6(P-Bqn)2Py is shown below.

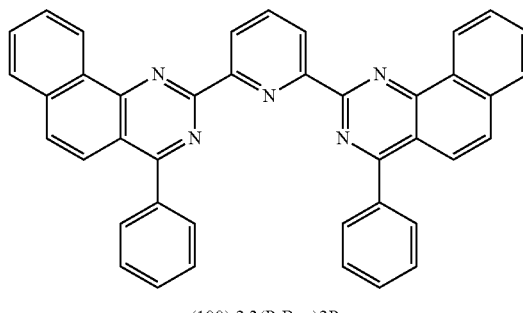

(100) 2,3(P-Bqn)2Py

Step 1: Synthesis of 2,6-pyridinedicarboxamidine dihydrochloride

First, 15.4 g (119 mmol) of 2,6-pyridinedicarbonitrile and 250 mL of methanol (dehydrated) were put into a 500-mL three-neck flask and mixed. Then, 591 mg (10.9 mmol) of sodium methoxide was added to this mixture, and the mixture was stirred under a nitrogen stream at room temperature for 16 hours. After that, 12.7 g (238 mmol) of ammonium chloride was added, and the mixture was stirred under a nitrogen stream at room temperature for two days. After the reaction, the reaction mixture was concentrated, and ethyl acetate was added thereto. The mixture was irradiated with ultrasonic waves, and the lump was crushed into pieces and then suction filtered to give 25.5 g of a white solid in a yield of 91%. The obtained white solid was identified as 2,6-pyridinedicarboxamidine dihydrochloride by nuclear magnetic resonance (NMR) spectroscopy. The synthesis scheme (a-1) of the step 1 is shown below.

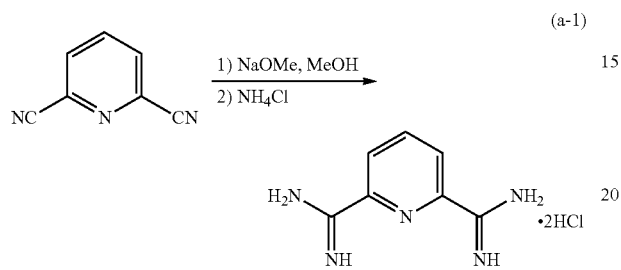

(a-1)

Step 2: Synthesis of N,N'-di(naphthalen-1-yl)-2,6-pyridinedicarboxamidine

First, 11.6 g (49.2 mmol) of 2,6-pyridinedicarboxamidine dihydrochloride, 64.1 g (197 mmol) of cesium carbonate, and 0.937 g (4.92 mmol) of copper iodide were put into a reaction container, and the air in the flask was replaced with nitrogen. Then, 100 mL of N,N'-dimethylformamide and 25.0 g (98.4 mmol) of 1-iodonaphthalene were added to this mixture, and the mixture was stirred to be degassed while the pressure in the flask was reduced. After that, the mixture was heated under a nitrogen stream at 90° C. for 33 hours. After the reaction mixture was suction filtered, the residue was washed with water and chloroform, and the filtrate that had been obtained was combined with the solution used for the washing to give a filtrate. The obtained filtrate was subjected to extraction with chloroform. The obtained solution of the extract was washed with water and saturated brine, and anhydrous magnesium sulfate was added for drying. The resulting mixture was gravity-filtered and the filtrate was concentrated to give 16.8 g of a yellow-green oily substance in a yield of 82%. The obtained yellow-green oily substance was identified as N,N'-di(naphthalen-1-yl)-2,6-pyridinedicarboxamidine, which was an intermediate, by electron impact-mass spectrometry (EI-MS) and nuclear magnetic resonance (NMR) spectroscopy. The synthesis scheme (b-1) of the step 2 is shown below.

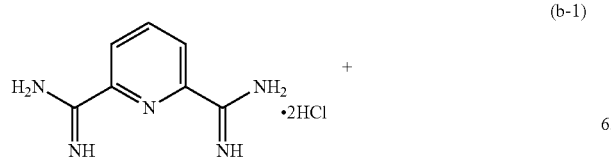

(b-1)

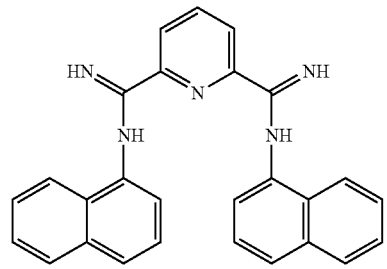

Step 3: Synthesis of 2,2'-(pyridine-2,6-diyl)bis(4-phenylbenzo[h]quinazoline) (abbreviation: 2,6(P-Bqn)2Py)

First, 16.8 g of N,N'-di(naphthalen-1-yl)-2,6-pyridinedicarboxamidine and 25 mL of benzaldehyde were put into a 500-mL recovery flask, and the mixture was heated under a nitrogen stream at 185° C. for 1.5 hours. After the reaction, the mixture was purified by silica column chromatography. A mixed solvent of toluene and ethyl acetate in a ratio of 5:1 was used as the developing solvent. A fraction of the desired substance was concentrated to give a solid. Ethyl acetate was added to the obtained solid. The mixture was irradiated with ultrasonic waves, and the lump was crushed into pieces and then suction filtered to give a yellow solid. This yellow solid was recrystallized with toluene to give 3.8 g of a yellow solid in a yield of 13%. The obtained yellow solid was identified as a dihydro body of the desired substance by NMR. Then, 2.0 g (3.3 mmol) of this dihydro body and 100 mL of xylene were added to a 500-mL three-neck flask. To this mixture was added 3.3 g (13.2 mmol) of p-chloranil and the mixture was heated under a nitrogen stream at 160° C. for 8 hours. Toluene was added to the reaction mixture, and the mixture was suction filtered through Celite (produced by Wako Pure Chemical Industries, Ltd., Catalog No. 531-16855). The obtained filtrate was concentrated to give a solid. Acetone was added to the obtained solid. The mixture was irradiated with ultrasonic waves, and the lump was crushed into pieces and then suction filtered to give a solid. The obtained solid was recrystallized with toluene to give 1.4 g of a white solid in a yield of 73%. By a train sublimation method, 1.4 g of the obtained white solid was purified under a pressure of $3.5 \times 10^{-3}$ Pa at 300° C. for 6 hours. After the sublimation purification, 0.675 g of a white solid was obtained at a collection rate of 50%. The synthesis scheme (c-1) of the step 3 is shown below.

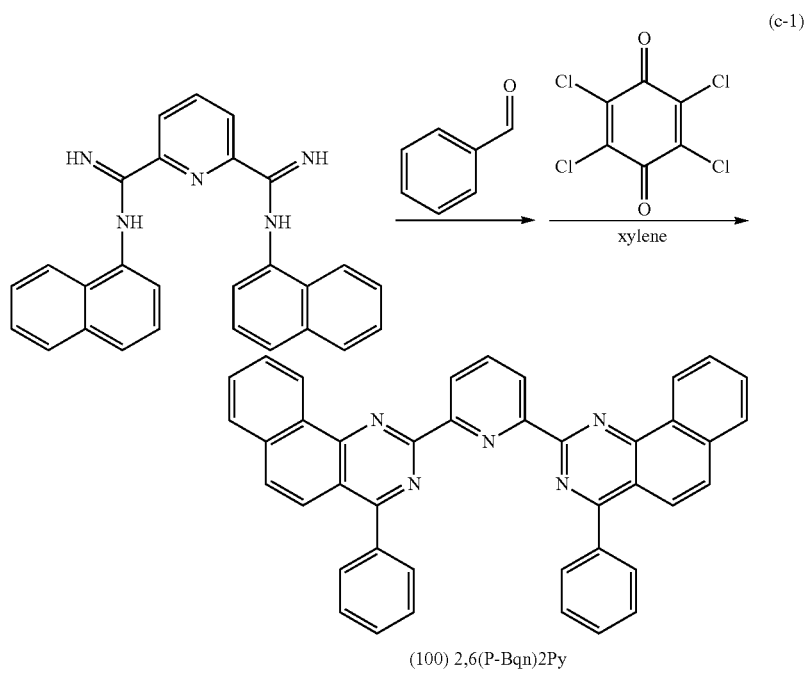

(100) 2,6(P-Bqn)2Py

Figure 13A:
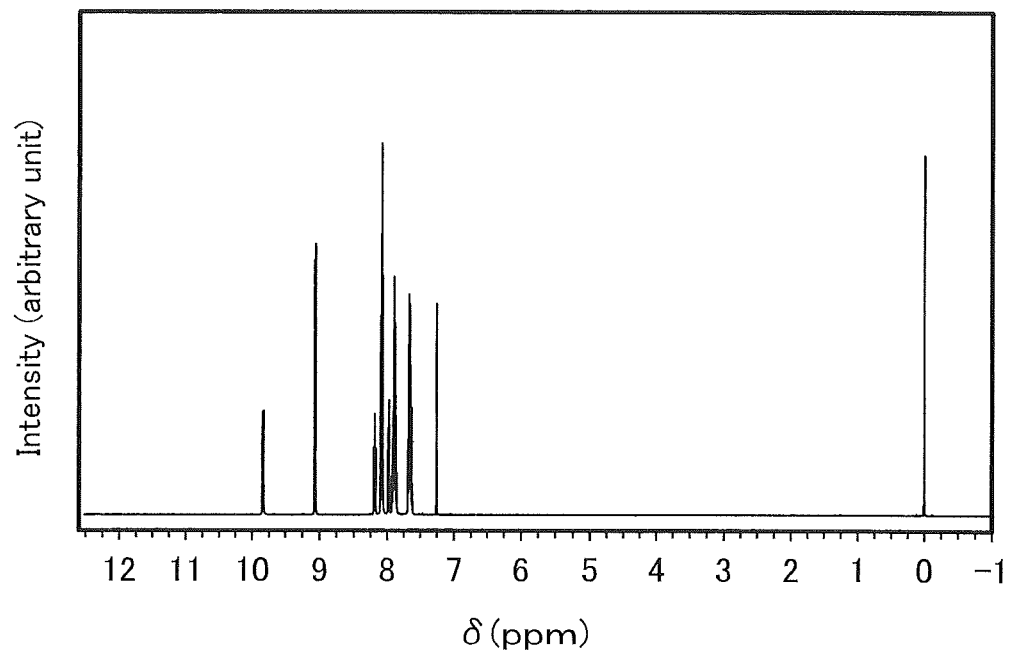
FIGS. 13A and 13B show $^1$H-NMR charts of 2,6(P-Bqn)2Py.
Figure 13B:
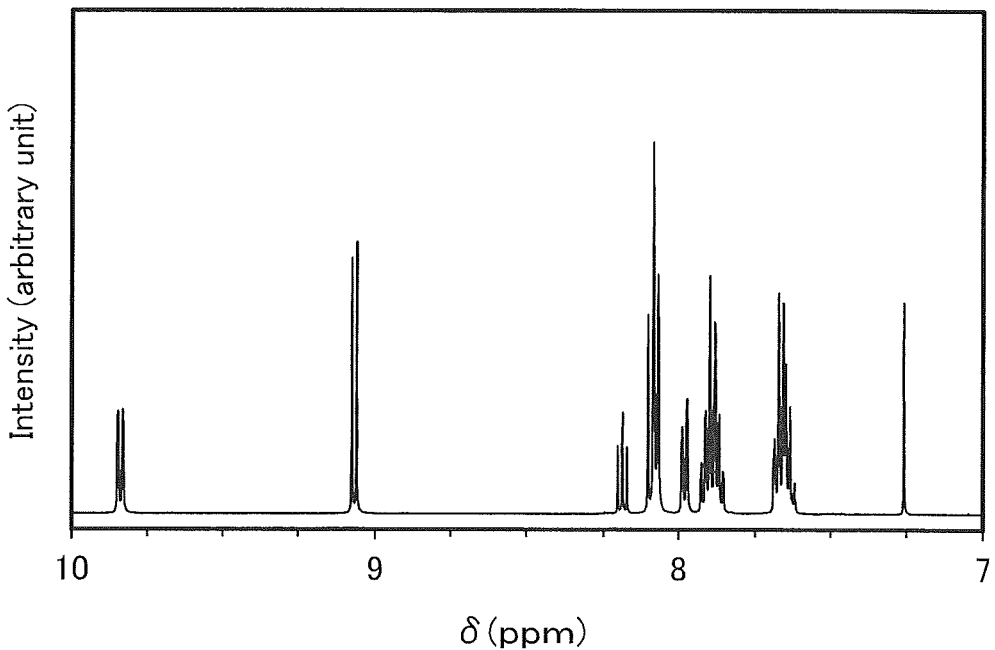

Protons ($^1$H) of the white solid which was obtained through the step 3 described above was measured by nuclear magnetic resonance (NMR) spectroscopy. The obtained values are shown below. FIGS. 13A and 13B show the $^1$H-NMR charts. FIG. 13B is a chart where the range of from 7 ppm to 10 ppm in FIG. 13A is enlarged. These results reveal that 2,6(P-Bqn)2Py, which is the organic compound of one embodiment of the present invention and represented by the above structural formula (100), was obtained in this synthesis example.

$^1$H-NMR δ (CDCl$_3$): 7.62-7.69 (m, 6H), 7.86-7.93 (m, 6H), 7.98 (d, 2H), 8.07-8.10 (m, 6H), 8.19 (t, 1H), 9.07 (d, 2H), 9.84 (d, 2H)

Next, 2,6(P-Bqn)2Py obtained was analyzed by liquid chromatography mass spectrometry (LC/MS).

In the LC/MS analysis, liquid chromatography (LC) separation was carried out with ACQUITY UPLC® (manufactured by Waters Corporation) and mass spectrometry (MS) analysis was carried out with Xevo G2 Tof MS (manufactured by Waters Corporation). ACQUITY UPLC® BEH C8 (2.1×100 mm, 1.7 μm) was used as a column for the LC separation, and the column temperature was 40° C. Acetonitrile was used for Mobile Phase A and a 0.1% formic acid aqueous solution was used for Mobile Phase B. Furthermore, a sample was prepared in such a manner that 2,6(P-Bqn)2Py was dissolved in chloroform at a given concentration and the solution was diluted with acetonitrile. The injection amount was 5.0 μL.

In the LC separation, a gradient method in which the composition of mobile phases is changed was employed. The ratio of Mobile Phase A to Mobile Phase B was 50:50 for 0 to 1 minute after the start of the measurement, and then the composition was changed such that the ratio of Mobile Phase A to Mobile Phase B after 10 minutes from the start of the measurement was 95:5. The composition was changed linearly.

In the MS analysis, ionization was carried out by an electrospray ionization (ESI) method. At this time, the capillary voltage and the sample cone voltage were set to 3.0 kV and 30 V, respectively, and detection was performed in a positive mode. A component with m/z of 588.22 which underwent the ionization under the above-described conditions was collided with an argon gas in a collision cell to dissociate into product ions. Energy (collision energy) for the collision with argon was 70 eV. The mass range for the measurement was m/z=100 to 1200. The detection results of the dissociated product ions by time-of-flight (TOF) MS are shown in FIG. 14.

Figure 14:
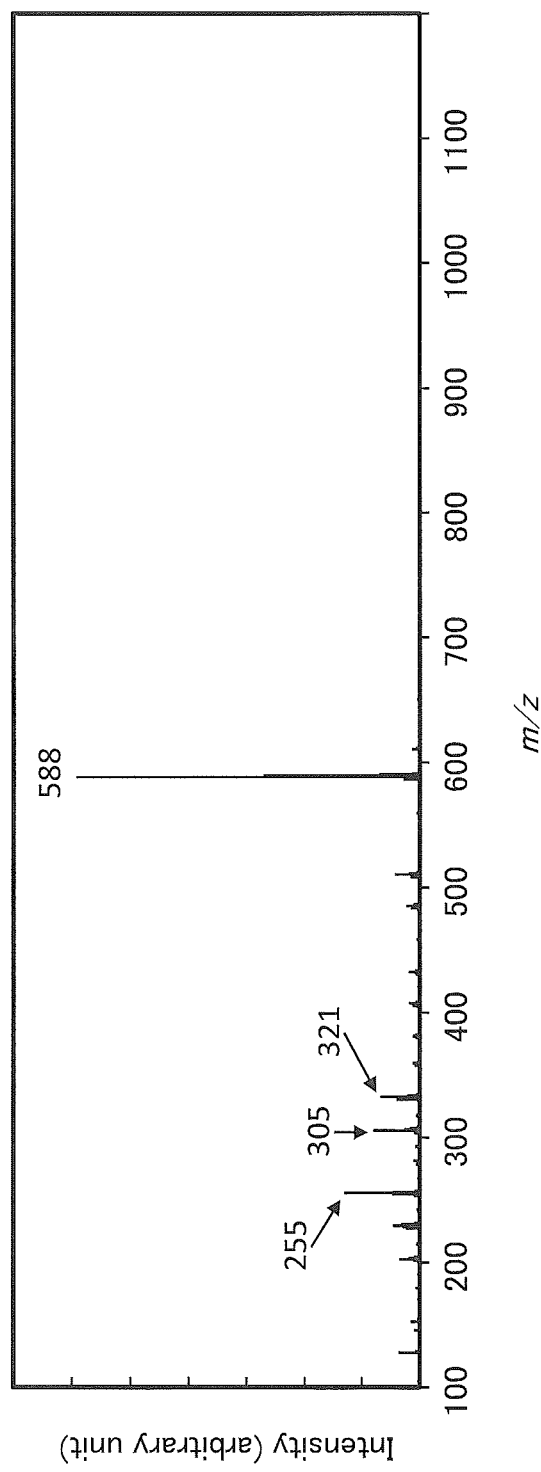
FIG. 14 shows results of LC/MS analysis of 2,6(P-Bqn)2Py.

FIG. 14 shows that product ions of 2,6(P-Bqn)2Py are mainly detected around m/z=321, 305, and 255. The results in FIG. 14 show characteristics derived from 2,6(P-Bqn)2Py and therefore can be regarded as important data for identifying 2,6(P-Bqn)2Py contained in a mixture.

It can be presumed that the product ions around m/z=321 and m/z=305 are cations generated due to cleavage of a pyrimidine ring in 2,6(P-Bqn)2Py and the product ion around m/z=255 is a cation in a state where 2-(pyridin-2-yl)(4-phenylbenzo[h]quinazoline) is eliminated from 2,6(P-Bqn)2Py and includes 4-phenylbenzo[h]quinazoline. These results suggest that 2,6(P-Bqn)2Py includes 4-phenylbenzo[h]quinazoline.

Example 2

Synthesis Example 2

In this example, a method of synthesizing 2,2'-(pyridine-2,6-diyl)bis[4-(2-naphthyl)benzo[h]quinazoline] (abbreviation: 2,6(N-Bqn)2Py), which is represented by the structural formula (101) in Embodiment 1, is described. The structure of 2,6(N-Bqn)2Py is shown below.

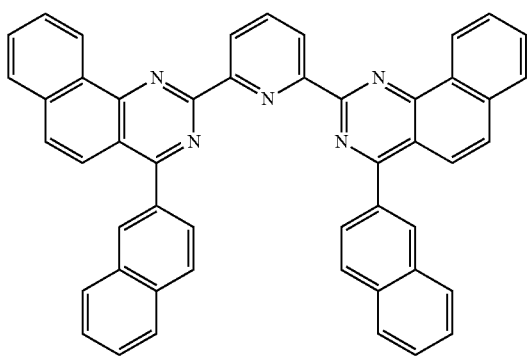

(101) 2,6(N-Bqn)2Py

Step 1: Synthesis of 2,6-pyridinedicarboxamidine dihydrochloride

This step is similar to the step 1 in Synthesis example 1 of Example 1.

Step 2: Synthesis of N,N'-di(naphthalen-1-yl)-2,6-pyridinedicarboxamidine

This step is similar to the step 2 in Synthesis example 1.

Step 3: Synthesis of 2,2'-(pyridine-2,6-diyl)bis[4-(2-naphthyl)benzo[h]quinazoline] (abbreviation: 2,6(N-Bqn)2Py)

First, 0.93 g of N,N'-di(naphthalen-1-yl)-2,6-pyridinedicarboxamidine and 3.3 g (21 mmol) of 2-naphthoaldehyde were put into a 300-mL recovery flask, and the mixture was heated under a nitrogen stream at 190° C. for 3 hours. The reaction mixture was purified by silica column chromatography. As the developing solvent, dichloromethane, a solvent of dichloromethane and ethyl acetate in a ratio of 5:1, and a solvent of dichloromethane and ethyl acetate in a ratio of 1:1 were used in this order. The obtained fraction of the desired substance was concentrated to give a yellow solid. The synthesis scheme (c-2) of the step 3 is shown below.

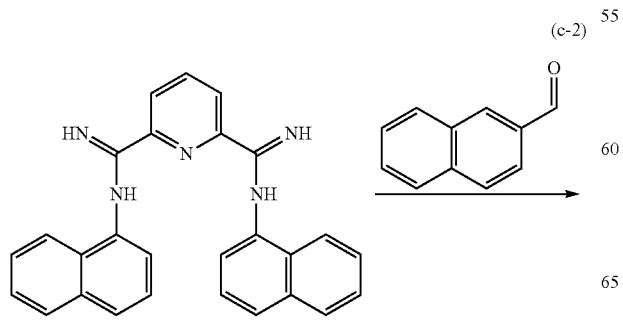

(c-2)

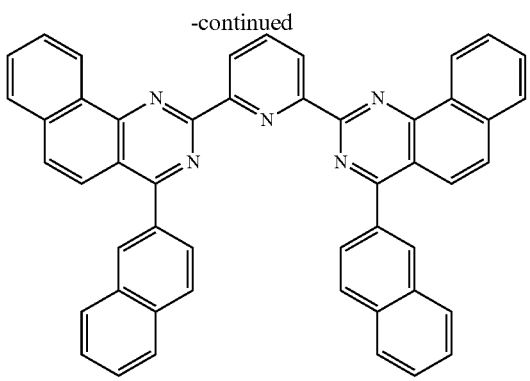

(101) 2,6(N-Bqn)2Py

Figure 15A:
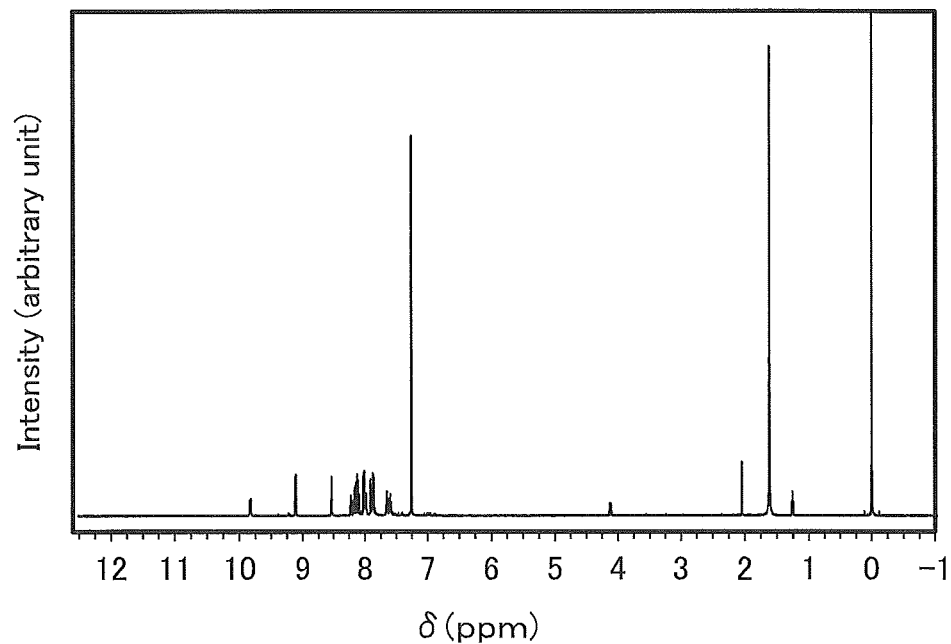
FIGS. 15A and 15B show $^1$H-NMR charts of 2,6(N-Bqn)2Py.
Figure 15B:
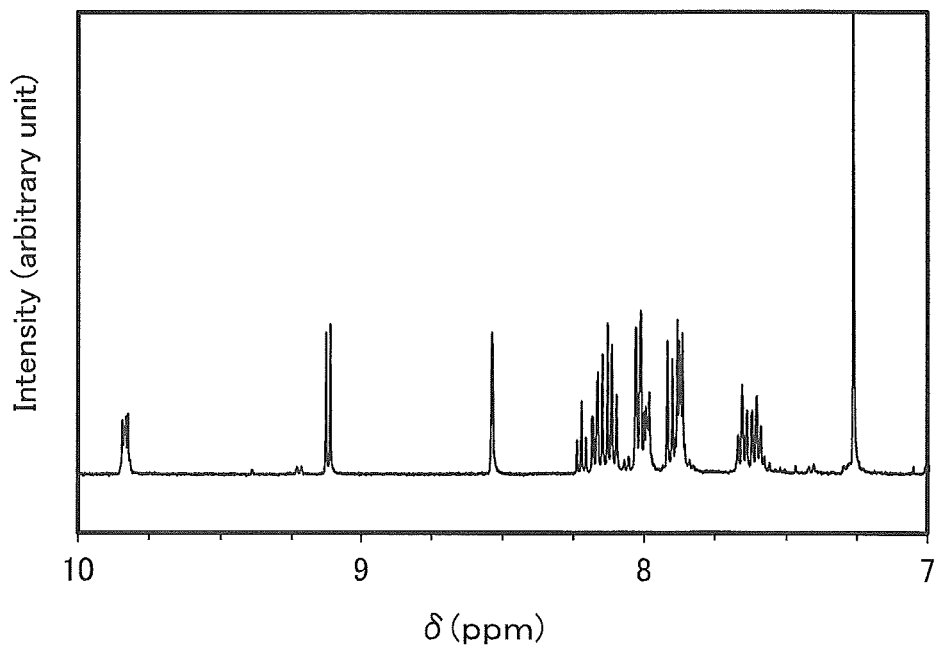

Protons ($^1$H) of the yellow solid which was obtained through the step 3 described above was measured by nuclear magnetic resonance (NMR) spectroscopy. The obtained values are shown below. FIGS. 15A and 15B show the $^1$H-NMR charts. FIG. 15B is a chart where the range of from 7 ppm to 10 ppm in FIG. 15A is enlarged. These reveal that 2,6(N-Bqn)2Py of the present invention, which is represented by the structural formula (101), was obtained in this synthesis example.

$^1$H-NMR δ (CDCl$_3$): 7.56-7.67 (m, 4H), 7.82-8.24 (m, 19H), 8.54 (s, 21-1), 9.12 (d, 2H), 9.82-9.84 (m, 2H)

Example 3

In this example, a light-emitting element 1 containing 2,2'-(pyridine-2,6-diyl)bis(4-phenylbenzo[h]quinazoline) (abbreviation: 2,6(P-Bqn)2Py), which is represented by the structural formula (100) in Embodiment 1 and is synthesized in Synthesis example 1, and a comparative light-emitting element 1 containing 2,2'-(pyridine-2,6-diyl)bis(4,6-diphenyl pyrimidine) (abbreviation: 2,6(P2Pm)2Py) are described. Structure formulae of organic compounds used in the light-emitting element 1 and the comparative light-emitting element 1 are shown below.

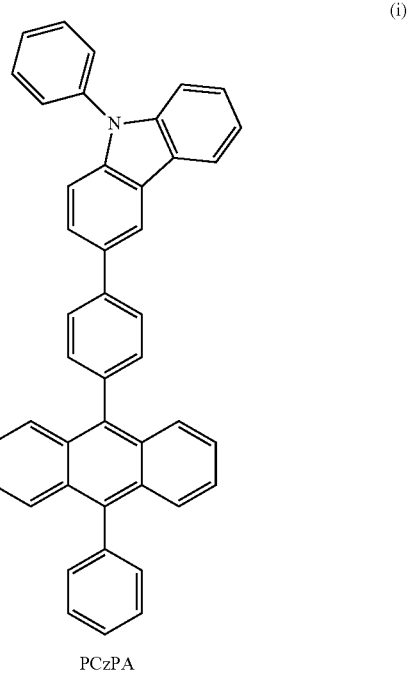

(i)

PCzPA

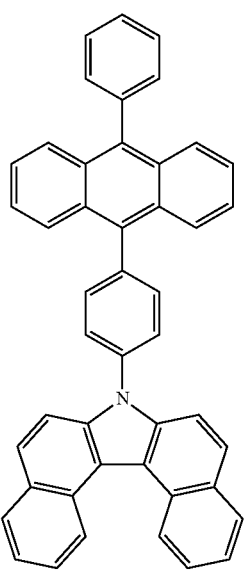

egDBCzPA

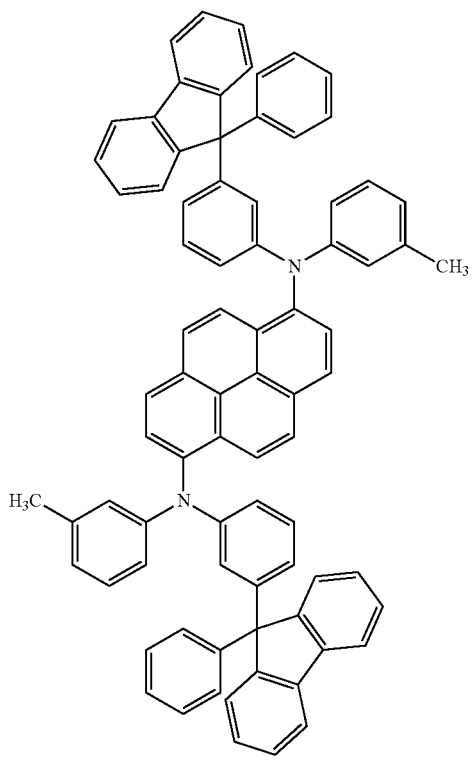

1,6mMemFLPAPrn

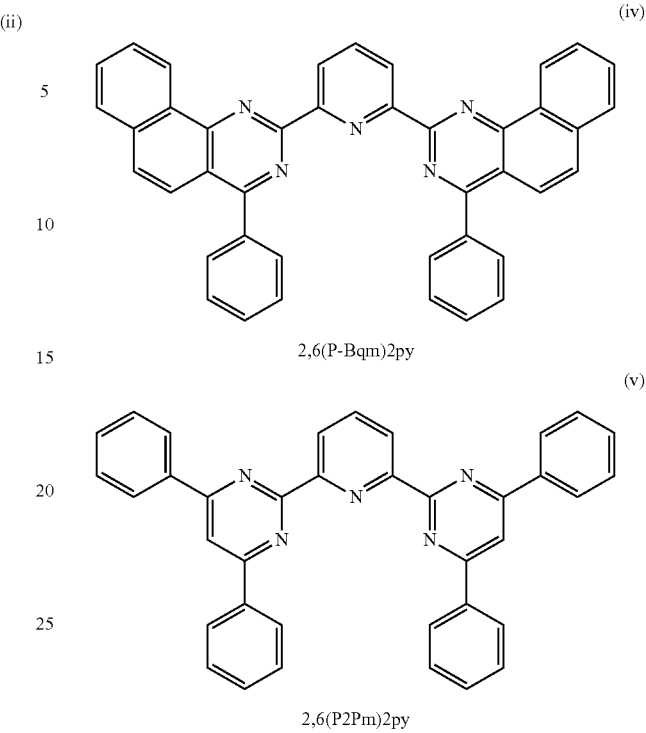

2,6(P-Bqm)2py 2,6(P2Pm)2py (Method of Fabricating Light-Emitting Element 1)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 functions as an anode of the light-emitting element.

Next, as pretreatment for forming the light-emitting element over the substrate, UV-ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate over which the first electrode 101 was formed was fixed to a substrate holder provided in the vacuum evaporation apparatus so that the surface on which the first electrode 101 was formed faced downward. Over the first electrode 101, 9-phenyl-3-[4-(10-phenyl-9-anthryl)phenyl]-9H-carbazole (abbreviation: PCzPA) represented by the above structural formula (i) and molybdenum(VI) oxide were deposited by co-evaporation by an evaporation method using resistance heating, so that the hole-injection layer 111 was formed. The thickness of the hole-injection layer 111 was set to 60 nm, and the weight ratio of PCzPA to molybdenum oxide was adjusted to 4:2 (=PCzPA:molybdenum oxide). Note that the co-evaporation method refers to an evaporation method in which evaporation is carried out from a plurality of evaporation sources at the same time in one treatment chamber.

Next, a film of PCzPA was formed to a thickness of 10 nm over the hole-injection layer 111 to form the hole-transport layer 112.

Furthermore, over the hole-transport layer 112, the light-emitting layer 113 was formed by co-evaporation of 7-[4-(10-phenyl-9-anthryl)phenyl]-7H-dibenzo[c,g]carbazole (abbreviation: cgDBCzPA) represented by the above structural formula (ii) and N,N'-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) in a weight ratio of 1:0.03 (=cgDBCzPA: 1,6mMemFLPAPrn) to a thickness of 25 mm.

Then, the electron-transport layer 114 and the electron-injection layer 115 were formed over the light-emitting layer 113 in such a manner that a 25 nm thick film of 2,6(P-Bqn)2Py represented by the above structural formula (iv) was formed.

After the formation of the electron-transport layer 114 and the electron-injection layer 115, lithium fluoride (LiF) was deposited by evaporation to a thickness of 1 nm and aluminum was deposited by evaporation to a thickness of 200 nm to form the second electrode 102. Thus, the light-emitting element 1 in this example was fabricated.

(Method of Fabricating Comparative Light-Emitting Element 1)

The comparative light-emitting element 1 was fabricated in the same manner as the light-emitting element 1 except for changing 2,6(P-Bqn)2Py in the electron-transport layer of the light-emitting element 1 to 2,6(P2Pm)2Py represented by the above structural formula (v).

The element structures of the light-emitting element 1 and the comparative light-emitting element 1 are shown in a table below.

The light-emitting element 1 and the comparative light-emitting element 1 were each sealed using a glass substrate in a glove box containing a nitrogen atmosphere so as not to be exposed to the air (specifically, a sealing material was applied to surround the elements and UV treatment and heat treatment at 80° C. for 1 hour were performed at the time of sealing). Then, initial characteristics and reliability of these light-emitting elements were measured. Note that the measurements were carried out at room temperature (in an atmosphere kept at 25° C.).

Figure 16:
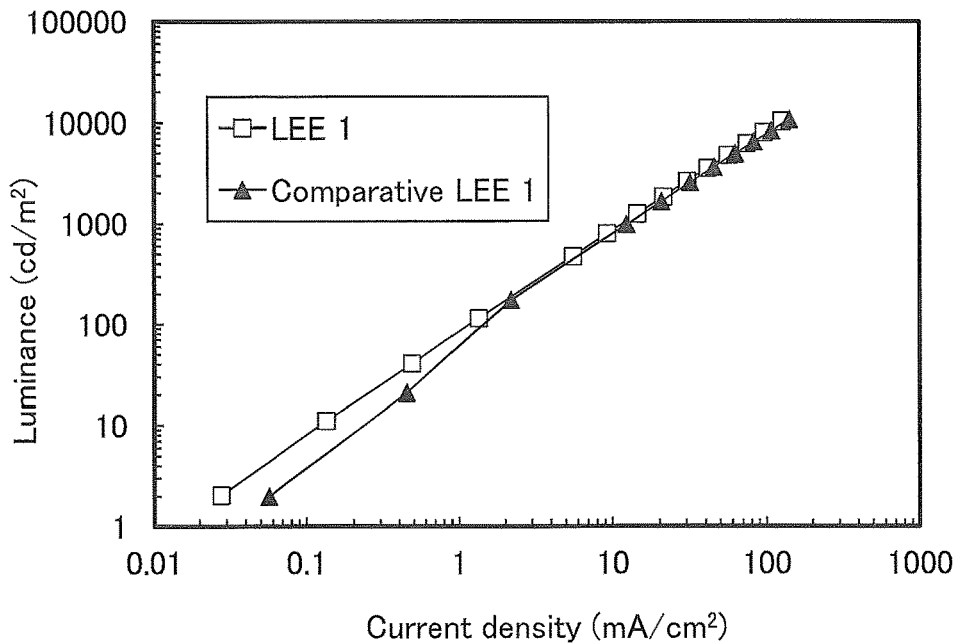
FIG. 16 shows luminance-current density characteristics of a light-emitting element 1 (abbreviation: LEE 1) and a comparative light-emitting element 1 (abbreviation: Comparative LEE 1).
Figure 17:
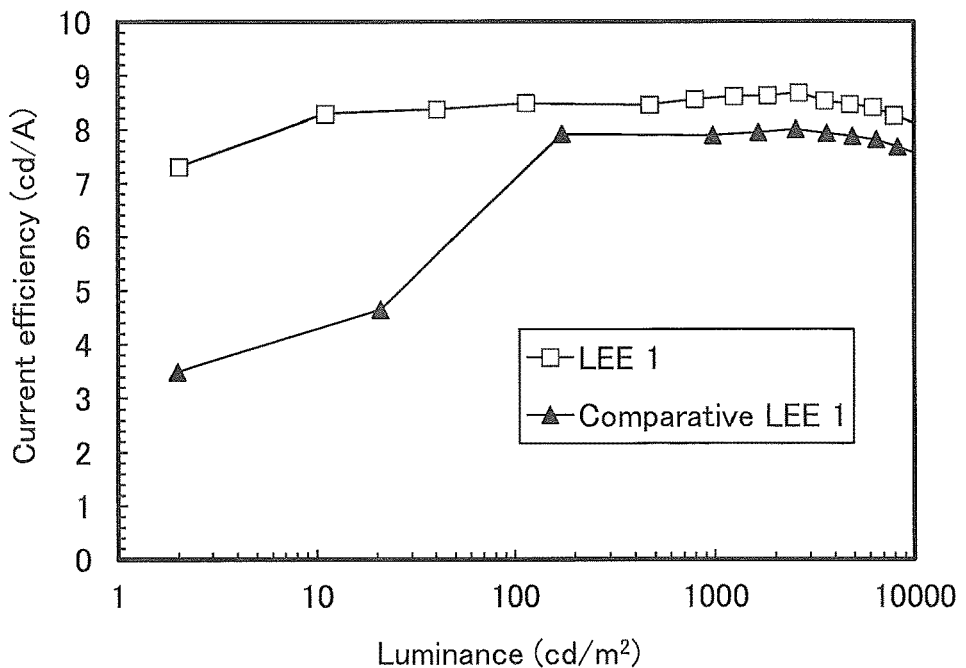
FIG. 17 shows current efficiency-luminance characteristics of the light-emitting element 1 and the comparative light-emitting element 1.
Figure 18:
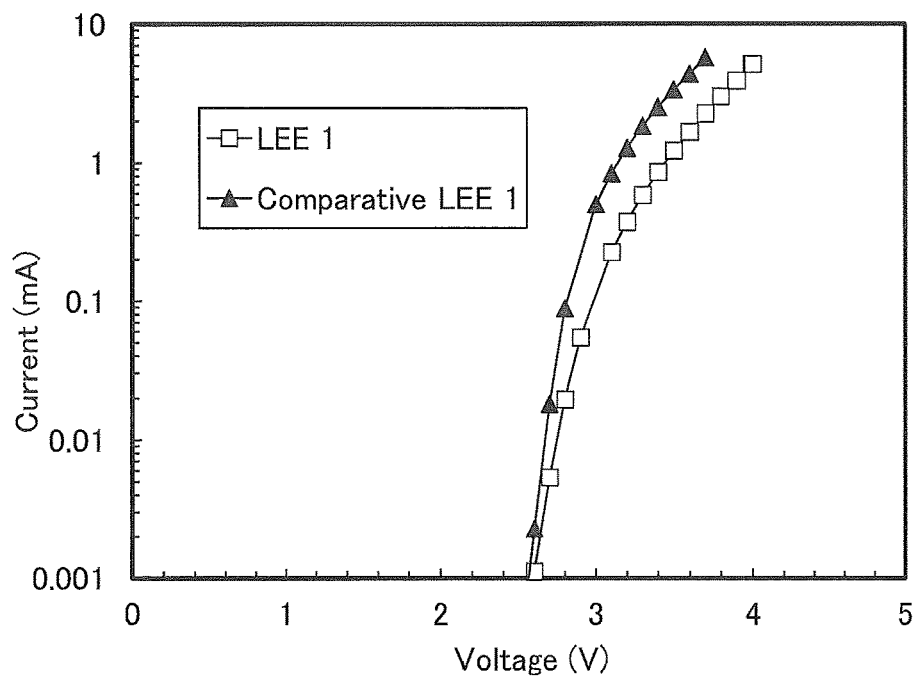
FIG. 18 shows current-voltage characteristics of the light-emitting element 1 and the comparative light-emitting element 1.
Figure 19:
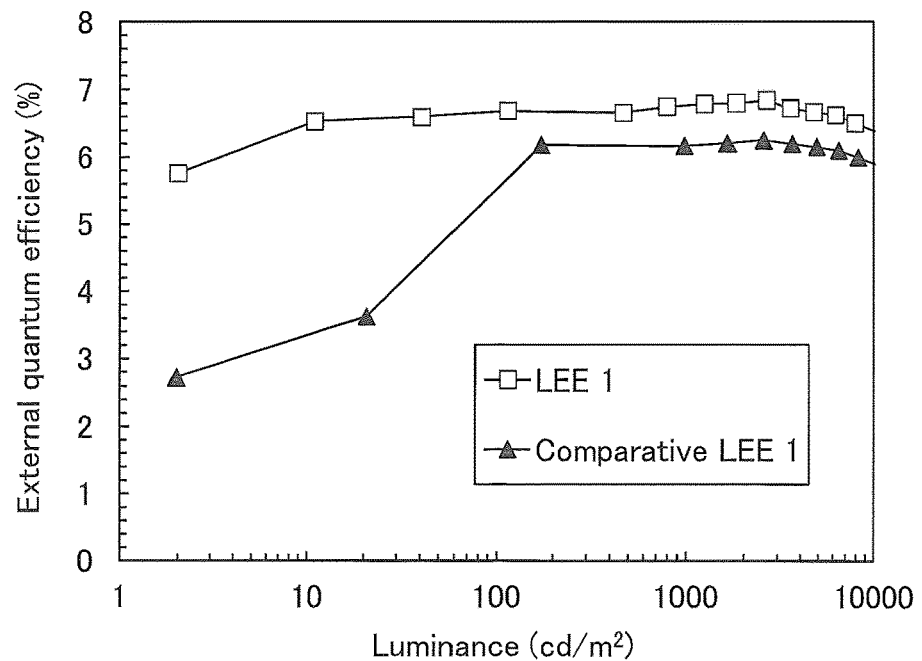
FIG. 19 shows external quantum efficiency-luminance characteristics of the light-emitting element 1 and the comparative light-emitting element 1.

FIG. 16 shows luminance-current density characteristics of the light-emitting element 1 and the comparative light-emitting element 1. FIG. 17 shows current efficiency-luminance characteristics thereof. FIG. 18 shows current-voltage characteristics thereof. FIG. 19 shows external quantum efficiency-luminance characteristics thereof. Table 2 shows main characteristics of the light-emitting elements at approximately 1000 cd/m².

TABLE 2

|  | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting element 1 | 3.2 | 0.37 | 9 | 0.14 | 0.17 | 8.5 | 6.7 |
| Comparative light-emitting element 1 | 3.0 | 0.50 | 12 | 0.14 | 0.18 | 7.9 | 6.2 |

It can be found from FIG. 16, FIG. 17, FIG. 18, FIG. 19, and Table 2 that each of the light-emitting elements is a blue light-emitting element with favorable characteristics.

Figure 20:
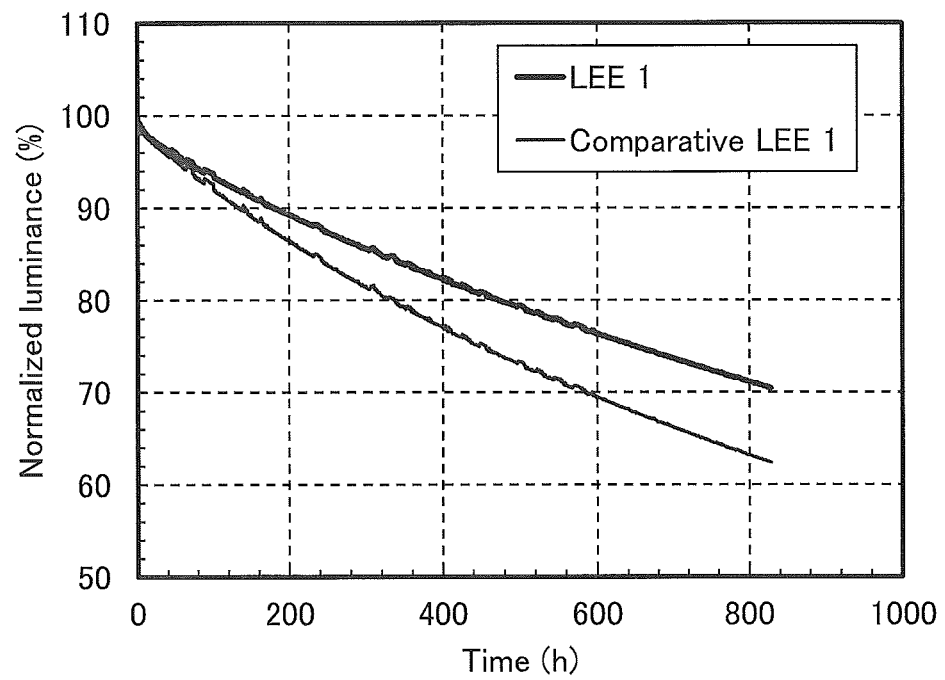
FIG. 20 shows characteristics of normalized luminance change with time of the light-emitting element 1 and the comparative light-emitting element 1.

FIG. 20 shows changes in luminance of the light-emitting elements with driving time under the conditions where the initial luminance was 5000 cd/m² and the current density was constant. As shown in FIG. 20, the light-emitting element 1, which is a light-emitting element of the present invention, shows higher reliability than the comparative light-emitting element 1. This means that a light-emitting element including the organic compound of one embodiment the present invention is highly reliable.

Furthermore, since 2,6(P-Bqn)2Py has high heat resistance because of its rigid skeleton and moderate molecular weight, the light-emitting element 1 including 2,6(P-Bqn)2Py has high heat resistance.

Example 4

In this example, a light-emitting element 2 containing 2,6(P-Bqn)2Py and a comparative light-emitting element 2 containing 2,6(P2Pm)2Py are described. The element structures of the light-emitting element 2 and the comparative

TABLE 1

| Hole-injection layer | Hole-transport layer | Light-emitting layer | Electron-transport layer and Electron-injection layer |
|---|---|---|---|
| PCzPA:MoOx 4:2 60 nm | PCzPA 10 nm | cgDBCzPA:1,6mMemFLPAPrn 1:0.03 25 nm | *1 25 nm |

*1 Light-emitting element 1: 2,6(P-Bqn)2Py Comparative light-emitting element 1: 2,6(P2Pm)2Py light-emitting element 2 are different from those of the light-emitting element 1 and the comparative light-emitting element 1. Structure formulae of organic compounds used in the light-emitting element 2 and the comparative light-emitting element 2 are shown below.
(i)
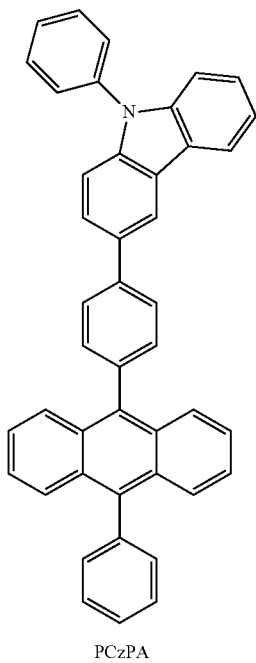
PCzPA
(ii)
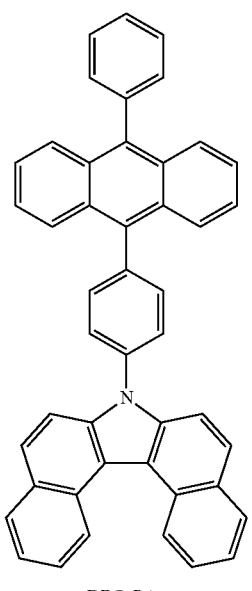
egDBCzPA
(iii)
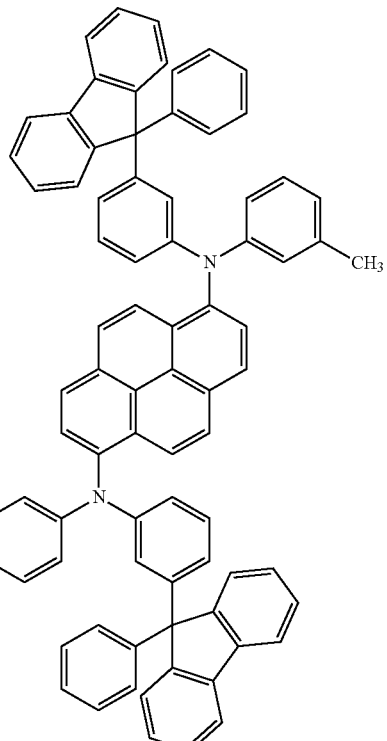
1,6mMemFLPAPrn
(iv)
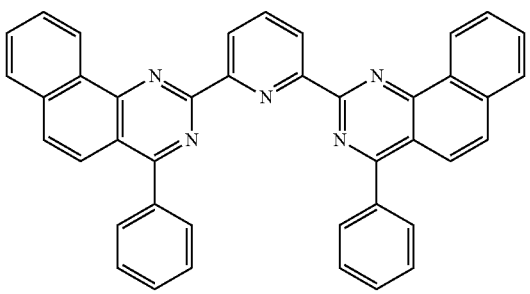
2,6(P-Bqn)2py
(v)
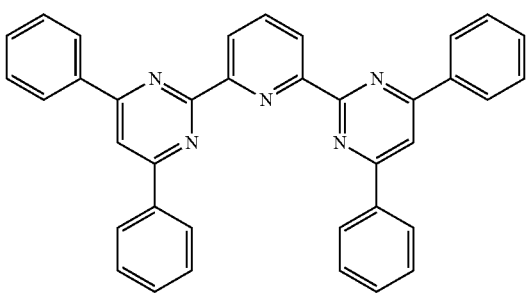
2,6(P2Pm)2py -continued (vi)

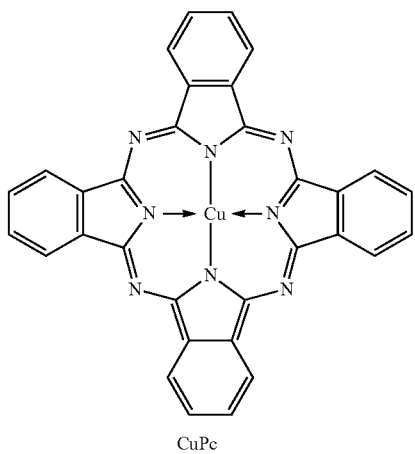

CuPc (Method of Fabricating Light-Emitting Element 2)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 functions as an anode of the light-emitting element.

Next, as pretreatment for forming the light-emitting element over the substrate, UV-ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate over which the first electrode 101 was formed was fixed to a substrate holder provided in the vacuum evaporation apparatus so that the surface on which the first electrode 101 was formed faced downward. Over the first electrode 101, 9-phenyl-3-[4-(10-phenyl-9-anthryl) phenyl]-9H-carbazole (abbreviation: PCzPA) represented by the above structural formula (i) and molybdenum(VI) oxide were deposited by co-evaporation by an evaporation method using resistance heating, so that the hole-injection layer 111 was formed. The thickness of the hole-injection layer 111 was set to 60 nm, and the weight ratio of PCzPA to molybdenum oxide was adjusted to 4:2 (=PCzPA:molybdenum oxide). Note that the co-evaporation method refers to an evaporation method in which evaporation is carried out from a plurality of evaporation sources at the same time in one treatment chamber.

Next, a film of PCzPA was formed to a thickness of 10 nm over the hole-injection layer 111 to form the hole-transport layer 112.

Furthermore, over the hole-transport layer 112, the light-emitting layer 113 was formed by co-evaporation of 7-[4-(10-phenyl-9-anthryl)phenyl]-7H-dibenzo[c,g]carbazole (abbreviation: cgDBCzPA) represented by the above structural formula (ii) and N,N-bis(3-methylphenyl)-N,N-bis[3-(9-phenyl-9H-fluoren-9-yl)phenyl]-pyrene-1,6-diamine (abbreviation: 1,6mMemFLPAPrn) represented by the above structural formula (iii) in a weight ratio of 1:0.03 cgDBCzPA: 1,6mMemFLPAPrn) to a thickness of 25 nm.

Then, the electron-transport layer 114 was formed over the light-emitting layer 113 in such a manner that a 25 nm thick film of 2,6(P-Bqn)2Py represented by the structural formula (iv) was formed.

After the formation of the electron-transport layer 114, an electron-injection buffer layer was formed by evaporation of lithium oxide ($Li_2O$) to a thickness of 0.1 nm, and an electron-relay layer was formed by deposition of copper phenanthroline (abbreviation: CuPc) represented by the above structural formula (vi) to a thickness of 2 nm. Then, a p-type layer was formed by co-evaporation of PCzPA and molybdenum oxide to a thickness of 20 nm. The weight ratio of PCzPA to molybdenum oxide was adjusted to 4:2. Note that the electron-injection buffer layer, the electron-relay layer, and the p-type layer may be collectively referred to as a charge-generation layer in some cases.

Lastly, aluminum was deposited by evaporation to a thickness of 200 nm to form the second electrode 102 functioning as a cathode. Thus, the light-emitting element 2 in this example was fabricated.

(Method of Fabricating Comparative Light-Emitting Element 2)

The comparative light-emitting element 2 was fabricated in the same manner as the light-emitting element 2 except for changing 2,6(P-Bqn)2Py in the electron-transport layer of the light-emitting element 2 to 2,6(P2Pm)2Py.

The element structures of the light-emitting element 2 and the comparative light-emitting element 2 are shown in a table below.

TABLE 3

| Hole-injection layer | Hole-transport layer | Light-emitting layer | Electron-transport layer | Electron-injection buffer layer | Electron-relay layer | p-Type layer |
|---|---|---|---|---|---|---|
| PCzPA:MoOx 4:2 | PCzPA | cgDBCzPA:1,6mMemFLPAPrn 1:0.03 | *2 | $Li_2O$ | CuPc | PCzPA:MoOx 4:2 |
| 60 nm | 10 nm | 25 nm | 25 nm | 0.1 nm | 2 nm | 20 nm |

*2 Light-emitting element 2: 2,6(P-Bqn)2Py
Comparative light-emitting element 2: 2,6(P2Pm)2Py The light-emitting element 2 and the comparative light-emitting element 2 were each sealed using a glass substrate in a glove box containing a nitrogen atmosphere so as not to be exposed to the air (specifically, a sealing material was applied to surround the elements and UV treatment and heat treatment at 80° C. for 1 hour were performed at the time of sealing). Then, initial characteristics and reliability of these light-emitting elements were measured. Note that the measurements were carried out at room temperature (in an atmosphere kept at 25° C.).

Figure 21:
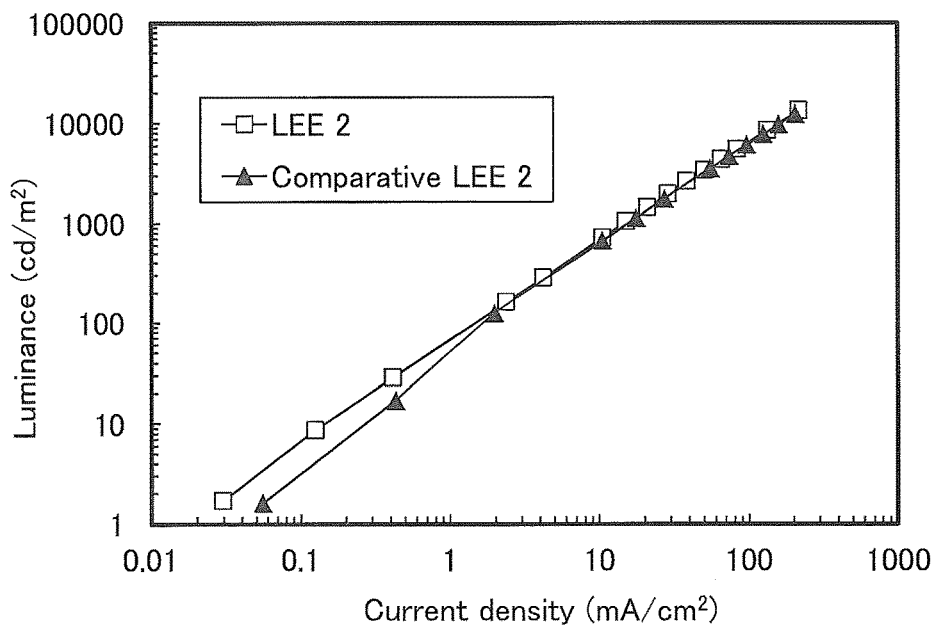
FIG. 21 shows luminance-current density characteristics of a light-emitting element 2 (abbreviation: LEE 2) and a comparative light-emitting element 2 (abbreviation: Comparative LEE 2).
Figure 22:
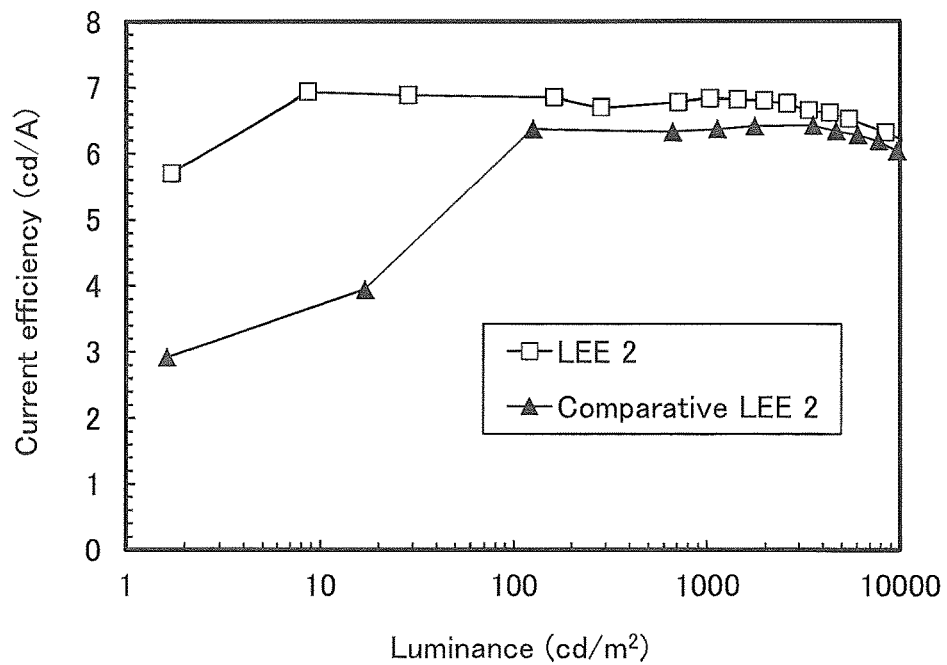
FIG. 22 shows current efficiency-luminance characteristics of the light-emitting element 2 and the comparative light-emitting element 2.
Figure 23:
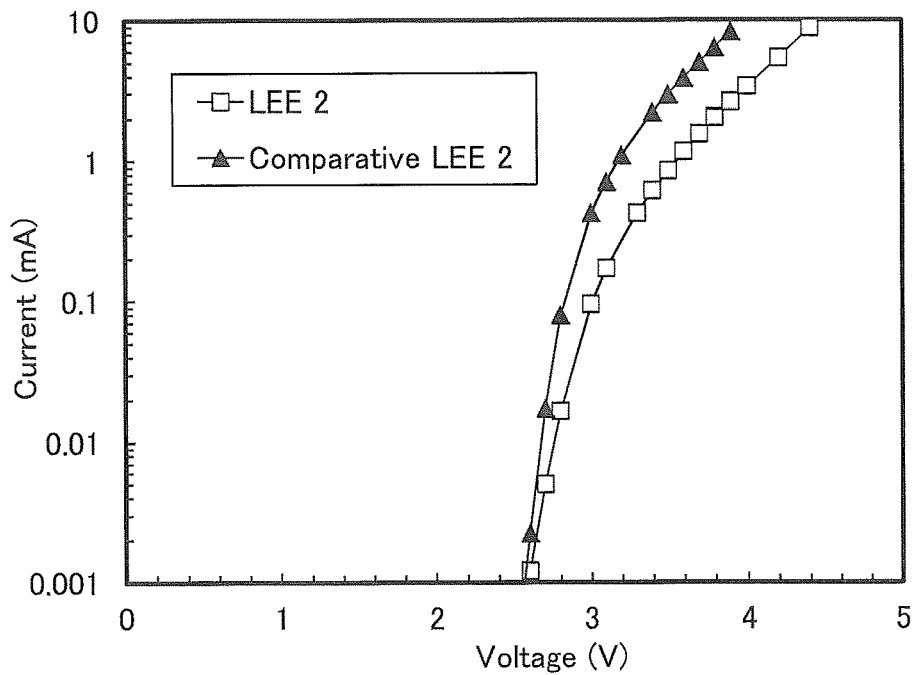
FIG. 23 shows current-voltage characteristics of the light-emitting element 2 and the comparative light-emitting element 2.
Figure 24:
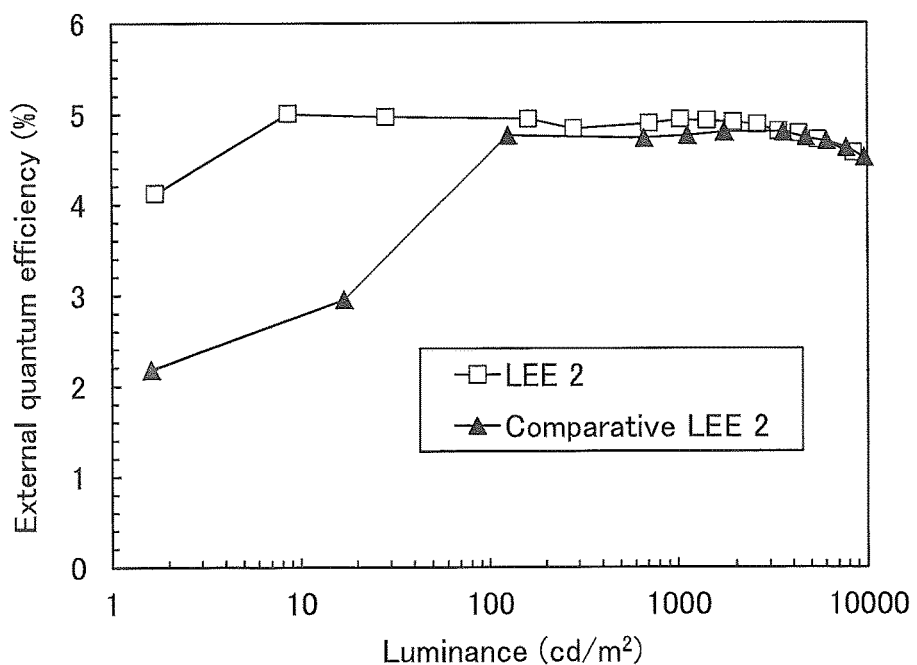
FIG. 24 shows external quantum efficiency-luminance characteristics of the light-emitting element 2 and the comparative light-emitting element 2.

FIG. 21 shows luminance-current density characteristics of the light-emitting element 2 and the comparative light-emitting element 2. FIG. 22 shows current efficiency-luminance characteristics thereof. FIG. 23 shows current-voltage characteristics thereof. FIG. 24 shows external quantum efficiency-luminance characteristics thereof. Table 4 shows main characteristics of the light-emitting elements at approximately 1000 cd/m².

TABLE 4

|  | Voltage (V) | Current (mA) | Current density (mA/cm²) | Chromaticity x | Chromaticity y | Current efficiency (cd/A) | External quantum efficiency (%) |
| --- | --- | --- | --- | --- | --- | --- | --- |
| Light-emitting element 2 | 3.4 | 0.61 | 15 | 0.14 | 0.21 | 6.8 | 4.9 |
| Comparative light-emitting element 2 | 3.1 | 0.71 | 18 | 0.14 | 0.19 | 6.4 | 4.8 |

It can be found from FIG. 21, FIG. 22, FIG. 23, FIG. 24, and Table 4 that the light-emitting element 2 is a blue light-emitting element with favorable characteristics.

Figure 25:
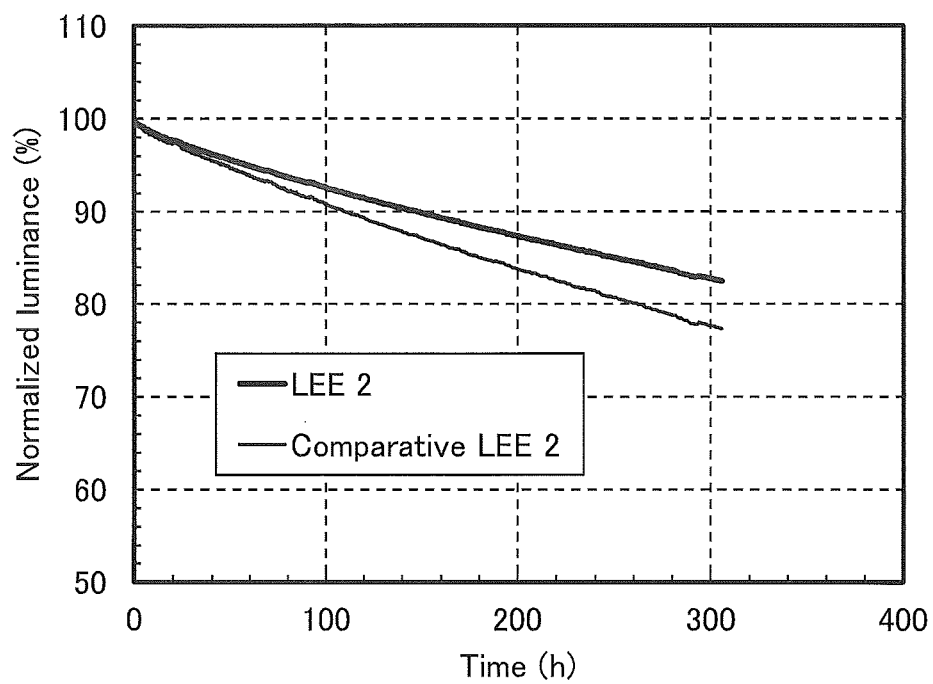
FIG. 25 shows characteristics of normalized luminance change with time of the light-emitting element 2 and the comparative light-emitting element 2.

FIG. 25 shows changes in luminance of the light-emitting elements with driving time under the conditions where the initial luminance was 5000 cd/m² and the current density was constant. As shown in FIG. 25, the light-emitting element 2, which is a light-emitting element of the present invention, is highly reliable. This means that a light-emitting element including the organic compound of one embodiment the present invention is highly reliable.

Furthermore, since 2,6(P-Bqn)2Py has high heat resistance because of its rigid skeleton and moderate molecular weight, the light-emitting element 2 including 2,6(P-Bqn)2Py can have high heat resistance.

The charge-generation layer provided in the light-emitting element 2 has a structure similar to a charge-generation layer provided between light-emitting units in a tandem light-emitting element. That is, a tandem light-emitting element can have a long lifetime like the light-emitting element 2 when a layer in contact with the anode side of the charge-generation layer contains the organic compound of the present invention.

Example 5

In this example, results of examining the effect of reducing the crosstalk in a light-emitting device including the organic compound of one embodiment of the present invention are described. A passive panel having a top emission structure was used for evaluation of the crosstalk. This panel has a display region that is 3.93 inches diagonal, a resolution of 457.6 ppi, a pixel size of 18.5 μm×55.5 μm, and an aperture ratio of 48.5%. The pixels have a stripe structure and can emit light individually. The crosstalk was evaluated by making only pixels of a single color in one column emit light and examining how much light was emitted from pixels to which no electric field was applied and which were near the pixels that were made to emit light.

Structural formulae of organic compounds used in light-emitting elements of a light-emitting device 1, a comparative light-emitting device 1, and a comparative light-emitting device 2, which were fabricated in this example, are shown below.

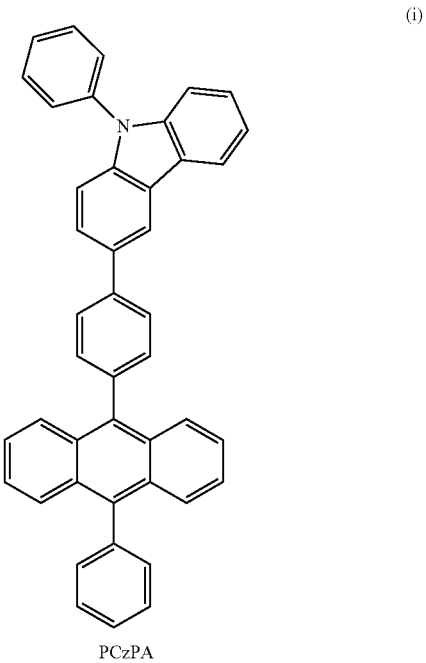

(i)

PCzPA

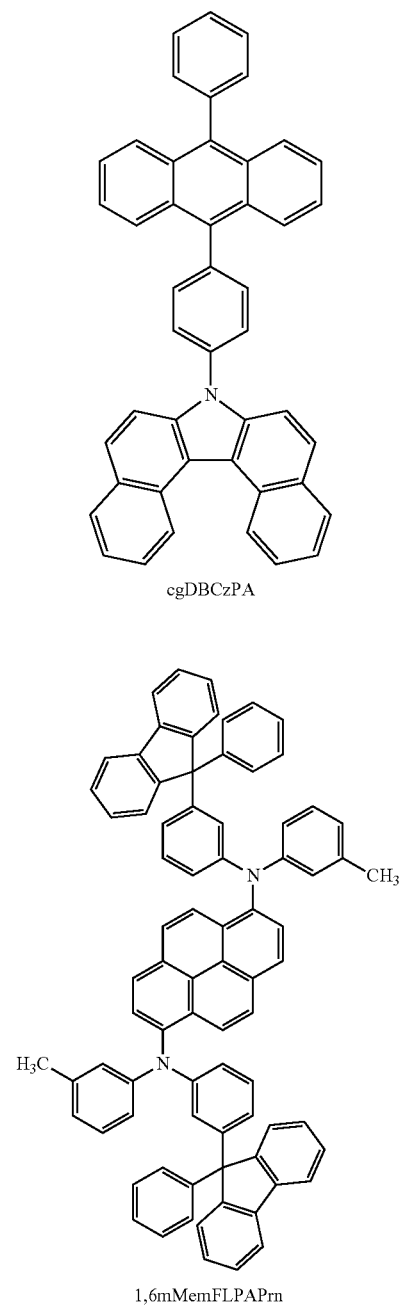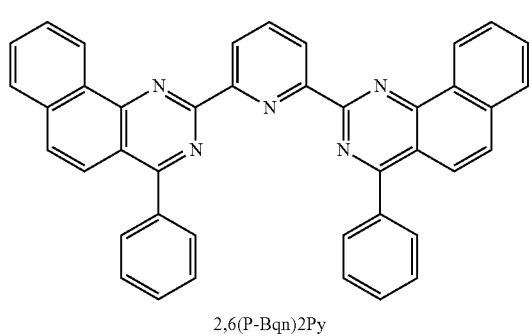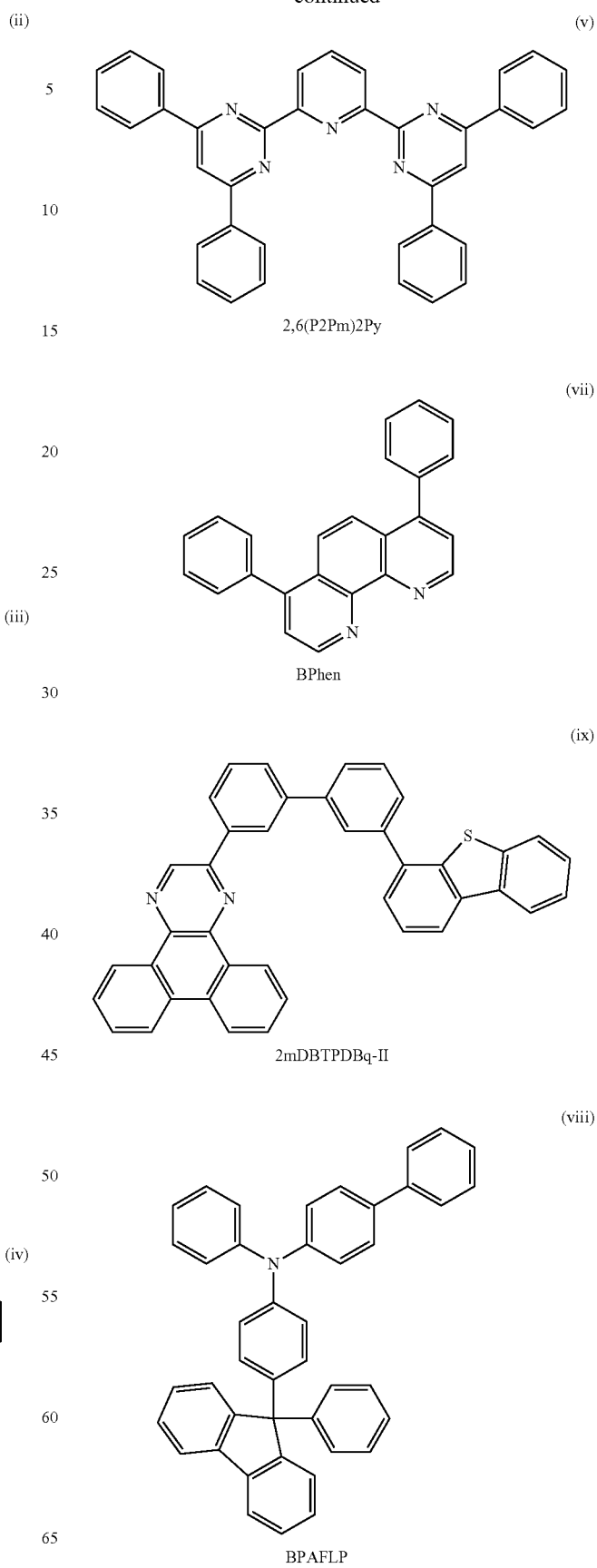

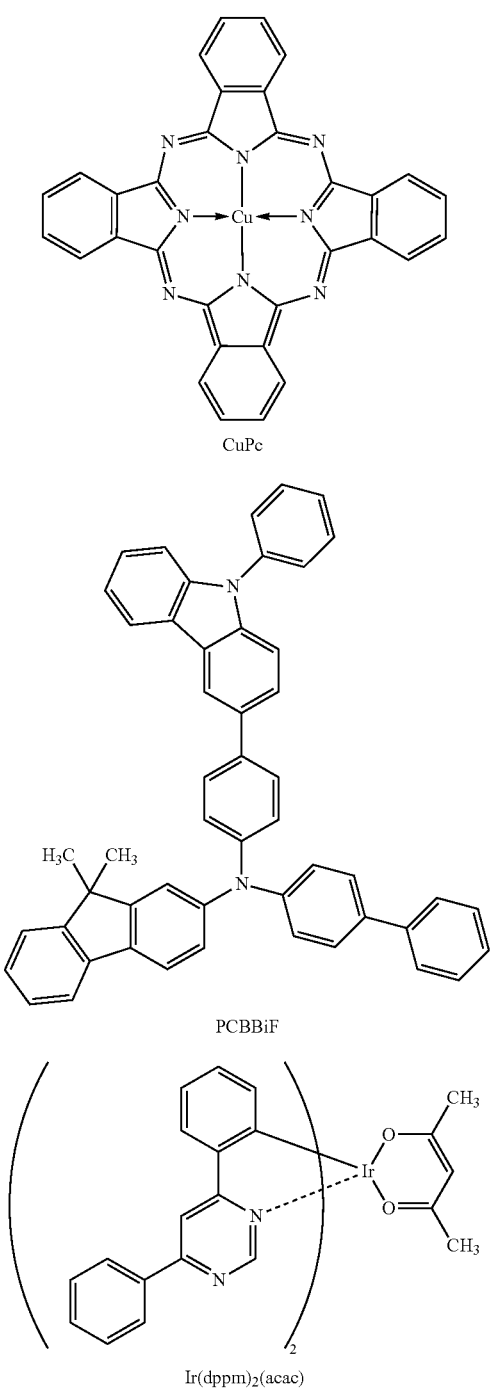

Figure 27:
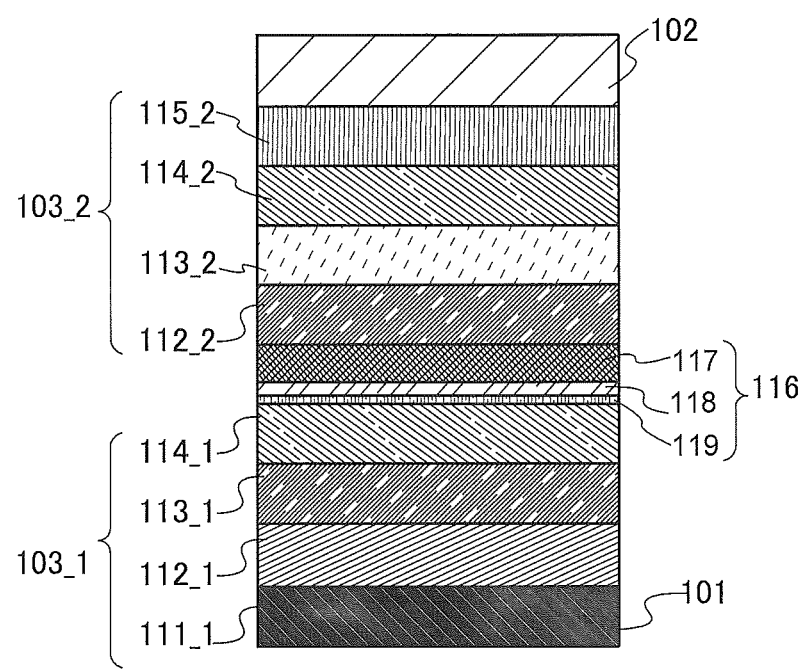
FIG. 27 is a schematic diagram of a tandem light-emitting element.

A method of fabricating a light-emitting element in the light-emitting device 1, which was fabricated in this example, is described with reference to FIG. 27. As the first electrode 101, an aluminum-nickel-lanthanum alloy film and a titanium film were sequentially deposited by a sputtering method. The thickness of the aluminum-nickel-lanthanum alloy film was 200 inn and the thickness of the titanium film was 6 nm. In this example, the first electrode 101 was used as an anode.

Next, as pretreatment for forming the light-emitting element over the substrate, UV-ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate over which the first electrode 101 was formed was fixed to a substrate holder provided in the vacuum evaporation apparatus so that the surface on which the first electrode 101 was formed faced downward. By an evaporation method using resistance heating, 9-phenyl-3-[4-(10-phenyl-9-anthryl)phenyl]-9H-carbazole (abbreviation: PCzPA) represented by the above structural formula (i) and molybdenum(VI) oxide were deposited by co-evaporation, so that a first hole-injection layer 111_1 was formed. The thickness of the first hole-injection layer 111_1 was set to 13 nm, and the weight ratio of PCzPA to molybdenum oxide was adjusted to 4:2 (=PCzPA:molybdenum oxide). Note that the co-evaporation method refers to an evaporation method in which evaporation is carried out from a plurality of evaporation sources at the same time in one treatment chamber.

Next, a film of PCzPA was formed to a thickness of 20 nm over the first hole-injection layer 111_1 to form a first hole-transport layer 112_1.

Furthermore, over the first hole-transport layer 112_1, a first light-emitting layer 113_1 was formed by co-evaporation of 7-[4-(10-phenyl-9-anthryl)phenyl]-7H-dibenzo[c,g]carbazole (abbreviation: cgDBCzPA) represented by the above structural formula (ii) and N,N-bis(3-methylphenyl)-N,N'-bis[3-(9-phenyl-9H-fluoren-9-yl)phenyl]-pyrene-1,6-diamine (abbreviation: 1,6mMemFLPAPrn) represented by the above structural formula (iii) in a weight ratio of 1:0.03 (=cgDBCzPA:1,6mMemFLPAPrn) to a thickness of 30 nm.

After that, cgDBCzPA was deposited to a thickness of 5 nm, and 2,2'-(pyridine-2,6-diyl)bis(4-phenylbenzo[h]quinazoline) (abbreviation: 2,6(P-Bqn)2Py) represented by the above structural formula (iv) was deposited to a thickness of 15 nm, so that a first electron-transport layer 114_1 and a first electron-injection layer 115_1 were formed. Components from the first hole-injection layer 111_1 to the first electron-transport layer 114_1 and the first electron-injection layer 115_1 are collectively referred to as a first light-emitting unit 103_1.

Then, the charge-generation layer 116 was formed over the first light-emitting unit 103_1. The charge-generation layer 116 was formed in the following manner. First, as the electron-injection buffer layer 119, lithium oxide ($Li_2O$) was deposited to a thickness of 0.1 nm. Then, as the electron-relay layer 118, copper phthalocyanine (abbreviation: CuPc) represented by the above structural formula (vi) was deposited to a thickness of 2 nm. After that, as the p-type layer 117, PCzPA and molybdenum(VI) oxide were deposited by co-evaporation to a thickness of 33 nm. The weight ratio of PCzPA to molybdenum oxide was adjusted to 4:2 (=PCzPA:molybdenum oxide).

Next, over the charge-generation layer 116, 4-phenyl-4'-(9-phenylfluoren-9-yl)triphenylamine (abbreviation: BPAFLP) represented by the above structural formula (viii) was deposited to a thickness of 20 nm as a second hole-transport layer 112_2.

Then, a second light-emitting layer 113_2 was formed by co-evaporation of 2-[3'-(dibenzothiophen-4-yl)biphenyl-3-yl]dibenzo[f,h]quinoxaline (abbreviation: 2mDBTBPDBq- II) represented by the above structural formula (ix), N-(1,1'-biphenyl-4-yl)-9,9-dimethyl-N-[4-(9-phenyl-9H-carbazol-3-yl)phenyl]-9H-fluoren-2-ami ne (abbreviation: PCBBiF) represented by the above structural formula (x), and (acetylacetonato)bis(4,6-diphenylpyrimidinato)iridium (III) (abbreviation: [Ir(dppm)$_2$(acac)]) represented by the above structural formula (xi) in a weight ratio of 0.8:0.2:0.05 (=2mDBTBPDBq-II:PCBBiF:[Ir(dppm)$_2$(acac)]) to a thickness of 30 nm.

After that, over the second light-emitting layer 113_2, 2mDBTBPDBq-II was deposited to a thickness of 10 nm, so that a second electron-transport layer 114_2 was formed. Furthermore, bathophenanthroline (abbreviation: BPhen) represented by the structural formula (vii) was deposited to a thickness of 10 nm, whereby a second electron-injection layer 115_2 was formed.

After the second electron-injection layer 115_2 was formed, lithium oxide (Li$_2$O) was deposited to a thickness of 0.1 nm by evaporation and then silver was deposited to a thickness of 15 nm, whereby the second electrode 102 serving as a cathode was formed. Then, PCzPA was deposited to a thickness of 70 nm to form a layer for relaxing a refractive index. Thus, the light-emitting element was fabricated. Components from the second hole-transport layer 112_2 to the second electron-injection layer 115_2 corresponds to a second light-emitting unit 103_2.

Note that in the above deposition steps, evaporation was performed by a resistance-heating method.

The light-emitting element used for the comparative light-emitting device 1 was fabricated in the same manner as the light-emitting element used for the light-emitting device 1 except for changing 2,6(P-Bqn)2Py in the light-emitting element used for the light-emitting device 1 to BPhen represented by the structural formula (vii). The light-emitting element used for the comparative light-emitting device 2 was fabricated in the same manner as the light-emitting element used for the light-emitting device 1 except for changing 2,6(P-Bqn)2Py in the light-emitting element used for the light-emitting device 1 to 2,6(P2Pm)2Py represented by the above structural formula (v).

The light-emitting devices including the light-emitting elements fabricated as described above were sealed using a glass substrate in a glove box containing a nitrogen atmosphere so as not to be exposed to the air (specifically, a sealing material was applied to surround the elements and UV treatment and heat treatment at 80° C. for 1 hour were performed at the time of sealing). Then, crosstalk in these light-emitting devices was evaluated.

Figure 26:
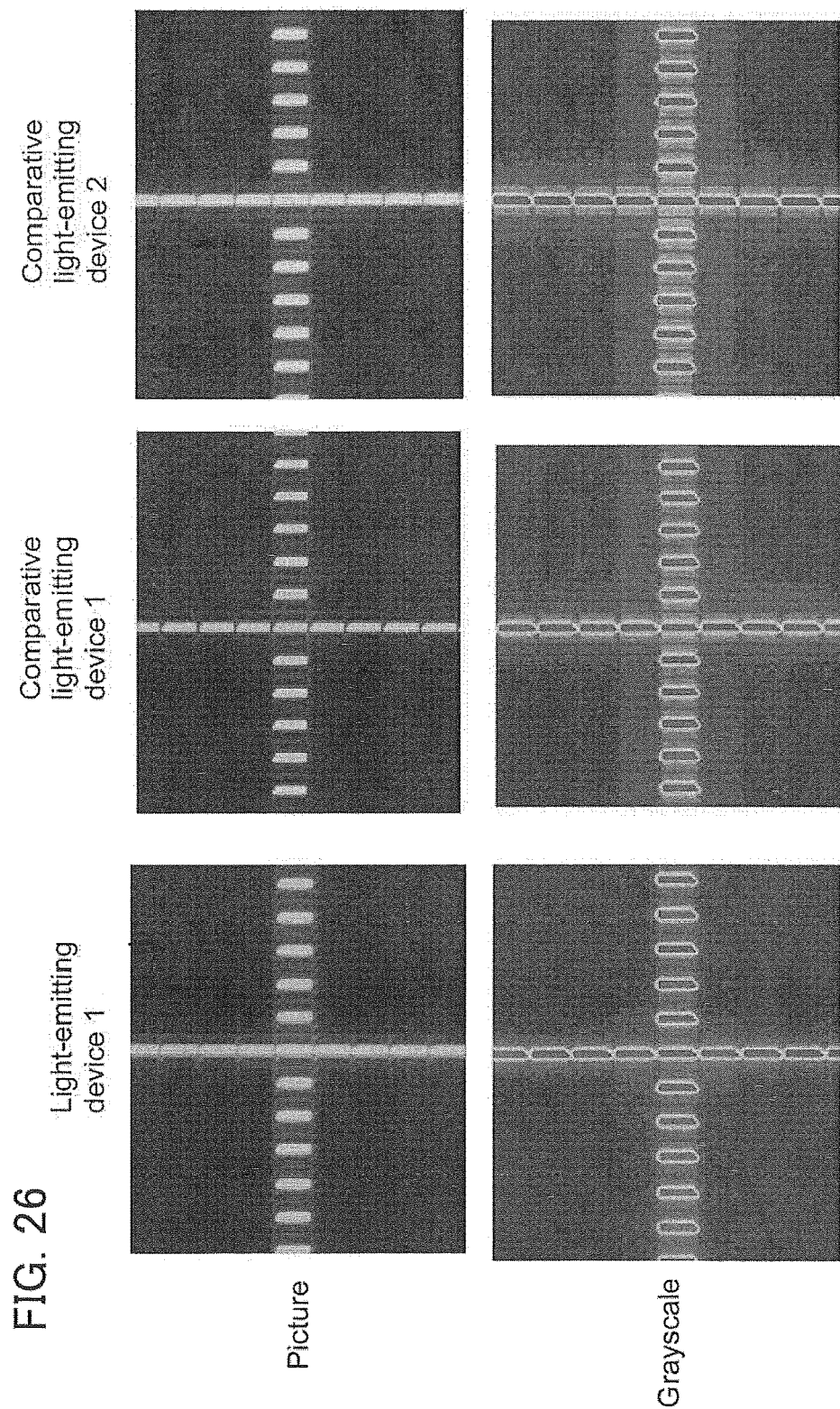
FIG. 26 shows images for verifying crosstalk in the light-emitting devices.

FIG. 26 shows photomicrographs and grayscale images of the light-emitting device 1 and the comparative light-emitting devices 1 and 2. Assuming a display device with the RGB stripe arrangement, as pixels of the same color in the RGB stripe pixel arrangement, all the pixels in one column and every third pixel in one row were made to emit light.

As can be clearly seen from FIG. 26, particularly from the grayscale images, a significant adverse effect is found on pixels adjacent to the pixels that were made to emit light in the comparative light-emitting devices 1 and 2. In contrast, in the light-emitting device 1 including the organic compound of one embodiment of the present invention, there is no significant adverse effect on pixels adjacent to pixels that were made to emit light, and high display quality can be obtained.

The above is probably because BPhen and 2,6(P2Pm)2Py in the first electron-transport layer 114_1 of the comparative light-emitting devices 1 and 2, which were in contact with lithium oxide in the electron-injection buffer layer 119 of the charge-generation layer 116, allow diffusion of lithium to increase the electrical conductivity of the first electron-transport layer 114_1 and flow current to the light-emitting layer closer to the cathode than the charge-generation layer in the pixels adjacent to the pixels that were made to emit light.

However, 2,6(P-Bqn)2Py in the light-emitting device 1, which is unlikely to cause such a problem, reduced the degree of crosstalk.

As described above, the light-emitting device 1 including the organic compound of one embodiment of the present invention can have high display quality and less crosstalk.

Example 6

Synthesis Example 3

In this example, a method of synthesizing 2,2'-(2,2'-bipyridine-6,6'-diyl)bis(4-phenylbenzo[h]quinazoline) (abbreviation: 6,6'(P-Bqn)2BPy), which is represented by the structural formula (401) in Embodiment 1, is described. The structure of 6,6'(P-Bqn)2BPy is shown below.

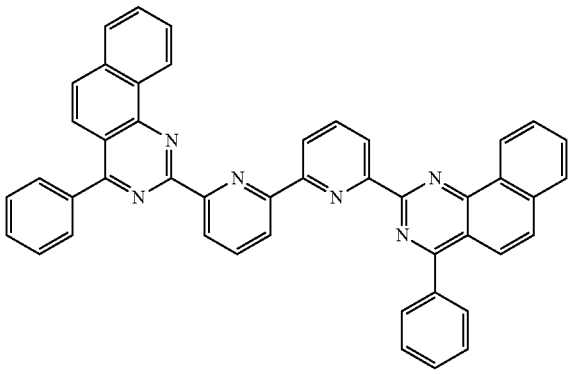

(401) 6,6'(P-Bqn)2BPy

Step 1: Synthesis of
2,2'-bipyridine-6,6'-dicarboxamidine
dihydrochloride

First, 6.2 g (30 mmol) of 2,2'-bipyridine-6,6'-dicarbonitrile and 120 mL of methanol (dehydrated) were put into a 300-mL three-neck flask. Then, 149 mg (2.8 mmol) of sodium methoxide was added to this mixture, and the mixture was stirred under a nitrogen stream at room temperature for four days. After that, 3.2 g (60 mmol) of ammonium chloride was added to the mixture, and the mixture was stirred under a nitrogen stream at room temperature for two days to be reacted. After the reaction, the mixture was suction filtered to give a solid. The obtained solid was washed with ethyl acetate to give 8.5 g of a white solid in a yield of 90%. The obtained white solid was identified as 2,2'-bipyridine-6,6'-dicarboxamidine dihydrochloride by nuclear magnetic resonance (NMR) spectroscopy. The synthesis scheme (a-3) of the step 1 is illustrated below.

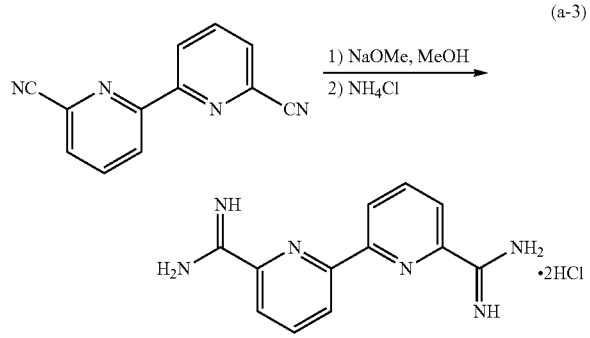

(a-3)

Step 2: Synthesis of N,N'-di(naphthalen-1-yl)-2,2'-bipyridine-6,6'-dicarboxamidine>

First, 8.5 g (27 mmol) of 2,2'-bipyridine-6,6'-dicarboxamidine dihydrochloride, 35 g (109 mmol) of cesium carbonate, and 0.51 g (2.7 mmol) of copper iodide were put into a reaction container, and the air in the flask was replaced with nitrogen. Then, 60 mL of N,N'-dimethylformamide, 14 g (54 mmol) of 1-iodonaphthalene, and 0.48 g (5.4 mmol) of N,N'-dimethylethylenediamine were added to this mixture, and the mixture was stirred to be degassed while the pressure in the flask was reduced. After that, the mixture was heated under a nitrogen stream at 90° C. for 26 hours. After the reaction mixture was suction filtered, the residue was washed with water and chloroform to give a filtrate. The obtained filtrate was subjected to extraction with chloroform. The obtained solution of the extract was washed with water and saturated brine. Then, anhydrous magnesium sulfate was added for drying. This mixture was subjected to gravity filtration, and the filtrate was concentrated to give a solid. Toluene was added to the obtained solid, and the mixture was suction filtered to give 4.3 g of a yellow solid in a yield of 32%. The obtained yellow solid was identified as N,N'-di(naphthalen-1-yl)-2,2'-bipyridine-6,6'-dicarboxamidine by nuclear magnetic resonance (NMR) spectroscopy. The synthesis scheme (b-3) of the step 2 is illustrated below.

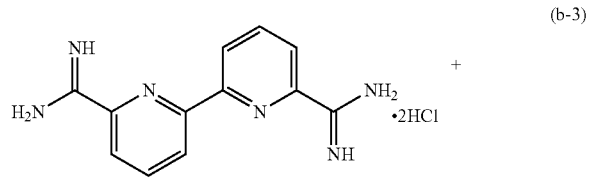

(b-3)

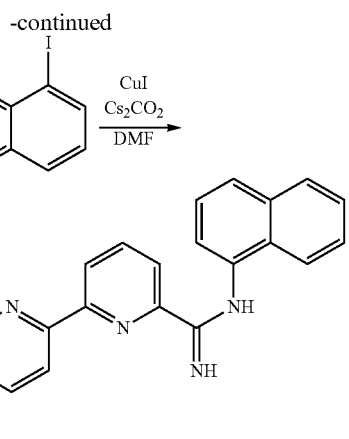

Step 3: Synthesis of 2,2'-(2,2'-bipyridine-6,6'-diyl)bis(4-phenylbenzo[h]quinazoline) (abbreviation: 6,6'(P-Bqn)2BPy)

First, 4.3 g (8.7 mmol) of N, N'-di(naphthalen-1-yl)-2,2'-bipyridine-6,6'-dicarboxamidine and 9.2 g (87 mmol) of benzaldehyde were put into a 200-mL three-neck flask, and the mixture was heated under a nitrogen stream at 180° C. for 1 hour. After the reaction, the mixture was purified by silica column chromatography. A solvent of toluene and ethyl acetate in a ratio of 10:1 was used as the developing solvent. The obtained fraction was concentrated to give a solid. Ethyl acetate was added to the obtained solid. The mixture was irradiated with ultrasonic waves, and the lump was crushed into pieces and then suction filtered to give 2.4 g of a yellow solid in a yield of 41%. The obtained yellow solid was identified as a dihydro body of the desired substance by nuclear magnetic resonance (NMR) spectroscopy. Then, 2.4 g (3.6 mmol) of this dihydro body and 360 mL of xylene were added to a 1000-mL three-neck flask. To this mixture was added 3.6 g (14 mmol) of p-chloranil and the mixture was heated under a nitrogen stream at 160° C. for 5 hours. Toluene was added to the reaction mixture, and the mixture was suction filtered to give 1.8 g of a yellow solid in a yield of 75%. By a train sublimation method, 1.8 g of the obtained solid was purified, so that 1.3 g of a white solid was obtained at a collection rate of 72%. Note that the sublimation purification was performed under a pressure of $3.0 \times 10^{-3}$ Pa at 330° C. for 17 hours. The synthesis scheme (c-3) of the step 3 is illustrated below.

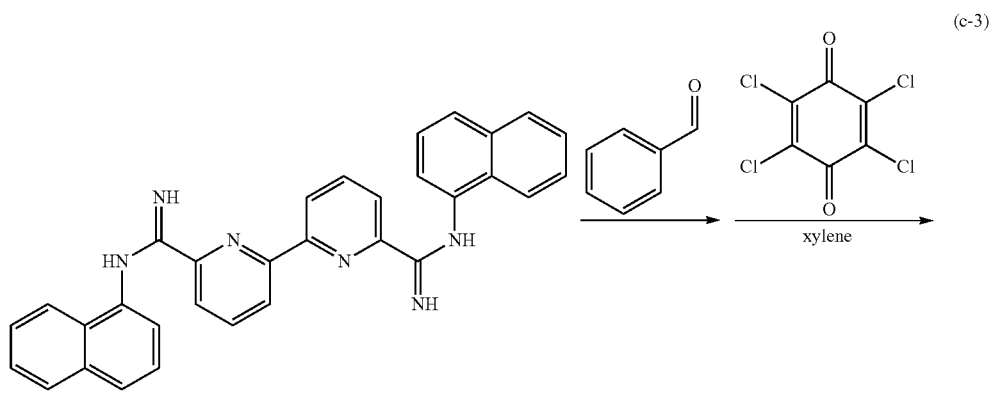

(c-3)

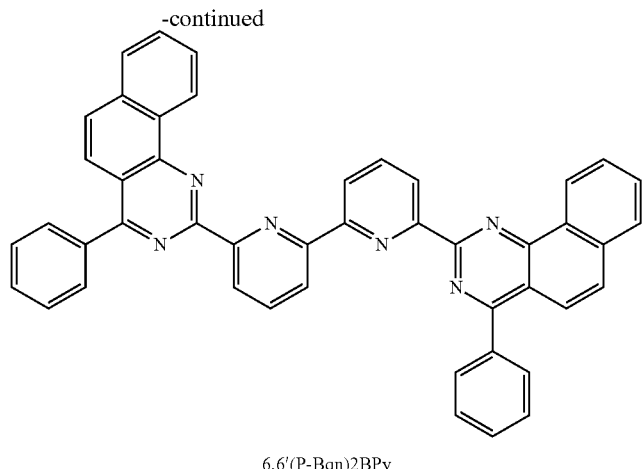

6,6'(P-Bqn)2BPy

Figure 29A:
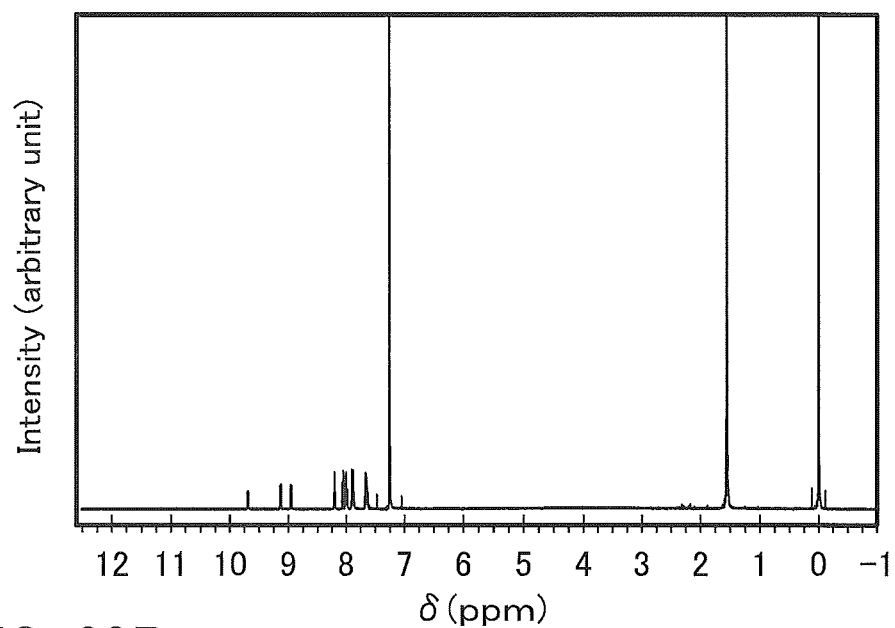
FIGS. 29A and 29B show $^1$H-NMR charts of 6,6(N-Bqn)2BPy.
Figure 29B:
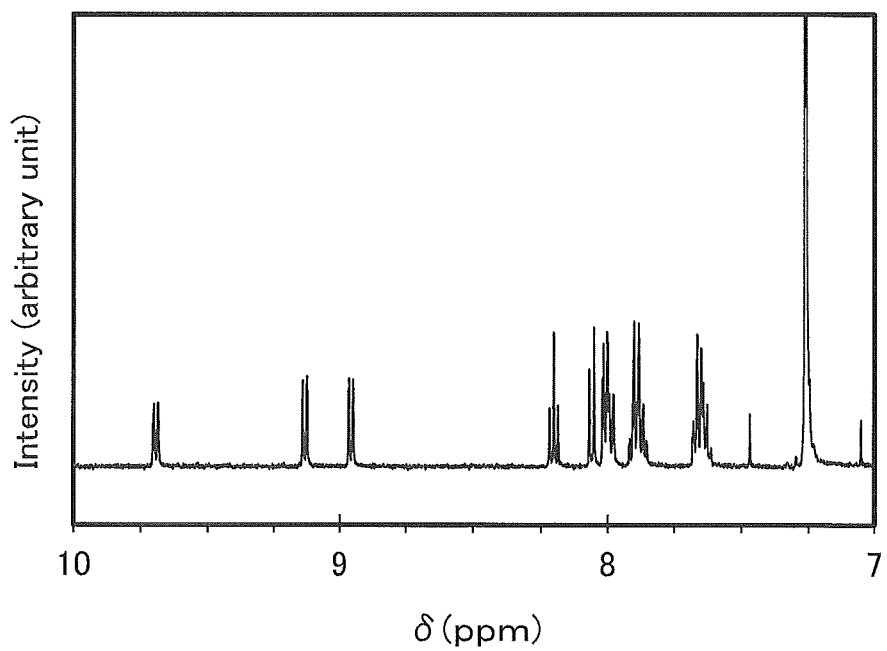

Protons ($^1$H) of the white solid which was obtained through the step 3 described above was measured by nuclear magnetic resonance (NMR) spectroscopy. The obtained values are shown below. FIGS. 29A and 29B show the $^1$H-NMR charts. FIG. 29B is a chart where the range of from 7 ppm to 10 ppm in FIG. 29A is enlarged. These results reveal that 6,6'(P-Bqn)2BPy, which is an organic compound of one embodiment of the present invention and represented by the above structural formula (401), was obtained.

$^1$H-NMR δ (CDCl$_3$): 7.61-7.68 (m, 6H), 7.86-7.92 (m, 6H), 7.98-8.02 (m, 6H), 8.06 (d, 2H), 8.20 (t, 2H), 8.96 (d, 2H), 9.13 (d, 2H), 9.69 (d, 2H)

Example 7

In this example, a light-emitting element 3 containing 2,2'-(pyridine-2,6-diyl)bis(4-phenylbenzo[h]quinazoline) (abbreviation: 2,6(P-Bqn)2Py) represented by the structural formula (401) in Embodiment 1, which was synthesized in Synthesis example 1, in an electron-transport layer and an electron-injection layer and a comparative light-emitting element 3 containing 2,6(P-Bqn)2Py in an electron-transport layer and bathophenanthroline (abbreviation: BPhen) in an electron-injection layer are described. Structure formulae of organic compounds used in the light-emitting element 3 and the comparative light-emitting element 3 are shown below.

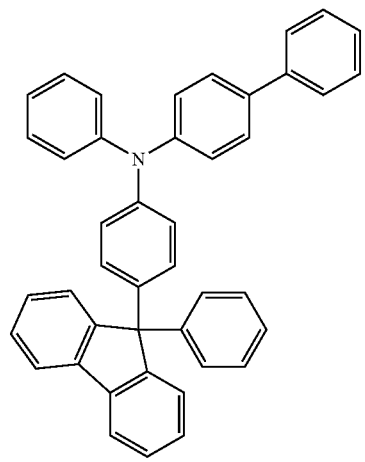

(viii) BPAFLP (xii) DBT3P-II (ix) 2mDBTPDBq-II

-continued

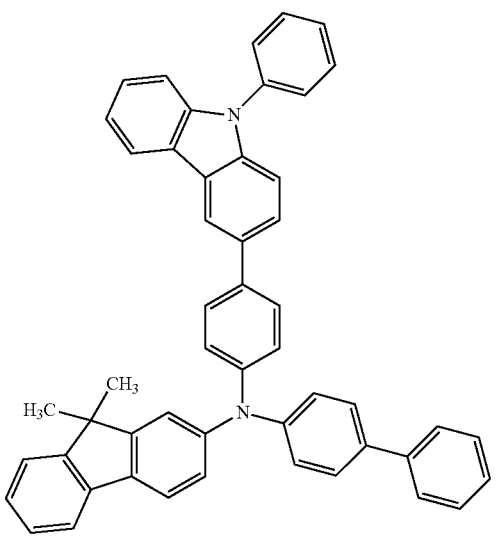

PCBBiF
(x)

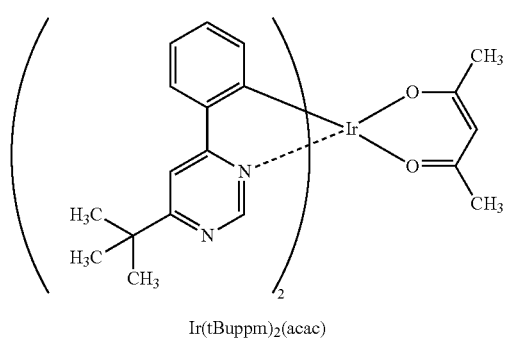

Ir(tBuppm)₂(acac)
(xiii)

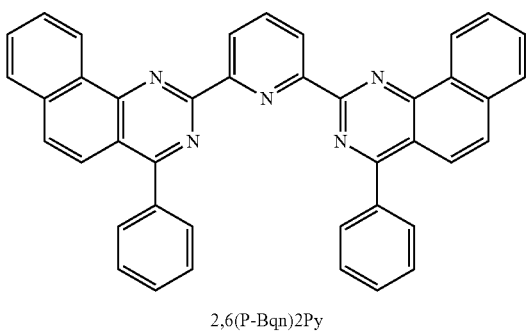 [SMILES: c1ccc(-c2nc(-c3cccc(-c4nc(-c5ccccc5)c5ccc6ccccc6c5n4)n3)nc3c2ccc2ccccc23)cc1]

2,6(P-Bqn)2Py
(iv)

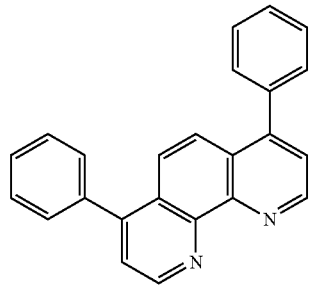

BPhen
(vii)

(Method of Fabricating Light-Emitting Element 3)

First, a film of indium tin oxide containing silicon oxide (ITSO) was formed over a glass substrate by a sputtering method, so that the first electrode 101 was formed. The thickness thereof was 110 nm and the electrode area was 2 mm×2 mm. Here, the first electrode 101 functions as an anode of the light-emitting element.

Next, as pretreatment for forming the light-emitting element over the substrate, UV-ozone treatment was performed for 370 seconds after washing of a surface of the substrate with water and baking that was performed at 200° C. for one hour.

After that, the substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the substrate over which the first electrode 101 was formed was fixed to a substrate holder provided in the vacuum evaporation apparatus so that the surface on which the first electrode 101 was formed faced downward. Over the first electrode 101, 4,4',4"-(benzene-1,3,5-triyl)tri(dibenzothiophene) represented by the above structural formula (xii) and molybdenum(VI) oxide were deposited by co-evaporation by an evaporation method using resistance heating, so that the hole-injection layer 111 was formed. The thickness of the hole-injection layer 111 was set to 60 nm, and the weight ratio of DBT3P-II to molybdenum oxide was adjusted to 4:2 (=DBT3P-II:molybdenum oxide). Note that the co-evaporation method refers to an evaporation method in which evaporation is carried out from a plurality of evaporation sources at the same time in one treatment chamber.

Next, a film of BPAFLP represented by the above structural formula (viii) was formed to a thickness of 20 nm over the hole-injection layer 111 to form the hole-transport layer 112.

Furthermore, over the hole-transport layer 112, the light-emitting layer 113 was formed by co-evaporation of 2mDBTBPDBq-II represented by the above structural formula (ix), PCBBiF represented by the above structural formula (x), and bis[2-(6-tert-butyl-4-pyrimidinyl-kN3)phenyl-kC](2,4-pentanedionato-k²O,O')iridium(III) (abbreviation: [Ir(tBuppm)₂(acac)]) represented by the above structural formula (xiii) in a weight ratio of 0.7:0.3:0.05 (=2mDBTBPDBq-II:PCBBiF:[ft(tBuppm)₂(acac)]) to a thickness of 20 nm and then by co-evaporation of them in a weight ratio of 0.8:0.2:0.05 (=2mDBTBPDBq-II:PCBBiF:[Ir(tBuppm)₂(acac)]) to a thickness of 20 nm.

Then, the electron-transport layer 114 and the electron-injection layer 115 were formed over the light-emitting layer 113 in such a manner that a 25 nm thick film of 2,6(P-Bqn)2Py represented by the above structural formula (iv) was formed.

After the formation of the electron-transport layer 114 and the electron-injection layer 115, lithium fluoride (LiF) was deposited by evaporation to a thickness of 1 nm and aluminum was deposited by evaporation to a thickness of 200 nm to form the second electrode 102. Thus, the light-emitting element 3 in this example was fabricated.

(Method of Fabricating Comparative Light-Emitting Element 3)

The comparative light-emitting element 3 was fabricated in the same manner as the light-emitting element 3 except for forming a 15 nm thick film of 2,6(P-Bqn)2Py as the electron-transport layer 114 and forming a 10 nm thick film of BPhen represented by the above structural formula (vii) as the electron-injection layer 115.

The element structures of the light-emitting element 3 and the comparative light-emitting element 3 are shown in a table below.

In addition, 2,6(P-Bqn)2Py was found to be a substance with high triplet excitation level which can retain favorable efficiency even when used for the electron-transport layer adjacent to the light-emitting layer of a green phosphorescence emitting element.

TABLE 5

| Hole-injection layer | Hole-transport layer | Light-emitting layer | Electron-transport layer | Electron-injection layer |
|---|---|---|---|---|
| DBT3P-II:MoOx 4:2 | BPAFLP | 2mDBTBPDBq-II:PCBBiF:Ir(tBuppm)$_2$(acac) 0.7:0.3:0.05    0.8:0.2:0.05 | 2,6(P-Bqn)2Py | *3 |
| 60 nm | 10 nm | 20 nm                       20 nm | 15 nm | 10 nm |

*3 Light-emitting element 3: 2,6(P-Bqn)2Py Comparative light-emitting element 3: BPhen The light-emitting element 3 and the comparative light-emitting element 3 were each sealed using a glass substrate in a glove box containing a nitrogen atmosphere so as not to be exposed to the air (specifically, a sealing material was applied to surround the elements and UV treatment and heat treatment at 80° C. for 1 hour were performed at the time of sealing). Then, initial characteristics and reliability of these light-emitting elements were measured. Note that the measurements were carried out at room temperature (in an atmosphere kept at 25° C.).

Figure 30:
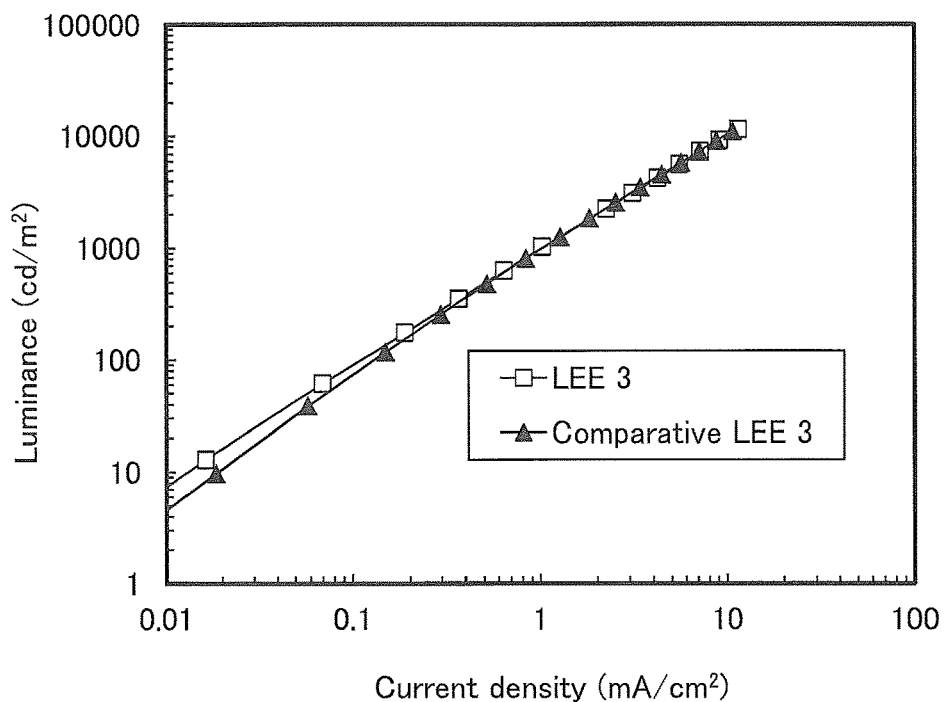
FIG. 30 shows current density-luminance characteristics of a light-emitting element 3 (abbreviation: LEE 3) and a comparative light-emitting element 3 (abbreviation: Comparative LEE 3).
Figure 31:
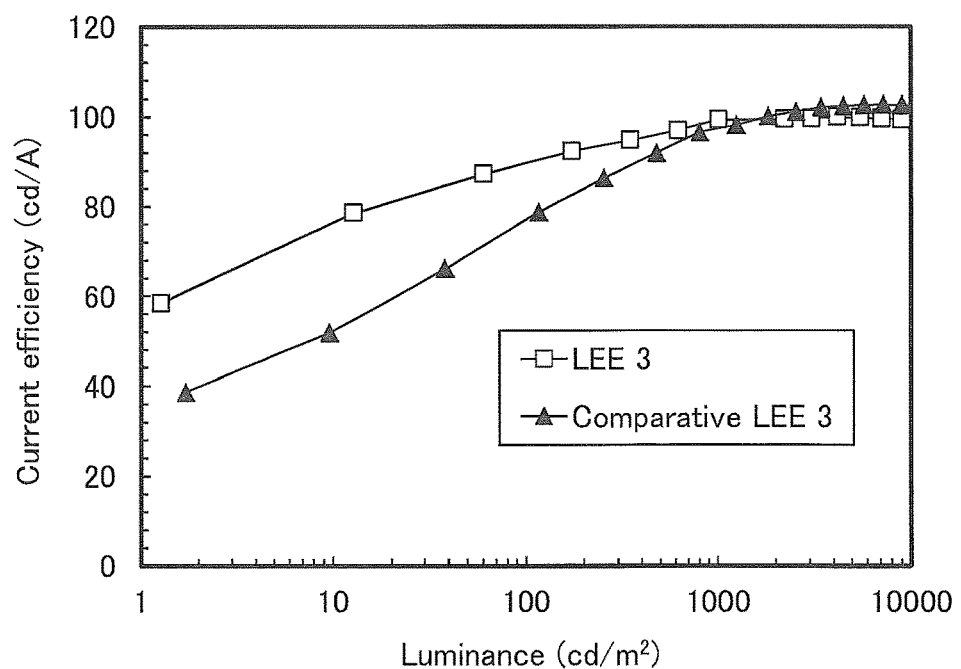
FIG. 31 shows luminance-current efficiency characteristics of the light-emitting element 3 and the comparative light-emitting element 3.
Figure 32:
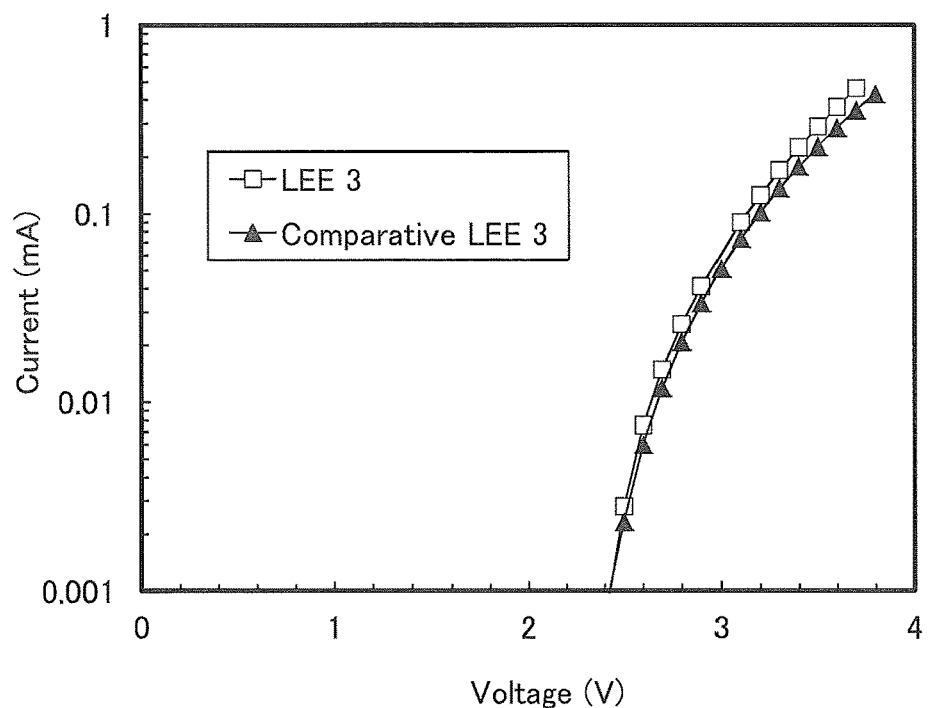
FIG. 32 shows voltage-current characteristics of the light-emitting element 3 and the comparative light-emitting element 3.
Figure 33:
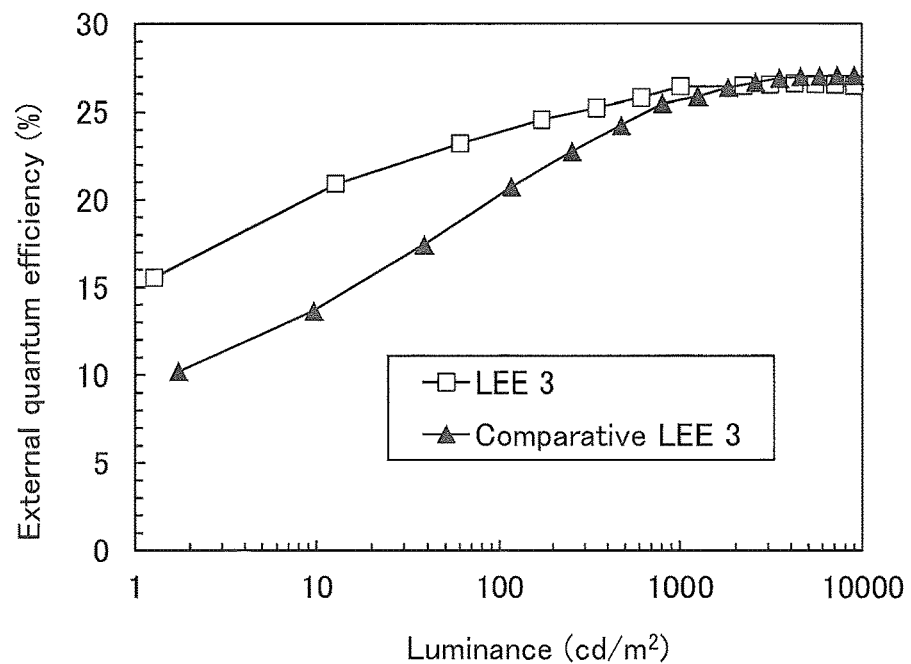
FIG. 33 shows luminance-external quantum efficiency characteristics of the light-emitting element 3 and the comparative light-emitting element 3.

FIG. 30 shows current density-luminance characteristics of the light-emitting element 3 and the comparative light-emitting element 3. FIG. 31 shows luminance-current efficiency characteristics thereof. FIG. 32 shows voltage-current characteristics thereof. FIG. 33 shows luminance-external quantum efficiency characteristics thereof. Table 6 shows main characteristics of the light-emitting elements at approximately 1000 cd/m$^2$.

TABLE 6

|  | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting element 3 | 2.9 | 0.04 | 1 | 0.42 | 0.57 | 99.2 | 26.4 |
| Comparative light-emitting element 3 | 2.9 | 0.03 | 1 | 0.41 | 0.58 | 96.5 | 25.4 |

It can be found from FIG. 30, FIG. 31, FIG. 32, FIG. 33, and Table 6 that each of the light-emitting elements is a green light-emitting element with favorable characteristics.

Figure 34:
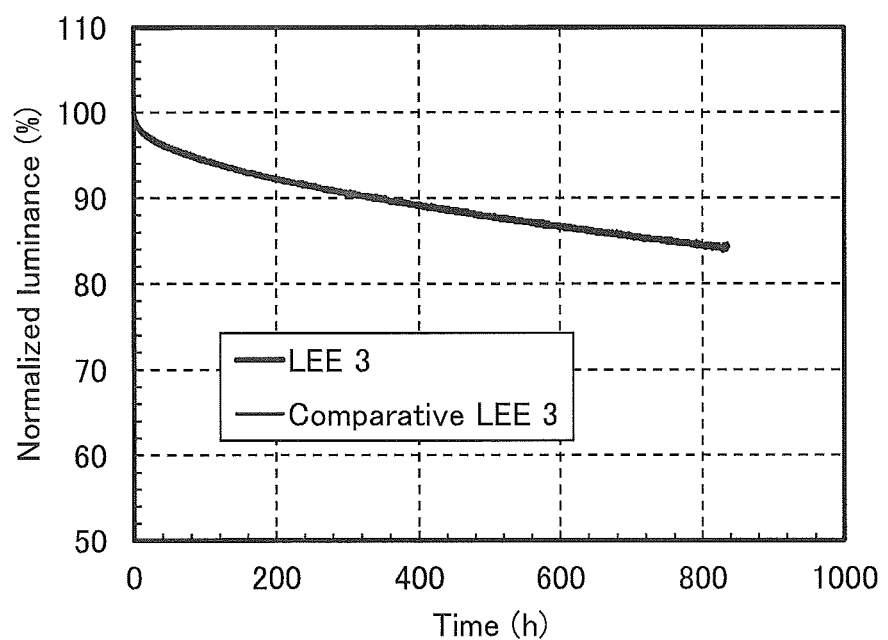
FIG. 34 shows characteristics of normalized luminance change with time of the light-emitting element 3 and the comparative light-emitting element 3.

FIG. 34 shows changes in luminance of the light-emitting elements with driving time under the conditions where the initial luminance was 5000 cd/m$^2$ and the current density was constant. As shown in FIG. 34, the light-emitting element 3, which is a light-emitting element of the present invention, shows as high reliability as the comparative light-emitting element 3. This means that a light-emitting element including the organic compound of one embodiment the present invention shows very high reliability.

Furthermore, since 2,6(P-Bqn)2Py has high heat resistance because of its rigid skeleton and moderate molecular weight, the light-emitting element 3 including 2,6(P-Bqn)2Py has high heat resistance.

REFERENCE NUMERALS

101: first electrode, 102: second electrode, 103: EL layer, 103_1: first light-emitting unit, 103_2: second light-emitting unit, 111: hole-injection layer, 111_1: first hole-injection layer, 112: hole-transport layer, 112_1: first hole-transport layer, 112_2: second hole-transport layer, 113: light-emitting layer, 113_1: first light-emitting layer, 113_2: second light-emitting layer, 114: electron-transport layer, 114_1: first electron-transport layer, 114_2: second electron-transport layer, 115: electron-injection layer, 115_1: first electron-injection layer, 115_2: second electron-injection layer, 116: charge-generation layer, 117: p-type layer, 118: electron-relay layer, 119: electron-injection buffer layer, 400: substrate, 401: first electrode, 403: EL layer, 404: second electrode, 405: sealing material, 406: sealing material, 407: sealing substrate, 412: pad, 420: IC chip, 501: first electrode, 502: second electrode, 511: first light-emitting unit, 512: second light-emitting unit, 513: charge-generation layer, 601: driver circuit portion (source line driver circuit), 602: pixel portion, 603: driver circuit portion (gate line driver circuit), 604: sealing substrate, 605: sealing material, 607: space, 608: wiring, 609: FPC (flexible printed circuit), 610: element substrate, 611: switching FET, 612: current controlling FET, 613: first electrode, 614: insulator, 616: EL layer, 617: second electrode, 618: light-emitting element, 901: housing, 902: liquid crystal layer, 903: backlight unit, 904: housing, 905: driver IC, 906: terminal, 951: substrate, 952: electrode, 953: insulating layer, 954: partition layer, 955: EL layer, 956: electrode, 1001: substrate, 1002: base insulating film, 1003: gate insulating film, 1006: gate electrode, 1007: gate electrode, 1008: gate electrode, 1020: first interlayer insulating film, 1021: second interlayer insulating film, 1022: electrode, 1024W: first electrode of light-emitting element, 1024R: first electrode of light-emitting element, 1024G: first electrode of light-emitting element, 1024B: first electrode of light-emitting element, 1025: partition, 1028: EL layer, 1029: second electrode of light-emitting element, 1031: sealing substrate, 1032: sealing material, 1033: transparent base material, 1034R: red coloring layer, 1034G: green coloring layer, 1034B: blue coloring layer, 1035: black matrix, 1036: overcoat layer, 1037: third interlayer insulating film, 1040: pixel portion, 1041: driver circuit portion, 1042: peripheral portion, 2001: housing, 2002: light source, 3001: lighting device, 5000: display region, 5001: display region, 5002: display region, 5003: display region, 5004: display region, 5005: display region, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7210: second display portion, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7401: housing, 7402: display portion, 7403: operation button, 7404: external connection port, 7405: speaker, 7406: microphone, 7400: mobile phone, 9033: clasp, 9034: switch, 9035: power switch, 9036: switch, 9038: operation switch, 9310: portable information terminal, 9311: display panel, 9312: display region, 9313: hinge, 9315: housing, 9630: housing, 9631: display portion, 9631a: display portion, 9631b: display portion, 9632a: touch panel region, 9632b: touch panel region, 9633: solar cell, 9634: charge and discharge control circuit, 9635: battery, 9636: DCDC converter, 9637: operation key, 9638: converter, 9639: button This application is based on Japanese Patent Application serial no. 2015-029560 filed with Japan Patent Office on Feb. 18, 2015, the entire contents of which are hereby incorporated by reference.

The invention claimed is:

1. A light-emitting element comprising:
a first electrode;
a first light-emitting unit over the first electrode;
a second light-emitting unit over the first light-emitting unit;
a first layer between the first light-emitting unit and the second light-emitting unit;
a second layer between the first electrode and the first layer; and
a second electrode over the second light-emitting unit,
wherein the first light-emitting unit comprises a first light-emitting layer,
wherein the second light-emitting unit comprises a second light-emitting layer,
wherein the second layer comprises an organic compound represented by a general formula (G1):

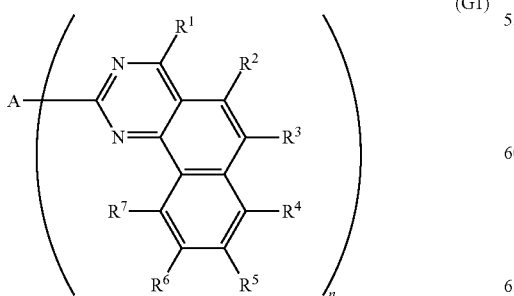

wherein a substituent A represents a substituted or unsubstituted aromatic ring having 3 to 30 carbon atoms or a substituted or unsubstituted heteroaromatic ring having 3 to 30 carbon atoms,
wherein each of $R^1$ to $R^7$ independently represents any of hydrogen, an alkyl group having 1 to 6 carbon atoms, and a substituted or unsubstituted aromatic hydrocarbon group having 6 to 13 carbon atoms, and
wherein n is 2 or 3.

2. A display module comprising the light-emitting element according to claim 1.

3. A lighting module comprising the light-emitting element according to claim 1.

4. An electronic device comprising the light-emitting element according to claim 1.

5. The electronic device according to claim 4, further comprising,
a first light-emitting element;
a second light-emitting element; and
a third light-emitting element,
wherein the second light-emitting element is between the first light-emitting element and the third light-emitting element.

6. The light-emitting element according to claim 1, wherein the second layer is in contact with the first layer.

7. The light-emitting element according to claim 1, wherein the organic compound is represented by a general formula (G2):

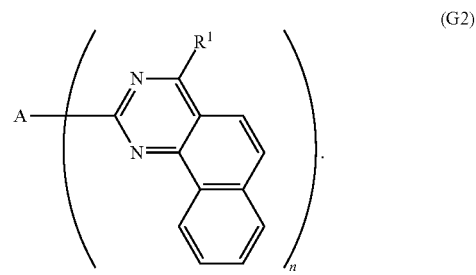

8. The light-emitting element according to claim 1, wherein the organic compound is represented by a general formula (G3):

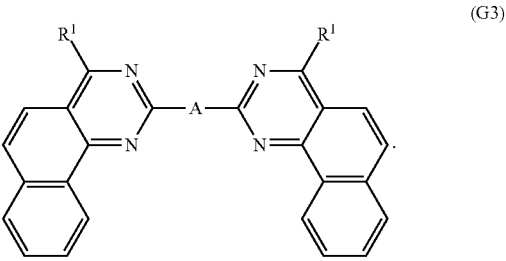

9. The light-emitting element according to claim 1, wherein the substituent A represents a substituent comprising one or more pyridine skeletons or one or more rings each comprising a benzene skeleton and having less than or equal to 30 carbon atoms.

10. The light-emitting element according to claim 1, wherein the organic compound is represented by a general formula (G4):

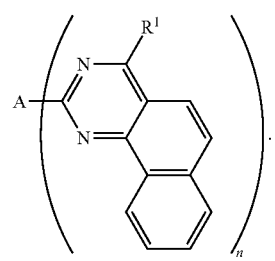

(G2)

11. The light-emitting element according to claim 1, wherein R¹ represents a phenyl group or a naphthyl group.

12. A light-emitting element comprising:
- a first electrode;
- a first layer over the first electrode;
- a second layer over the first layer;
- a third layer over the second layer; and
- a second electrode over the third layer,
- wherein the second layer comprises at least one of an alkali metal or an alkaline earth metal,
- wherein the first layer comprises a first light-emitting substance and an organic compound represented by a general formula (G1):

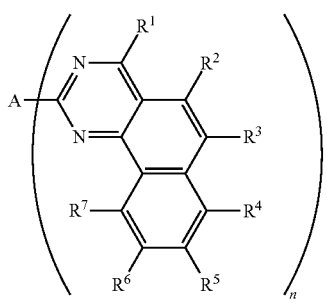

(G1)

wherein a substituent A represents a substituted or unsubstituted aromatic ring having 3 to 30 carbon atoms or a substituted or unsubstituted heteroaromatic ring having 3 to 30 carbon atoms, wherein each of R¹ to R⁷ independently represents any of hydrogen, an alkyl group having 1 to 6 carbon atoms, and a substituted or unsubstituted aromatic hydrocarbon group having 6 to 13 carbon atoms, wherein n is 2 or 3, and wherein the third layer comprises a second light-emitting substance.

13. The light-emitting element according to claim 12, wherein the second layer is in contact with the first layer.

14. The light-emitting element according to claim 12, wherein the organic compound is represented by a general formula (G2):

15. The light-emitting element according to claim 12, wherein the organic compound is represented by a general formula (G3):

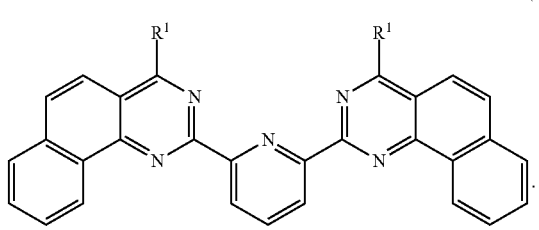

(G3)

16. The light-emitting element according to claim 12, wherein the substituent A represents a substituent comprising one or more pyridine skeletons or one or more rings each comprising a benzene skeleton and having less than or equal to 30 carbon atoms.

17. The light-emitting element according to claim 12, wherein the organic compound is represented by a general formula (G4):

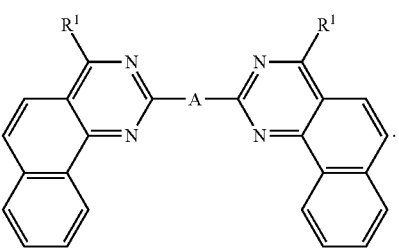

(G4)

18. The light-emitting element according to claim 12, wherein R¹ represents a phenyl group or a naphthyl group.

19. An electronic device comprising the light-emitting element according to claim 12, further comprising,
- a first light-emitting element;
- a second light-emitting element; and
- a third light-emitting element,
- wherein the second light-emitting element is between the first light-emitting element and the third light-emitting element.

20. A display module comprising the light-emitting element according to claim 12.

21. A lighting module comprising the light-emitting element according to claim 12.

* * * * *